United States Patent
Altieri et al.

(10) Patent No.: US 9,035,024 B2
(45) Date of Patent: May 19, 2015

(54) COMPOUNDS THAT INHIBIT HSP90 PROTEIN-PROTEIN INTERACTIONS WITH IAP PROTEINS

(71) Applicant: University of Massachusetts, Shrewsbury, MA (US)

(72) Inventors: Dario C. Altieri, Worcester, MA (US); Janet Plescia, Meriden, CT (US); Whitney Salz, Acton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/861,959

(22) Filed: Apr. 12, 2013

(65) Prior Publication Data

US 2014/0086924 A1     Mar. 27, 2014

Related U.S. Application Data

(60) Continuation of application No. 12/033,210, filed on Feb. 19, 2008, now Pat. No. 8,420,777, which is a division of application No. 11/187,230, filed on Jul. 22, 2005, now Pat. No. 7,342,093.

(60) Provisional application No. 60/590,584, filed on Jul. 23, 2004.

(51) Int. Cl.
| | |
|---|---|
| *A61K 38/08* | (2006.01) |
| *C07K 14/47* | (2006.01) |
| *A61K 38/00* | (2006.01) |
| *G01N 33/574* | (2006.01) |
| *A61K 39/395* | (2006.01) |

(52) U.S. Cl.
CPC ............. *C07K 14/4747* (2013.01); *A61K 38/00* (2013.01); *G01N 33/574* (2013.01); *G01N 2510/00* (2013.01); *A61K 39/39558* (2013.01)

(58) Field of Classification Search
None
See application file for complete search history.

(56) References Cited

U.S. PATENT DOCUMENTS

| | | | |
|---|---|---|---|
| 6,245,523 B1 | 6/2001 | Altieri | |
| 6,346,389 B1 | 2/2002 | Altieri | |
| 6,509,162 B1 | 1/2003 | Altieri | |
| 6,541,457 B2 | 4/2003 | Korneluk et al. | |
| 6,800,737 B2 | 10/2004 | Altieri | |
| 6,943,150 B1 | 9/2005 | Altieri | |
| 7,097,966 B2 | 8/2006 | Altieri et al. | |
| 7,342,093 B2 * | 3/2008 | Altieri et al. ................. | 530/324 |
| 7,553,821 B2 | 6/2009 | Altieri | |
| 8,420,777 B2 * | 4/2013 | Altieri et al. ................. | 530/328 |
| 2002/0009730 A1 | 1/2002 | Chenchik et al. | |
| 2002/0173026 A1 | 11/2002 | Wettstein et al. | |
| 2002/0177212 A1 | 11/2002 | Patterson et al. | |
| 2003/0143232 A1 | 7/2003 | Altieri | |
| 2003/0185862 A1 | 10/2003 | Kang et al. | |
| 2003/0194704 A1 | 10/2003 | Penn et al. | |
| 2004/0126775 A1 | 7/2004 | Altieri et al. | |
| 2004/0180354 A1 | 9/2004 | Simard et al. | |
| 2005/0119454 A1 | 6/2005 | Mandell et al. | |
| 2005/0143308 A1 | 6/2005 | Altieri | |
| 2006/0035837 A1 * | 2/2006 | Altieri et al. ................... | 514/15 |
| 2006/0068453 A1 | 3/2006 | Altieri | |
| 2006/0069025 A1 | 3/2006 | Altieri | |
| 2007/0065842 A1 | 3/2007 | Altieri et al. | |
| 2008/0171693 A1 * | 7/2008 | Altieri et al. ....................... | 514/2 |
| 2009/0099080 A1 * | 4/2009 | Altieri et al. ..................... | 514/12 |
| 2011/0268722 A1 * | 11/2011 | Siegelin et al. ............. | 424/130.1 |

FOREIGN PATENT DOCUMENTS

| | | |
|---|---|---|
| CA | 2496888 | 3/2004 |
| JP | 11-326328 | 11/1999 |
| WO | WO 98/22589 | 5/1998 |
| WO | WO 02/57787 | 7/2002 |
| WO | WO 2006/080142 | 8/2006 |
| WO | WO 2006/081826 | 8/2006 |

OTHER PUBLICATIONS

USPTO Restriction Requirement in U.S. Appl. No. 11/187,230, mailed Nov. 1, 2006, 12 pages.
USPTO Non-Final Office Action in U.S. Appl. No. 11/187,230, mailed Feb. 6, 2007, 7 pages.
USPTO Notice of Allowance in U.S. Appl. No. 11/187,230, mailed Oct. 16, 2007, 7 pages.
USPTO Restriction Requirement in U.S. Appl. No. 12/033,210, mailed Jul. 23, 2010, 7 pages.
USPTO Non-Final Office Action in U.S. Appl. No. 12/033,210, mailed Oct. 21, 2010, 6 pages.
USPTO Non-Final Office Action in U.S. Appl. No. 12/033,210, mailed May 12, 2011, 7 pages.
USPTO Final Office Action in U.S. Appl. No. 12/033,210, mailed Feb. 3, 2012, 6 pages.
USPTO Notice of Allowance and Fee(s) Due in U.S. Appl. No. 12/033,210, mailed Dec. 12, 2012, 10 pages.
Examiner's First Report in AU App. Serial No. 2005269639, mailed on Oct. 7, 2010, 4 pages.
Office Action in CA App. Ser. No. 2,574,183, mailed on Mar. 6, 2012, 6 pages.
The Patent Office of the People's Republic of China, The Third Office Action in CN App. Serial No. 200580032164.1, mailed on Apr. 20, 2011, 7 pages.
Communication pursuant to Article 94(3) EPC, mailed on Mar. 13, 2013, 9 pages.
Adida et al., "Developmentally regulated expression of the novel cancer anti-apoptosis gene *survivin* in human and mouse differentiation," Am. J. Pathol., 152:43-9 (1998).
Altieri, "Molecular cloning of effector cell protease receptor-1, a novel cell surface receptor for the protease factor Xa," J. Biol. Chem., 269:3139-42 (1994).

(Continued)

*Primary Examiner* — Maury Audet
(74) *Attorney, Agent, or Firm* — Fish & Richardson P.C.

(57) ABSTRACT

Disclosed herein are compounds that inhibit Hsp90 interactions with IAP proteins, such as Survivin, XIAP, cIAP1, or cIAP2, and methods for identifying and using such compounds.

16 Claims, 25 Drawing Sheets

(56) References Cited

OTHER PUBLICATIONS

Altieri, "Splicing of effector cell protease receptor-1 mRNA is modulated by an unusual retained intron," Biochem., 33:13848-55 (1994).
Altieri, "Validating survivin as a cancer therapeutic target," Nat. Rev. Cancer, 3:46-54 (2003).
Altieri, "Xa receptor EPR-1," FASEB J. 9:860-5 (1995).
Ambrosini and Altieri, "Molecular dissection of effector cell protease receptor-1 recognition of factor Xa: assignment of critical residues involved in antibody reactivity and ligand binding," J. Biol. Chem., 271:1243-8 (1996).
Ambrosini et al., "A novel anti-apoptosis gene, *survivin*, expressed in cancer and lymphoma," Nat. Med., 3:917-921 (1997).
Basso et al., "Ansamycin antibiotics inhibit Akt activation and cyclin D expression in breast cancer cells that overexpress HER2," Oncogene, 21:1159-1166 (2002).
Birnbaum et al., "An apoptosis-inhibiting gene from a nuclear polyhedrosis virus encoding a polypeptide with Cys/His sequence motifs," J. Virol., 68:2521-8 (1994).
Blanc-Brude et al., "Therapeutic targeting of the survivin pathway in cancer: initiation of mitochondrial apoptosis and suppression of tumor-associated angiogensis," Clin. Cancer Res., 9:2683-92 (2003).
Bonny et al., "Cell-permeable peptide inhibitors of JNK: novel blockers of β-cell-cell death," Diabetes, 50:77-82 (2001).
Briand et al., "Retro-inverso peptidomimetics as new immunological probes. Validation and application to the detection of antibodies in rheumatic diseases," J. Biol. Chem., 270:20686-91 (1995).
Chen et al., "Selective killing of transformed cells by cyclin/cyclin-dependent kinase 2 antagonists," Proc. Natl. Acad. Sci. USA, 96:4325-4329 (1999).
Clem and Miller, "Control of programmed cell death by the baculovirus genes *p35* and *iap*," Mol. Cell. Biol., 14:5212-22 (1994).
Clem et al., "Anti-apoptotic genes of baculoviruses," Death and Differentiation, 3:9-16 (1996).
Deveraux and Reed, "IAP family proteins—suppressors of apoptosis", Genes Dev., 13:239- 252 (1999).
Dohi et al., "Mitochondrial survivin inhibits apoptosis and promotes tumorigenesis," J. Clin. Invest., 114:1117-27 (2004).
Duchosal et al., "In vivo immunosuppression by targeting a novel protease receptor," Nature, 380:352-6 (1996).
Duckett et al., "A conserved family of cellular genes related to the baculovirus *iap* gene and encoding apoptosis inhibitors," EMBO J., 15:2685-94 (1996).
Fortugno et al., "Regulation of survivin function by Hsp90," Proc. Natl. Acad. Sci. USA, 100:13791-796 (2003).
Fortugno et al., "Survivin exists in immunochemically distinct subcellular pools and is involved in spindle microtubule function," J. Cell Sci., 115:575-585 (2002).
Gratton et al., "Cell-permeable peptides improve cellular uptake and therapeutic gene delivery of replication-deficient viruses in cells and in vivo," Nat. Med., 9:357-362 (2003).
Grossman et al., "Expression and targeting of the apoptosis inhibitor, survivin, in human melanoma," J. Invest. Dermatol., 113:1076-81 (1999).
Grossman et al., "Expression of the apoptosis inhibitor, survivin, in nonmelanoma skin cancer and gene targeting in a keratinocyte cell line," Lab. Invest., 79:1121-6 (1999).
Guillemard and Saragovi, "Novel approaches for targeted cancer therapy," Curr. Cancer Drug Targets, 4:313-326 (2004).
Hay et al., "Drosophila homologs of baculovirus inhibitor of apoptosis proteins function to block cell death," Cell 83:1253-62 (1995).
Hengartner, "Cell death and aging, molecular mechanisms of," Molecular Biology and Biotechnology, a Comprehensive Desk Reference (1995).
Holt et al., "Functional requirement of p23 and Hsp90 in telomerase complexes," Genes Dev., 13:817-826 (1999).
Hom et al., "Design and synthesis of statine-based cell-permeable peptidomimetic inhibitors of human β-secretase," J. Med. Chem., 46:1799-1802 (2003).

Isaacs et al., "Heat shock protein 90 as a molecular target for cancer therapeutics," Cancer Cell, 3:213-217 (2003).
Kabouridis, "Biological applications of protein transduction technology," Trends Biotechnol., 21:498-503 (2003).
Kelemen et al., "Selective in vivo inhibition of mitogen-activated protein kinase activation using cell-permeable peptides," J. Biol. Chem., 277:8741-8748 (2002).
Kim et al., "Advances in quantification and characterization of telomerase activity by the telomeric repeat amplification protocol (TRAP)," Nucleic Acids Res., 25:2595-97 (1997).
Li et al., "Control of apoptosis and mitotic spindle checkpoint by survivin," Nature 396:580-584 (1998).
Li et al., "Pleiotropic cell-division defects and apoptosis induced by interference with survivin function," Nat. Cell. Biol., 1:461-6 (1999).
Liston et al., "Suppression of apoptosis in mammalian cells by NAIP and a related family of IAP genes," Nature 379:349-53 (1996).
Lundberg and Johansson, "Positively charged DNA-binding proteins cause apparent cell membrane translocation," Biochem. Biophys. Res. Comm., 291:367-371 (2002).
Morris et al., "A peptide carrier for the delivery of biologically active proteins into mammalian cells," Nature Biotech., 19:1173-1176 (2001).
Muciimore et al., "Crystal structure and mutagenic analysis of the inhibitor-of-apoptosis protein survivin," Mol. Cell, 6:173-182 (2000).
O'Connor et al., "Regulation of apoptosis at cell division by p34$^{cdc2}$ phosphorylation of survivin," Proc. Natl. Acad. Sci. USA, 97:13103-7 (2000).
Okada and Mak, "Pathways of apoptotic and non-apoptotic death in tumour cells," Nat. Rev. Cancer, 4:592-603 (2004).
Plescia et al., "Rational design of shepherdin, a novel anticancer agent," Cancer Cell, 7:457-468 (2005).
Rothe et al., "The TNFR2-TRAF signaling complex contains two novel proteins related to baculoviral inhibitor of apoptosis proteins," Cell, 83:1243-52 (1995).
Roy et al., "The gene for neuronal apoptosis inhibitory protein is partially deleted in individuals with spinal muscular atrophy," Cell, 80:167-78 (1995).
Sawada et al., "Cytoprotective membrane-permeable peptides designed from the Bax-binding domain of Ku70," Nat. Cell Biol., 5:352-357 (2003).
Stebbins et al., "Crystal structure of an Hsp90-geldanamycin complex: targeting of a protein chaperone by an antitumor agent," Cell, 89:239-250 (1997).
Velculescu et al., "Analysis of human transcriptomes," Nat. Genet., 23:387-388 (1999).
Zou et al., "An APAF-1. cytochrome *c* multimeric complex is a functional apoptosome that activates procaspase-9," J. Biol. Chem., 274:11549-56 (1999).
U.S. Examiner Hugh Parker Young, USPTO Restriction Requirement in U.S. Appl. No. 11/187,230, mailed Nov. 1, 2006, 12 pages.
Fish & Richardson P.C., Response to Restriction Requirement dated Nov. 1, 2006 in U.S. Appl. No. 11/187,230, filed Dec. 4, 2006, 2 pages.
U.S. Examiner Hugh Parker Young, USPTO Non-Final Office Action in U.S. Appl. No. 11/187,230, mailed Feb. 6, 2007, 7 pages.
Fish & Richardson P.C., Amendment in Reply to Action dated Feb. 6, 2007 in U.S. Appl. No. 11/187,230, filed Aug. 6, 2007, 10 pages.
U.S. Examiner Maury A. Audet, USPTO Notice of Allowance in U.S. Appl. No. 11/187,230, mailed Oct. 16, 2007, 7 pages.
EPO Examiner Pinar Sirim, Extended European Search Report for App. Ser. No. EP 05 79 0290, dated Jun. 26, 2009, 14 pages.
Japan Patent Office, "English translation of the Notice of Reasons for Rejection," mailed on May 27, 2013, 8 pages.
U.S. Examiner Maury A. Audet, USPTO Restriction Requirement in U.S. Appl. No. 12/033,210, mailed Jul. 23, 2010, 7 pages.
U.S. Examiner Maury A. Audet, USPTO Non-Final Office Action in U.S. Appl. No. 12/033,210, mailed Oct. 21, 2010, 6 pages.
Fish & Richardson P.C., Reply to Action of Oct. 21, 2010, dated and filed Feb. 22, 2011, 6 pages.
U.S. Examiner Maury A. Audet, USPTO Non-Final Office Action in U.S. Appl. No. 12/033,210, mailed May 12, 2011, 7 pages.

(56) References Cited

OTHER PUBLICATIONS

Fish & Richardson P.C., Amendment in Reply to Action of May 12, 2011, dated and filed Nov. 14, 2011, 7 pages.
U.S. Examiner Maury A. Audet, USPTO Final Office Action in U.S. Appl. No. 12/033,210, mailed Feb. 3, 2012, 6 pages.
U.S. Examiner Maury A. Audet, USPTO Notice of Allowance and Fee(s) Due in U.S. Appl. No. 12/033,210, mailed Dec. 12, 2012, 10 pages.
Authorized Officer Masashi Honda, PCT Notification Concerning Transmittal of International Preliminary Report on Patentability, mailed Feb. 1, 2007, 5 pages.
Authorized Officer Roy Teller, PCT Notification of Transmittal of the International Search Report and the Written Opinion of the International Searching Authority, or the Declaration, mailed on Mar. 27, 2006, 10 pages.
AU Examiner Ricky Fling, Examiner's First Report in AU App. Ser. No. 2005269639, mailed on Oct. 7, 2010, 4 pages.
CA Examiner Julie Deschênes-Fury, Office Action in CA App. Ser. No. 2,574,183, mailed on Mar. 6, 2012, 6 pages.
The State Intellectual Property Office of the People'S Republic of China, The First Office Action in CN App. Ser. No. 200580032164.1, mailed on Aug. 21, 2009, 14 pages.
The Patent Office of the People'S Republic of China, the Second Office Action in CN App. Ser. No. 200580032164.1, mailed on Jul. 30, 2010, 10 pages.
The Patent Office of the People'S Republic of China, The Third Office Action in CN App. Ser. No. 200580032164.1, mailed on Apr. 20, 2011, 7 pages.
The Patent Office of the People'S Republic of China, The Fourth Office Action in CN App. Ser. No. 200580032164.1, mailed on Nov. 22, 2011 (4 pages).
Government of India Patent Office, First Examination Report on IN App. Ser. No. 1440/DELNP/2007 mailed on Sep. 17, 2012, 3 pages.
EP Primary Examiner Pinar Sirim, Communication pursuant to Article 94(3) EPC, mailed on Mar. 3, 2013, 9 pages.
Translation of the Notice of Reasons for Rejection in JP App. Ser. No. 2007-522704, mailed on Jan. 5, 2011, 3 pages.
Translation of the Notice of Reasons for Rejection in JP App. Ser. No. 2007-522704, mailed on Mar. 26, 2012, 5 pages.
EPO Examiner Pinar Sirim, Communication pursuant to Article 94(3) EPC for App. Ser. No. EP 05 790 290, dated Mar. 13, 2013, 9 pages.
Government of India Patent Office, Hearing Notice in Reference of in App. U.S. Appl. No. 1440/Delnp/2007, mailed on Feb. 17, 2014, 3 pages.
Japan Patent Office, English Translation of the Notice of Reasons for Rejection for JP Patent Application No. 2007-522704, mailed on May 27, 2013, 4 pages.
Lundberg et al., "A brief introduction to cell-penetrating peptides", J. Mol. Recognition, vol. 16:227-233 (2003).
Futaki et al., "Membrane permeability commonly shared among arginine-rich peptides", J. Mol. Recognition, vol. 16:260-264 (2003).
CA Examiner Qianfa (Kevin) Chen, Office Action in CA Appl. No. 2,574,183, mailed on Mar. 31, 2014, 3 pages.

* cited by examiner

WB: XIAP

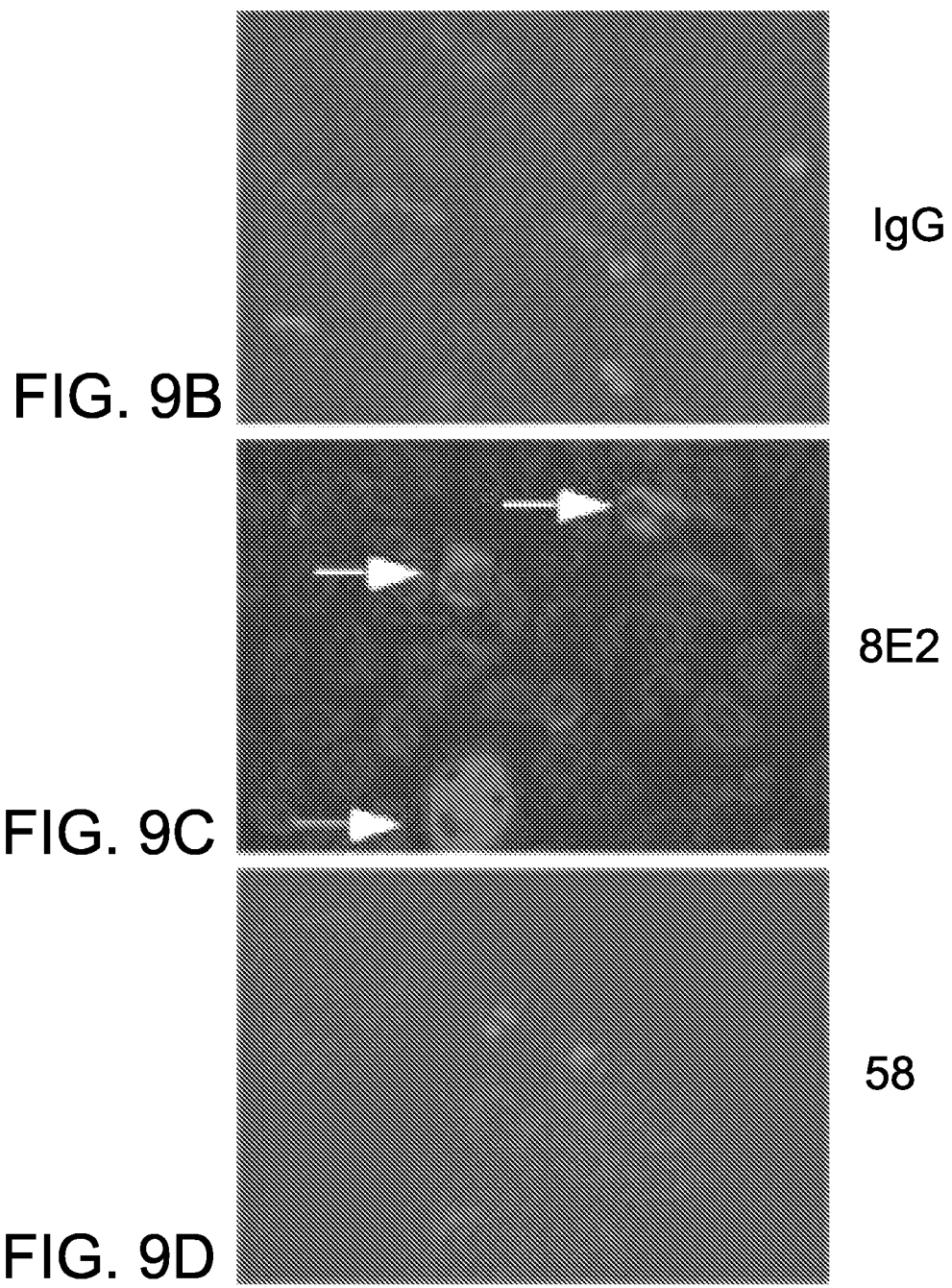

Forward Sequence, all L-amino acids
P31 Survivin 79-87:
Free-RQIKIWFQNRRMKWKKKHSSGCAFL-COOH (SEQ ID NO:19)

P33 Scrambled:
Free-RQIKIWFQNRRMKWKKSKLACFSHG-COOH (SEQ ID NO:25)

Survivin 79-83:
Free-RQIKIWFQNRRMKWKKKHSSG-COOH (SEQ ID NO:20)

Survivin 79-83 Scrambled:
Free-RQIKIWFQNRRMKWKKSGKHS-COOH (SEQ ID NO:28)

Retro-Inverso (Reverse sequence, all D-amino acids)
P3 survivin 79-87:
Biotin-X-KKWKMRRNQFWVKVQRLFACGSSHK-CONH$_2$

P4 Scrambled:
Biotin-X-KKWKMRRNQFWVIWQRGHSFCALKS-CONH$_2$

FIG. 21

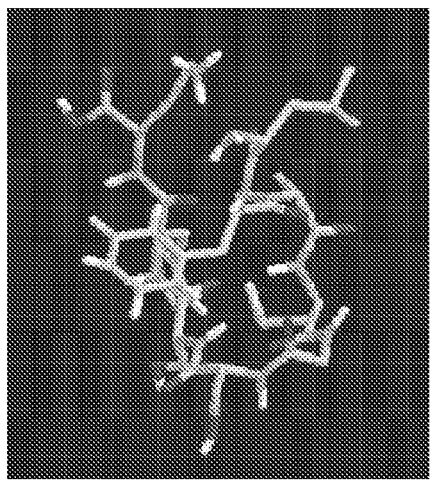 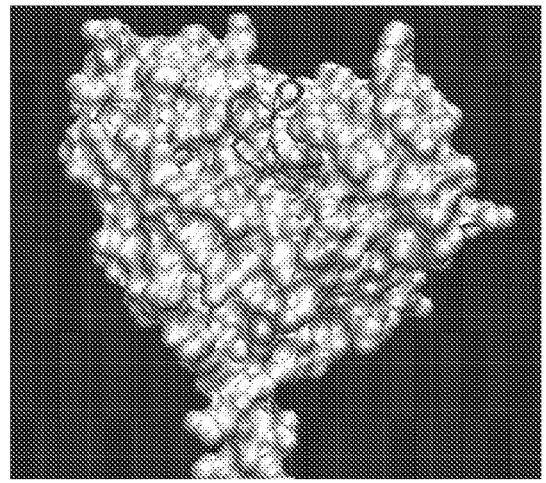
FIG. 25A              FIG. 25B
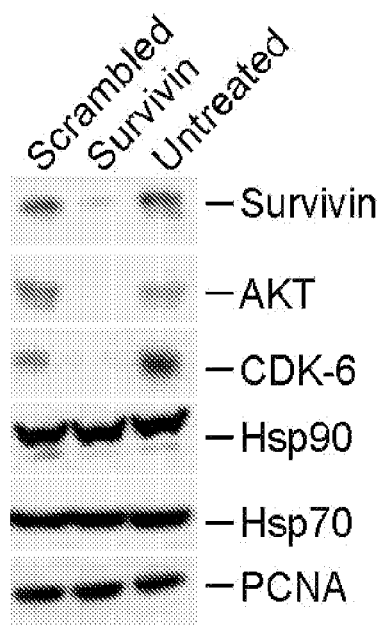 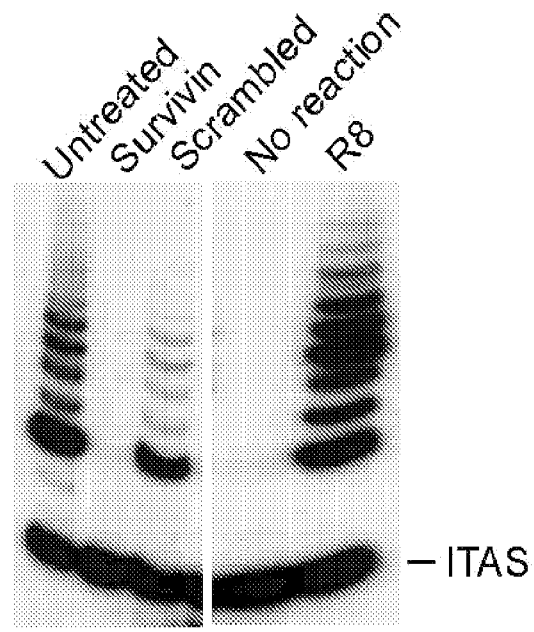
FIG. 26A              FIG. 26B

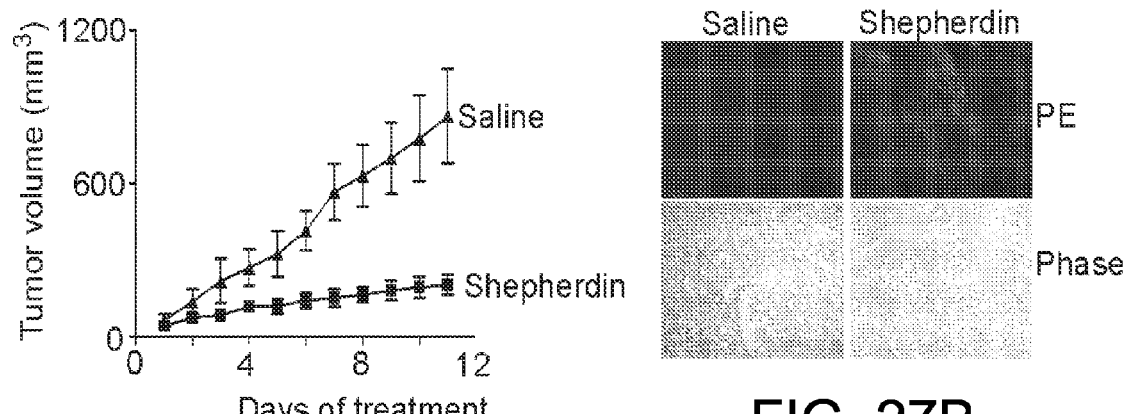
FIG. 27A
FIG. 27B
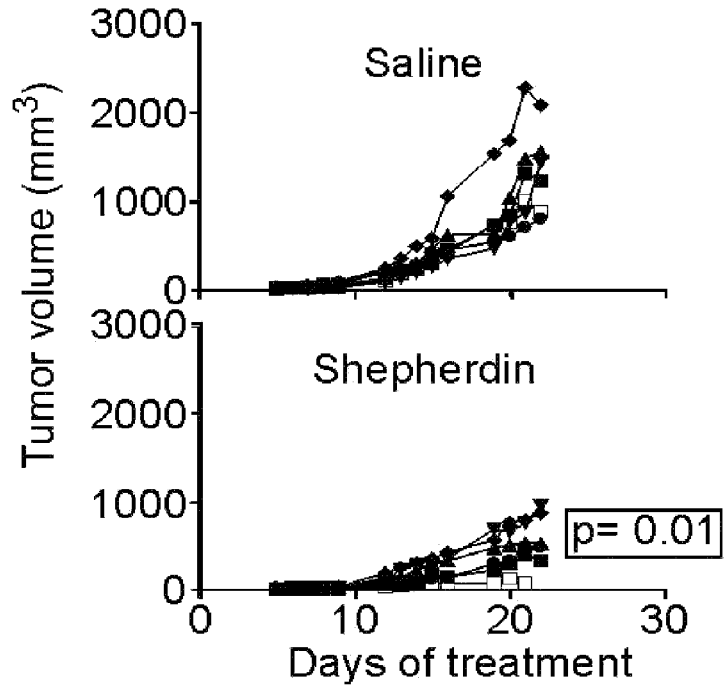
FIG. 28

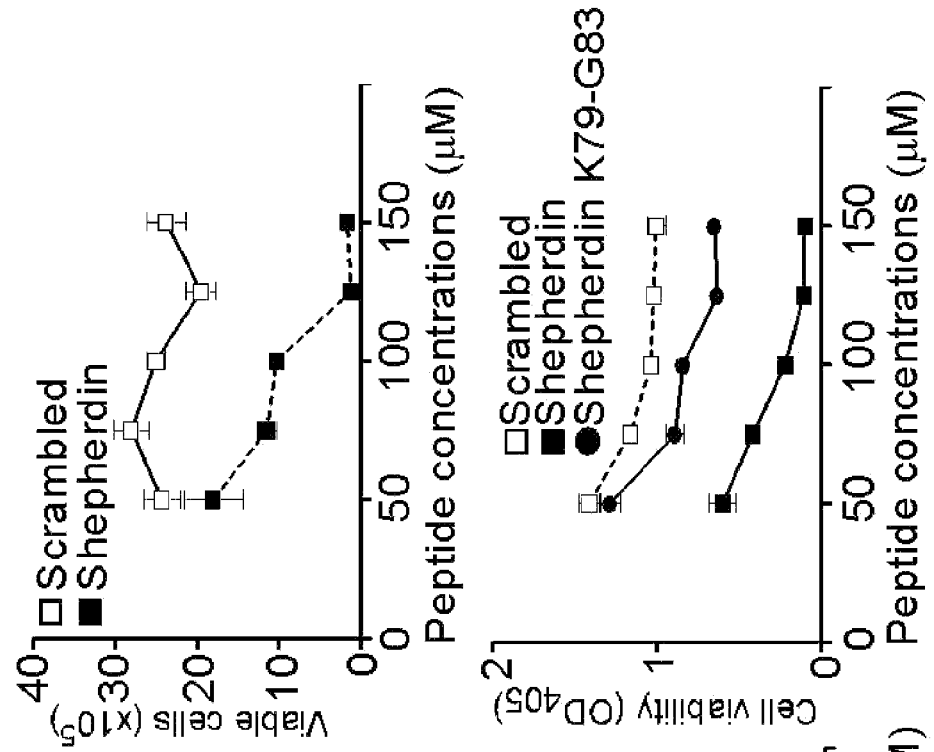
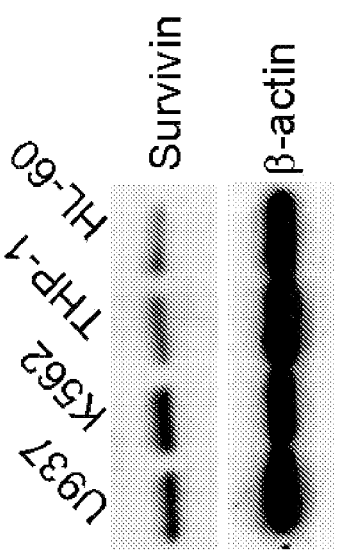
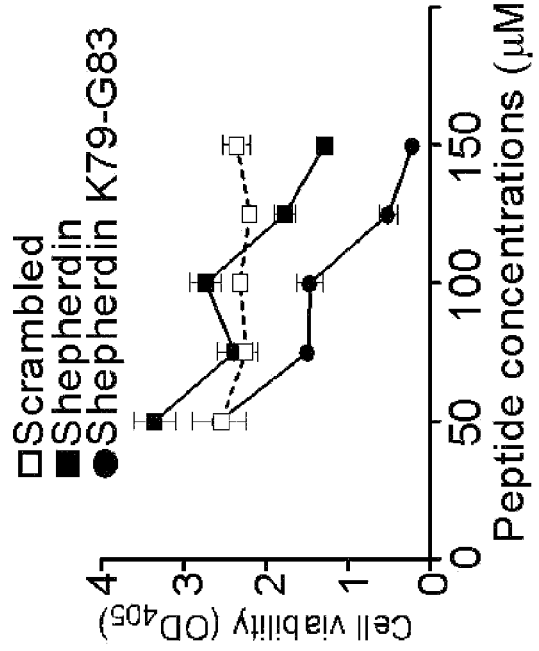
FIG. 29A
FIG. 29B
FIG. 29C
FIG. 29D

US 9,035,024 B2

COMPOUNDS THAT INHIBIT HSP90 PROTEIN-PROTEIN INTERACTIONS WITH IAP PROTEINS

CROSS-REFERENCE TO RELATED APPLICATIONS

This application is a continuation application of U.S. patent application Ser. No. 12/033,210, filed Feb. 19, 2008 (issued as U.S. Pat. No. 8,420,777), which is a divisional application of U.S. patent application Ser. No. 11/187,230, filed on Jul. 22, 2005 (issued as U.S. Pat. No. 7,342,093), which claims the benefit of the filing date of U.S. Provisional Patent Application Ser. No. 60/590,584, filed on Jul. 23, 2004. The contents of these prior applications are hereby incorporated by reference in their entirety.

STATEMENT AS TO FEDERALLY SPONSORED RESEARCH

This invention was made with support from the National Institute of Health under grant numbers 2R01CA078810, 5R01HL54131, and 5R01CA90917, therefore the government has certain rights in the invention.

TECHNICAL FIELD

This invention relates to compounds, e.g., peptides and peptide derivatives, that inhibit protein-protein interactions between the Heat-shock protein Hsp90 and Inhibitor of Apoptosis (IAP) proteins, e.g., Survivin, XIAP, cIAP1, or cIAP2, and methods of identifying and using such compounds.

BACKGROUND

Tumor cells exhibit an enhanced ability to survive and proliferate in highly unfavorable environments. For example, tumor cells down-regulate many of the cellular pathways that prevent normal (i.e., non-cancerous) cells from dividing in a hostile environment. Tumor cells also inactivate apoptotic pathways that bring about the cell death of many normal tissues under adverse conditions. Tumor cells up-regulate pathways required to maintain active proliferation. For example, many tumor cells activate the cellular stress-response pathway that allows tumor cells to synthesize and maintain the protein machinery they need to continue proliferating. Activated stress response in tumors includes up-regulation of heat-shock proteins (Hsps), which are ATPase-directed molecular chaperones. In particular, Hsp90 is upregulated in many cancerous tissues. Hsp90 controls the balance between folding/maturation and proteasomal destruction of a restricted number of client proteins, some of which are involved in signal transduction and cell proliferation.

Members of the Inhibitor of Apoptosis (IAP) family of proteins are characterized by one or more Baculovirus IAP repeat domains. These proteins were first identified by their ability to enhance baculovirus propagation by preventing the defensive apoptosis of host insect cells. Survivin is a small 16.5 kDa mammalian member of the IAP family that is broadly expressed in embryonic and fetal organs, but becomes virtually undetectable in most terminally differentiated normal tissue. Survivin is highly expressed, however, in a variety of tumor tissues, and is thought to be involved in the mechanism by which many tumor cells avoid cell death and continue to proliferate.

SUMMARY

The present invention is based, at least in part, on the discovery of specific regions, e.g., binding domains or motifs, of the Inhibitor of Apoptosis (IAP) proteins, including Survivin, cIAP1, cIAP2, and XIAP, that mediate protein-protein interactions with the Heat-shock protein Hsp90. These regions are identified and characterized as mediating the anti-apoptotic effects of these IAP proteins, e.g., Survivin. Methods are provided for identifying compounds that disrupt Hsp90 interactions with IAP proteins. Compounds, e.g., peptides, peptide derivatives, peptidomimetics, and small molecules, that inhibit protein-protein interactions between Hsp90 and an IAP protein, e.g., Survivin, are useful in the treatment of conditions associated with unwanted cellular proliferation, such as cancer.

In one aspect, the invention includes an isolated compound that inhibits protein-protein interactions between Hsp90 and Survivin. In various embodiments, such compounds are isolated Survivin peptides that include His-Ser-Ser-Gly-Cys (SEQ ID NO:2) or Lys-His-Ser-Ser-Gly (SEQ ID NO:26), and are for example, 50 or fewer, 45 or fewer, 40 or fewer, 35 or fewer, 30 or fewer, 25 or fewer, 20 or fewer, 15 or fewer, 12 or fewer, 10 or fewer, 9 or fewer, 8 or fewer, 7 fewer, 6 or fewer, or 5 amino acids in length. Exemplary Survivin peptides include His-Ser-Ser-Gly-Cys (SEQ ID NO:2), Lys-His-Ser-Ser-Gly-Cys-Ala-Phe-Leu-Ser-Val-Lys (SEQ ID NO:3), Ile-Asp-Asp-His-Lys-Lys-His-Ser-Ser-Gly-Cys-Ala-Phe-Leu (SEQ ID NO:4), and Lys-Lys-His-Ser-Ser-Gly-Cys-Ala-Phe-Leu (SEQ ID NO:5).

In some embodiments, an isolated Survivin peptide is linked to a heterologous sequence, e.g., a peptide internalization sequence (e.g., a Tat, Antennapedia, vβRR, transportin, or transportan sequence) that enhances the cell permeability of the compound. An exemplary Antennapedia peptide internalization sequence is RQKIWFQNRRMKWKK; (SEQ ID NO:29). In certain embodiments, the compound is a peptidomimetic of a Survivin peptide disclosed herein, for example the compound can be a retro-peptide, an inverso peptide, and/or can include one or more artificial amino acid analogs. Peptidomimetics can also be linked to a heterologous sequence, e.g., a peptide internalization sequence. Peptide derivatives include, e.g., peptides linked to a peptide internalization sequence and peptidomimetics.

Also provided are nucleic acids encoding the Survivin peptides and peptide derivatives disclosed herein, as well as recombinant cells that include these nucleic acids. In another aspect, disclosed herein are anti-Survivin antibodies, e.g., intrabodies, that bind to peptides or peptide derivatives disclosed herein. Examples of such antibodies include those produced by administering a peptide or peptide derivative disclosed herein to an animal capable of generating antibodies.

In a different aspect, the invention also provides methods of making small molecule inhibitors of tumor growth. Typically, these methods include providing a lead compound, e.g., a Survivin peptide or peptide derivative disclosed herein, employing medicinal chemistry to develop candidate compounds that are structurally similar to the lead compound, and optionally determining whether the candidate compound inhibits tumor cell growth. The candidate compound can be formulated into a pharmaceutical carrier, thereby preparing a small molecule inhibitor of tumor growth.

In another aspect, the invention includes screening assays for identifying candidate apoptosis-inducing compounds. Typically, these assays include: (i) mixing together a test compound, an Hsp90 peptide, and an IAP peptide (e.g., Survivin) under conditions and for a time sufficient to enable an interaction, e.g., binding, and (ii) detecting whether the test compound inhibits protein-protein interactions between the Hsp90 peptide and the IAP peptide. A test compound that inhibits protein-protein interactions between an Hsp90 peptide and an IAP peptide (e.g., a Survivin peptide) is a candidate apoptosis-inducing compound.

In yet another aspect, the invention features screening assays for identifying candidate apoptosis-inducing compounds. Typically, these assays include: (i) administering the compound to a cell (e.g., a tumor cell in vivo or a tumor cell in culture) expressing Hsp90 and an IAP peptide (e.g., a Survivin peptide) and (ii) measuring the interactions, e.g., binding, between the Hsp90 peptide and the IAP peptide (e.g., Survivin). A compound that reduces the interaction between the Hsp90 peptide and the IAP peptide (e.g., Survivin) is a candidate apoptosis-inducing compound.

In still another aspect, the invention features screening assays for identifying apoptosis inducing agents. Typically, these assays include: contacting a tumor cell with a candidate apoptosis-inducing compound identified by a method disclosed herein, and detecting the presence or absence of one or more markers of apoptosis. A candidate apoptosis-inducing compound that causes a cell to exhibit one or more apoptosis markers is an apoptosis inducing agent.

Also described are screening assays for identifying inhibitors of tumor growth. Typically, these assays include: contacting one or more tumor cells with a candidate apoptosis-inducing compound identified by a method disclosed herein; and measuring the proliferation of the tumor cell(s). A candidate apoptosis-inducing compound that inhibits proliferation of the tumor cell(s), relative to the proliferation of one or more tumor cells not contacted by the compound, is an inhibitor of tumor growth.

In a different aspect, the invention also includes methods for treating a tumor in a subject by (i) identifying a subject in need of treatment for a tumor, and (ii) administering to the subject a pharmaceutical composition of any compound disclosed herein that inhibits protein-protein interactions between Hsp90 and Survivin. A pharmaceutical composition used in a method of treating a tumor in a subject can include, e.g., a Survivin peptide (or peptide derivative) and/or an antibody to Survivin that inhibits protein-protein interactions between Hsp90 and Survivin. In another aspect, a method of treating a tumor in a subject includes: (i) identifying a subject in need of treatment for a tumor, and (ii) administering to the subject a pharmaceutical composition comprising a compound or agent identified by the methods disclosed herein.

The invention also features methods of inhibiting an interaction between Hsp90 and an IAP polypeptide in a cell, by introducing an effective amount of a compound or pharmaceutical composition described herein into the cell.

The terms "protein," "polypeptide," and "peptide" refer to any chain of amino acids, regardless of length or post-translational modification (e.g., glycosylation or phosphorylation) and are used interchangeably herein unless otherwise indicated.

The terms "isolated peptide" and "isolated nucleic acid" include peptide molecules and nucleic acid molecules, respectively, substantially free from other peptides and nucleic acids present in a natural source (if any) of the molecules. An example of an isolated peptide is a peptide free from a substantial amount of other peptides and materials present in a cell. In a different example, an isolated nucleic acid can be free of sequences that flank the endogenous nucleic acid (i.e., sequences located at the 5' and/or 3' ends of the nucleic acid) in the genomic DNA of the organism from which the nucleic acid is obtained or derived (e.g., synthesized) from. Isolated peptides and nucleic acids can be synthesized in vitro and/or isolated from natural sources.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Hsp90 peptide" as used herein, refers to a full-length Hsp90, or a peptide thereof, that binds to an IAP protein, such as Survivin, cIAP1, cIAP2, and XIAP.

"IAP peptide" as used herein, refers to a full-length IAP protein, or a peptide thereof, that binds to Hsp90.

"Survivin peptide" as used herein, refers to full-length Survivin or a peptide of Survivin that binds to Hsp90.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DESCRIPTION OF DRAWINGS

FIG. 9B, FIG. 9C, and FIG. 9D are a series of three micrographs at 400× magnification, each showing cells that were loaded with the indicated antibody. FIG. 9B shows cells loaded with a control IgG. FIG. 9C shows cells loaded with mAb 8E2. FIG. 9D shows cells loaded with mAb 58. Cells loaded with mAb 8E2 induced multinucleation (a characteristic of mitotic defects associated with loss or deregulation of Survivin function) in cells marked by arrows (FIG. 9C).

FIG. 21 is a list of cell permeable Survivin peptide derivatives and corresponding scrambled controls. Wild-type (Forward) Survivin amino acid side chain sequence and the corresponding scrambled sequence are underlined, as are their respective "retro-inverso" sequences. "X" in the sequences indicates an EAHX, hexanoic acid spacer.

FIG. 25A and FIG. 25B are molecular models of the survivin peptide. FIG. 25A depicts an energy minimized predicted structure of the retro-inverso survivin K79-L87 sequence showing a β-turn dominant conformation in solution. FIG. 25B depicts docking of the retro-inverso survivin K79-L87 peptide in the ATPase pocket of Hsp90 as predicted by molecular modeling.

FIG. 26A is a reproduction of an immunoblot for Survivin, AKT, CDK-6, Hsp90, Hsp70, and PCNA in cells treated with the Survivin peptide.

FIG. 26B is a reproduction of the results of a TRAP assay to detect telomerase activity in immunoprecipitates of cells treated with the survivin peptide. In the lane labeled as no reaction, no cellular extracts were added. R8, external quantitative standard; ITAS, internal amplification standard.

FIG. 27A is a graph depicting tumor volume over eleven days of treatment with saline or Survivin peptide.

FIG. 27B is an immunofluorescence micrograph of tumor cells. Fluorescence indicates the presence of Survivin peptide.

FIG. 28 is a graph depicting tumor growth in mice carrying tumors from MCF-7 cells that were injected intraperitoneally with saline or Survivin P3 peptide (50 mg/kg/daily) (6 animals/group) for the indicated time intervals. Lines correspond to individual animals. FIG. 29A is a reproduction of an immunoblot depicting levels of Survivin in AML cells.

FIGS. 29B-29D are graphs depicting killing of AML cells by Survivin peptides. FIG. 29B depicts survivin peptide activity in HL-60 cells, measured by Trypan blue exclusion. FIGS. 29C and 29D depict killing, as measured using MTT, of HL-60 (FIG. 29C) or THP-1 (FIG. 29D) cells by full length Survivin peptide (SEQ ID NO:19), Survivin peptide K79-G83 (SEQ ID NO:20), or scrambled peptide (SEQ ID NO:25 and SEQ ID NO:28).

DETAILED DESCRIPTION

Figure 1A:
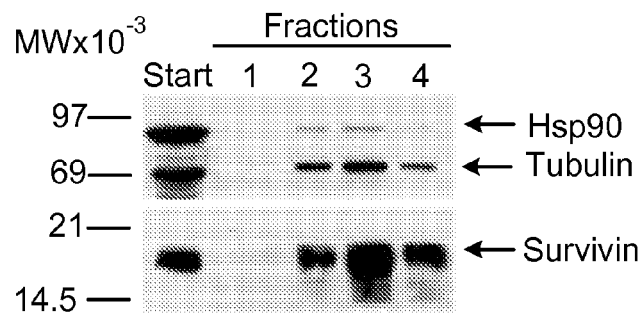
FIG. 1A is an image of an immunoblot of cell lysate proteins that bound a column of Sepharose coupled to anti-Survivin antibody. After extensive washing of the column bound proteins were eluted, and proteins in eluted fractions were identified using the indicated antibodies.

The present invention is based, in part, on the discovery of specific regions of the Inhibitor of Apoptosis (IAP) proteins, including Survivin, cIAP1, cIAP2, and XIAP, that mediate protein-protein interactions with the Heat-shock protein Hsp90. Hsp90 interactions with IAP proteins mediate suppression of apoptosis in tumor cells. Disclosed herein are peptides and peptide derivatives of IAP proteins that can be used as inhibitors of Hsp90-IAP interactions and modulators of apoptosis in tumor cells. For example, novel Survivin peptides are disclosed that inhibit Hsp90-Survivin interactions and induce apoptosis in tumor cells in vitro and in vivo. Also provided are screening methods for identifying compounds that inhibit Hsp90-IAP, e.g., Hsp90-Survivin, protein-protein interactions, and induce apoptosis in tumor cells. The rational design of Survivin peptides is described in Plescia et al., *Cancer Cell,* 7:457-468 (May 2005), which is incorporated herein by reference in its entirety.

Survivin Peptides

The Survivin peptides and peptide derivatives disclosed herein share a core Hsp90 binding sequence motif of SEQ ID NO:2 (His Ser Ser Gly Cys). This core Hsp90 binding motif is located within the single Baculovirus IAP repeat (BIR) domain of Survivin protein. More specifically, the motif corresponds to amino acid residues at position 80-84 of full-length Survivin (SEQ ID NO:1). Peptides including this motif, and peptide derivatives thereof, can (a) bind to the N-terminal ATPase domain of Hsp90 (the "ATP pocket") and (b) inhibit Hsp90-Survivin protein-protein interactions in vitro and in vivo.

The terms Survivin peptide and Survivin peptide derivative, as used herein, refer to peptides that include less than the complete amino acid sequence of a functional Survivin protein that prevents apoptosis. Survivin peptides and peptide derivatives disclosed herein inhibit Hsp90-Survivin interactions in vitro and/or in vivo, thereby inducing apoptosis in tumor cells in vitro and/or in vivo.

The full-length human, wild type Survivin polypeptide has the following amino acid sequence:

```
                                            (SEQ ID NO: 1)
MGAPTLPPAWQPFLKDHRISTFKNWPFLEGCACTPERMAEAGFIHCPTE

NEPDLAQCFFCFKELEGWEPDDDPIEEHKKHSSGCAFLSVKKQFEELTL

GEFLKLDRERAKNKIAKETNNKKKEFEETAKKVRRAIEQLAAMD
```

The full-length human, wild type Hsp90 polypeptide has the following amino acid sequence:

```
                                            (SEQ ID NO: 21)
MPEETQTQDQPMEEEEVETFAFQAEIAQLMSLIINTFYSNKEIFLRELI

SNSSDALDKIRYETLTDPSKLDSGKELHINLIPNKQDRTLTIVDTGIGM

TKADLINNLGTIAKSGTKAFMEALQAGADISMIGQFGVGFYSAYLVAEK

VTVITKHNDDEQYAWESSAGGSFTVRTDTGEPMGRGTKVILHLKEDQTE

YLEERRIKEIVKKHSQFIGYPITLFVEKERDKEVSDDEAEEKEDKEEEK

EKEEKESEDKPEIEDVGSDEEEEKKDGDKKKKKKIKEKYIDQEELNKTK
```

-continued

```
PIWTRNPDDITNEEYGEFYKSLTNDWEDHLAVKHFSVEGQLEFRALLFV

PRRAPFDLFENRKKKNNIKLYVRRVFIMDNCEELIPEYLNFIRGVVDSE

DLPLNISREMLQQSKILKVIRKNLVKKCLELFTELAEDKENYKKFYEQF

SKNIKLGIHEDSQNRKKLSELLRYYTSASGDEMVSLKDYCTRMKENQKH

IYYITGETKDQVANSAFVERLRKHGLEVIYMIEPIDEYCVQQLKEFEGK

TLVSVTKEGLELPEDEEEKKKQEEKKTKFENLCKIMKDILEKKVEKVVV

SNRLVTSPCCIVTSTYGWTANMERIMKAQALRDNSTMGYMAAKKHLEIN

PDHSIIETLRQKAEADKNDKSVKDLVILLYETALLSSGFSLEDPQTHAN

RIYRMIKLGLGIDEDDPTADDTSAAVTEEMPPLEGDDDTSRMEEVD
```

Novel Survivin peptides also include peptides flanked by a different number of amino acid residues on the amino side of the pentamer sequence as on the carboxyl flank of the pentamer, e.g., the present invention includes peptides with zero, one, two, three, four, five, six, seven, eight, nine, ten, eleven, twelve, thirteen, fourteen, fifteen, or sixteen amino acids flanking the amino side of the pentamer sequence located of His 80 to Cys 84 in SEQ ID NO:1 and zero, one, two, three, four, five, six, seven, eight, nine, ten, eleven, twelve, thirteen, fourteen, fifteen, or sixteen amino acids flanking the carboxyl side of the pentamer sequence located of His 80 to Cys 84 in SEQ ID NO:1, wherein the number of amino acids flanking the amino side of the pentamer sequence is different from the number of amino acids flanking the carboxyl side of the pentamer sequence. Exemplary Survivin peptides are listed in Table 1.

TABLE 1

Exemplary Survivin peptides

| | |
|---|---|
| SEQ ID NO: 2 | His Ser Ser Gly Cys |
| SEQ ID NO: 3 | Lys His Ser Ser Gly Cys Ala Phe Leu Ser Val Lys |
| SEQ ID NO: 4 | Ile Asp Asp His Lys Lys His Ser Ser Gly Cys Ala Phe Leu |
| SEQ ID NO: 5 | Lys Lys His Ser Ser Gly Cys Ala Phe Leu |
| SEQ ID NO: 6 | Lys His Ser Ser Gly Cys |
| SEQ ID NO: 7 | His Ser Ser Gly Cys Ala |
| SEQ ID NO: 8 | Lys His Ser Ser Gly Cys Ala |
| SEQ ID NO: 9 | Lys Lys His Ser Ser Gly Cys |
| SEQ ID NO: 10 | His Ser Ser Gly Cys Ala Phe |
| SEQ ID NO: 22 | His Lys Lys His Ser Ser Gly Cys Ala Phe Leu Ser Val Lys Lys |
| SEQ ID NO: 24 | Lys His Ser Ser Gly Cys Ala Phe Leu |

One novel Survivin peptide disclosed herein is the pentamer peptide His-Ser-Ser-Gly-Cys of SEQ ID NO:2 corresponding to residues His 80 to Cys 84 of SEQ ID NO:1. This pentamer sequence can be expanded to include one or more amino acids that correspond to the amino acids that flank (i.e., immediately precede or follow the pentamer sequence with no intervening amino acids) the pentamer sequence in full-length Survivin. For example, a novel peptide disclosed herein is the 9-mer of SEQ ID NO:24 (Lys His Ser Ser Gly Cys Ala Phe Leu) that contains residues Lys 79 to Leu 87 of SEQ ID NO:1. Another novel peptide is the 10-mer of SEQ ID NO:5 (Lys Lys His Ser Ser Gly Cys Ala Phe Leu) that contains residues Lys 78 to Leu 87 of SEQ ID NO:1. Another novel peptide is the 12-mer of SEQ ID NO:3 (Lys His Ser Ser Gly Cys Ala Phe Leu Ser Val Lys) that contains residues Lys 79 to Cys 90 of SEQ ID NO:1. Another novel peptide disclosed herein is the 14-mer of SEQ ID NO:4 (Ile Asp Asp His Lys Lys His Ser Ser Gly Cys Ala Phe Leu) that contains residues Ile 74-Leu 87 of SEQ ID NO:1.

Novel peptides provided herein include the one, two, three, four, five six, seven, eight, nine, ten, eleven, twelve, thirteen, fourteen, fifteen, or sixteen amino acids flanking one (amino or carboxyl) or both sides of the pentamer sequence of His 80 to Cys 84 in SEQ ID NO:1.

Novel Survivin peptides disclosed herein include the peptides of SEQ ID NOs: 3-5. Note that the Lys immediately N-terminal to the pentamer motif (i.e. corresponding to Lys 79 of SEQ ID NO:1) can be replaced with both conservative and some non-conservative amino acid substitutions. See, e.g., Example 10. More generally, in Survivin peptides disclosed herein, conservative amino acid substitutions can be made for one or more amino acids outside of the core pentamer sequence corresponding to His 80 to Cys 84 in SEQ ID NO:1. In addition, one or two of the amino acids at either end of SEQ ID NO:2 can be replaced by conservative amino acid substitutions or deleted. Thus, His-Ser-Ser (SEQ ID NO:11), Ser-Ser-Gly (SEQ ID NO:12), Ser-Gly-Cys (SEQ ID NO:13), His-Ser-Ser-Gly (SEQ ID NO:14), Ser-Ser-Gly-Cys (SEQ ID NO:15), and Lys-His-Ser-Ser-Gly (SEQ ID NO:26) are also Survivin peptides.

In addition, random amino acids, or stretches of random amino acids, can be connected on either or both sides of SEQ ID NO:2 or SEQ ID NO:26 to form a Survivin polypeptide.

Other Survivin peptides that can be used in methods disclosed herein include polypeptides, e.g., those identified in methods disclosed herein, that bind to Hsp90 and induce apoptosis in tumor cells. For example, Survivin peptides include the Baculovirus IAP repeat domain, and fragments thereof that bind to Hsp90 and induce apoptosis in tumor cells.

IAP Peptides

Other Inhibitors of Apoptosis Proteins interact with Hsp90, including cIAP1 (Entrez Accession No.: NP_001156), cIAP2 (Entrez Accession No.: NP_001157), and XIAP (Entrez Accession No.: NP_001158). See, e.g., Deveraux and Reed, *Genes and Dev.*, 13:239-252 (1999). These IAP proteins contain at least one Baculovirus IAP repeat domain that mediates Hsp90 interactions, as disclosed herein. For example, the first BIR domain of XIAP (BIR1), corresponding approximately to amino acids 1-123 of full length XIAP, mediates Hsp90-XIAP binding interactions.

Peptides corresponding to one or more BIR domains in these IAP proteins, or Hsp90-binding fragments thereof, can therefore be used in the methods disclosed herein to inhibit Hsp90-IAP protein interactions and thereby modulate apoptosis of a tumor cell. For example, the first BIR domain of XIAP, cIAP1, or cIAP2 can be used to inhibit protein-protein interactions between Hsp90 and XIAP, cIAP1, or cIAP2. In other embodiments, a peptide corresponding to a fragment of an IAP protein's BIR domain that binds Hsp90 can be used to disrupt Hsp90-IAP protein interactions.

An exemplary first BIR domain of XIAP includes the sequence:

(SEQ ID NO: 16)
RLKTFANFPSGSPVSASTLARAGFLYTGEGDTVRCFSCHAAVDRWQYGD

SAVGRHRKVSPNCRFIN

An exemplary first BIR domain of cIAP1 includes the sequence:

(SEQ ID NO: 17)
RMSTYSTFPAGVPVSERSLARAGFYYTGVNDKVKCFCCGLMLDNWKRGD

SPTEKHKKLYPSCRFVQ

An exemplary first BIR domain of cIAP2 includes the sequence:

(SEQ ID NO: 18)
RMSTYSTFPAGVPVSERSLARAGFYYTGVNDKVKCFCCGLMLDNWKLGD

SPIQKHKQLYPSCSFIQ

Peptide Derivatives

Modified versions of peptides disclosed herein are referred to as "peptide derivatives," and they can also be used in the new methods. For example, peptide derivatives of a peptide can be used instead of that peptide in screens and therapeutic methods described herein.

1. Peptide Internalization Sequence

Peptides of Survivin that bind to Hsp90 and induce apoptosis in tumor cells can be modified by attachment of a cell penetrating peptide sequence, sometimes referred to as a carrier domain or protein transduction domain. Examples of cell penetrating peptide sequences are described in Hom et al., *J Med. Chem.*, 46:1799 (2003) and Bonny et al., *Diabetes*, 50:77-82 (2001).

For example, peptides and fragments disclosed herein can be attached to an Antennapedia carrier sequence corresponding to a sequence found on the third α-helix of the Antennapedia carrier sequence (Gratton et al., *Cancer Cell*, 4:31, (2003)). Other examples of cell penetrating sequences to which peptides and fragments disclosed herein can be attached include the TAT protein sequence from HIV-1 (Chen et al., *Proc. Natl. Acad. Sci. USA*, 96:4325 (1999) Kelemen et al., *J. Biol. Chem.*, 277:8741-8748, (2002). Yet other examples include VP22 protein from Herpes Simplex virus (Lundberg and Johansson, *Biochem. Biophys. Res. Comm.*, 291:367-371 (2002)) and the Pep-1 peptide carrier (Morris et al., *Nature Biotech.*, 19:1173-1176 (2001)). Polypeptides that include peptides and fragments with cell penetrating peptide sequences can be produced by standard techniques, such as chemical synthesis, or expressed from a nucleic acid that encodes the polypeptide. Exemplary peptides that include an internalization sequence include RQIKIWFQNRRMKWKK KHSSGCAFL (SEQ ID NO:19) and RQIKIWFQNRRMK-WKKKHSSG (SEQ ID NO:20), wherein the underlined sequence corresponds to a sequence of Survivin.

2. Peptidomimetics

Peptides disclosed herein can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., *J. Biol. Chem.*, 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β³-amino acids"), phosphorous analogs of amino acids, such as ∀-amino phosphonic acids and ∀-amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules. Exemplary Survivin retro-inverso peptidomimetics include LFACGSSHK, CGSSH, GSSHK, KKWKMRRNQF-WVKVQRLFACGSSHK, KKWKMRRNQF-WVKVQRCGSSH, and KKWKMRRNQF-WVKVQRGSSHK wherein the sequences include all D-amino acids. These sequences can be modified, e.g., by biotinylation of the amino terminus and amidation of the carboxy terminus.

Nucleic Acids, Vectors, and Host Cells

In one aspect, the invention includes nucleic acids encoding a peptide or modified peptide that disrupts Hsp90-IAP protein interactions. For example, the invention includes nucleic acids encoding novel peptides that include the one, two, three, four, five, six, seven, eight, nine, ten, eleven, twelve, thirteen, fourteen, fifteen, or sixteen amino acids flanking one or both (amino or carboxyl) sides of the pentamer sequence SEQ ID NO:2 (His 80 to Cys 84 of SEQ ID NO:1).

The new nucleic acids include nucleic acid sequences encoding the peptides of SEQ ID NOs: 2, 3, 4, or 5. Nucleic acids disclosed herein also include nucleic acids encoding certain modified Survivin peptides, e.g., retro-Survivin peptides, Survivin peptides linked to a cellular internalization (carrier) sequence, and retro-Survivin peptides linked to a carrier sequence.

The nucleic acids can also encode peptides of an IAP protein family member that disrupts Hsp90 protein-protein interactions with XIAP, cIAP1, or cIAP2. For example, the present invention includes nucleic acids encoding BIR1, Met 1-Ser 123 of XIAP protein. Nucleic acids described herein can encode any of the peptides identified by the methods disclosed herein that disrupt Hsp90 protein-protein interactions with XIAP, cIAP1, or cIAP2. The nucleic acids disclosed herein also include nucleic acids encoding modified versions of peptides that disrupt Hsp90 protein-protein interactions with XIAP, cIAP1, or cIAP2, e.g., retro peptides, peptides linked to a cellular internalization (carrier) sequence, and retro peptides linked to a carrier sequence.

Nucleic acids disclosed herein also include both RNA and DNA, including genomic DNA and synthetic (e.g., chemically synthesized) DNA. Nucleic acids can be double-stranded or single-stranded. Nucleic acids can be synthesized using oligonucleotide analogs or derivatives (e.g., inosine or phosphorothioate nucleotides). Such oligonucleotides can be used, for example, to prepare nucleic acids with increased resistance to nucleases.

Also included in the invention are genetic constructs (e.g., vectors and plasmids) that include a nucleic acid encoding a peptide described herein operably linked to a transcription and/or translation sequence that enables expression of the peptide, e.g., expression vectors. A selected nucleic acid, e.g., a DNA molecule encoding a peptide described herein, is "operably linked" to another nucleic acid molecule, e.g., a promoter, when it is positioned either adjacent to the other molecule or in the same or other location such that the other molecule can direct transcription and/or translation of the selected nucleic acid.

Also included in the invention are various engineered cells, e.g., transformed host cells, which contain a nucleic acid disclosed herein. A transformed cell is a cell into which (or into an ancestor of which) has been introduced, by means of recombinant DNA techniques, a nucleic acid encoding an a peptide described herein that binds HSP-90 and/or induces apoptosis in a tumor cell. Both prokaryotic and eukaryotic cells, e.g., mammalian cells (e.g., tumor cell), yeast, fungi, and bacteria (such as *Escherichia coli*), can be host cells. An engineered cell exemplary of the type included in the invention is a tumor cell that expresses a Survivin peptide, e.g., as described in the Examples section, below.

Methods of Identifying Compounds that Inhibit Hsp90 Protein-Protein Interactions with Survivin, XIAP, cIAP1, or cIAP2

In some aspects, the invention provides methods for identifying compounds, e.g., small organic or inorganic molecules (M.W. less than 1,000 Da), oligopeptides, oligonucleotides, carbohydrates, and antibodies capable of inhibiting Hsp90 protein-protein interactions with Survivin, XIAP, cIAP1, or cIAP2 and thereby inhibiting the anti-apoptotic activity of Survivin, XIAP, cIAP1, or cIAP2, respectively. These small molecules, oligopeptides, and oligonucleotides are useful in treatments of conditions characterized uncontrolled cellular proliferation and inactivation of apoptotic mechanisms, e.g., cancer.

Libraries of Test Compounds

In certain embodiments, screens disclosed herein utilize libraries of test compounds. As used herein, a "test compound" can be any chemical compound, for example, a macromolecule (e.g., a polypeptide, a protein complex, glycoprotein, polysaccharide, or a nucleic acid) or a small molecule (e.g., an amino acid, a nucleotide, or an organic or inorganic compound). A test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of test compounds include peptides, peptidomimetics (e.g., peptoids, retro-peptides, inverso peptides, and retro-inverso peptides), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., Gordon et al., *J. Med. Chem.*, 37:1385-1401 (1994); Hobbes et al., *Acc. Chem. Res.*, 29:114 (1996); Armstrong, et al., *Acc. Chem. Res.*, (1996) 29:123; Ellman, *Acc. Chem. Res.*, (1996) 29:132; Gordon et al., *Acc. Chem. Res.*, 29:144 (1996); Lowe, *Chem. Soc. Rev.*, 309 (1995); Blondelle et al., *Trends Anal. Chem.*, 14:83 (1995); Chen et al., *J. Am. Chem. Soc.*, 116:2661 (1994); U.S. Pat. Nos. 5,359,115, 5,362,899, and 5,288,514; PCT Publication Nos. WO92/10092, WO93/09668, WO91/07087, WO93/20242, and WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis," 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al. (*Proc. Natl. Acad. Sci. U.S.A.*, 90:6909 (1993)). Other synthesis methods, including the "tea-bag" technique of Houghten (see, e.g., Houghten et al., *Nature*, 354:84-86 (1991)) can also be used to synthesize libraries of compounds according to the subject invention.

Libraries of compounds can be screened to determine whether any members of the library can inhibit Hsp90 protein-protein interactions with Survivin, XIAP, cIAP1, or cIAP2, and, if so, to identify the inhibitory compound. Methods of screening combinatorial libraries have been described (see, e.g., Gordon et al., *J Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described above.

Test compounds can also include antibodies, e.g. antibodies that bind to Survivin, cIAP1, cIAP2, or XIAP. Antibodies suitable for screening in the methods disclosed herein include known antibodies as well as new antibodies (discussed more fully below) that selectively bind to peptides disclosed herein.

Screening Methods

In the screening methods described herein, peptide derivatives of a peptide can be used instead of the peptide. For example, peptide derivatives of a Survivin (or IAP protein) peptide can be used instead of the Survivin (or IAP protein) peptide.

The invention provides methods for identifying compounds capable of inducing apoptosis (by inhibiting the anti-apoptotic activity of an IAP protein) in a cell, e.g., a tumor cell. Although applicants do not intend to be bound by any particular theory as to the biological mechanism involved, such compounds are thought to prevent the ability of Hsp90 to bind to Survivin, XIAP, cIAP1, or cIAP2 and, in the case of Survivin, thereby prevent or inhibit cellular proliferation and/or induce cell death in cells, e.g., tumor cells.

In certain aspects of the new methods, screens for compounds that inhibit apoptosis are performed by identifying from a group of test compounds those that, e.g., (a) bind to a peptide disclosed herein, e.g., a peptide of Survivin, XIAP, cIAP1, or cIAP2 that contains an Hsp90 binding site and/or (b) inhibit Hsp90 protein-protein interactions with Survivin, XIAP, cIAP1, or cIAP2. Compounds that bind to the Survivin peptides disclosed herein are useful as compounds that also bind to the Hsp90 binding motif of Survivin, XIAP, cIAP1, or cIAP2 and thereby inhibit Hsp90 interactions with the Survivin, XIAP, cIAP1, or cIAP2. Such compounds are candidate compounds that induce apoptosis, and such candidate compounds can be further assayed for their ability to induce apoptosis in tumor cells in vitro or in vivo.

In other aspects of the new methods, screens for compounds that inhibit apoptosis are performed by identifying from a group of test compounds those that (a) bind to a peptide disclosed herein, e.g., a peptide of Hsp90 that contains a binding site for IAPs, e.g., Survivin, XIAP, cIAP1, or cIAP2, and/or (b) inhibit Hsp90 protein-protein interactions with Survivin, XIAP, cIAP1, or cIAP2. Compounds that bind to the Hsp90 peptides disclosed herein are useful as compounds that also bind to the IAP binding motif of Hsp90 and thereby inhibit Hsp90 interactions with an IAP, e.g., Survivin, XIAP, cIAP1, or cIAP2. Such compounds are candidate compounds that induce apoptosis, and such candidate compounds can be further assayed for their ability to induce apoptosis in tumor cells in vitro or in vivo.

Test compounds that bind to a Survivin or Hsp90 peptide disclosed herein and/or inhibit Hsp90 protein-protein interactions with Survivin, XIAP, cIAP1, or cIAP2 are referred to herein as "candidate compounds." Apoptosis inducing agents are candidate compounds further tested and found to be capable of inhibiting the activity of Survivin, XIAP, cIAP1, or cIAP2, and inducing apoptosis of tumor cells. In the new screening methods, candidate compounds can be, but do not necessarily have to be, tested to determine whether they are apoptosis inducing agents of tumor cells. Assays disclosed herein may be carried out in whole cell preparations and/or in ex vivo cell-free systems.

In one aspect, the invention includes methods for screening test compounds to identify compounds that bind to peptides disclosed herein. Binding of a test compound to a peptide disclosed herein can be detected, for example, in vitro by reversibly or irreversibly immobilizing either a test compound(s) or a peptide disclosed herein on a substrate, e.g., the surface of a well of a 96-well polystyrene microtiter plate. Methods for immobilizing compounds, e.g., peptides and other small molecules, are well known in the art. The ability of the test compound to bind a peptide disclosed herein can subsequently be measured by contacting the immobilized test compound or immobilized peptide disclosed herein, with the non-immobilized compound or non-immobilized peptide disclosed herein, washing the substrate, and measuring the amount of non-immobilized test compound or peptide disclosed herein that remains bound to the substrate. For example, microtiter plates can be coated with a peptide of the present invention by adding the peptide in a solution (typically, at a concentration of 0.05 to 1 mg/ml in a volume of 1-100 µl) to each well, and incubating the plates at room temperature to 37° C. for a given amount of time, e.g., for 0.1 to 36 hours. Peptides not bound to the plate can be removed by removing, e.g., decanting, aspirating, or shaking, excess solution from the plate, and then washing the plate (once or repeatedly) with water or a buffer. Typically, the peptide is in water or a buffer. The plate can then be washed with a buffer that lacks the bound peptide. To block the free protein-binding sites on the plates, plates can be blocked with a protein that is unrelated to the bound polypeptide. For example, 300 µl of bovine serum albumin (BSA) at a concentration of 2 mg/ml in Tris™-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate. Test compounds can then be added to the coated plate and allowed to bind to the immobilized peptide disclosed herein (e.g., at 37° C. for 0.5-12 hours). The plate can then be rinsed as described above.

Binding of a peptide disclosed herein to a second compound, e.g., the test compound described above can be detected by any of a variety of art-known methods. For example, an antibody that specifically binds to a peptide disclosed herein can be used in an immunoassay. If desired, the antibody can be labeled (e.g., fluorescently or with a radioisotope) and detected directly (see, e.g., West and McMahon, *J. Cell Biol.* 74:264, 1977). Alternatively, a secondary antibody can be used for indirect detection. In an alternative detection method, the test compound is labeled (e.g., with a radioisotope, fluorophore, chromophore, or the like), and the label is detected. In still another method, a test compound that is a polypeptide (test polypeptide) is produced as a fusion protein with a protein that can be detected optically, e.g., green fluorescent protein (which can be detected under UV light). In an alternative method, a test polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen, which can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying test polypeptides that bind to a peptide disclosed herein, conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature,* 340:245, 1989; Le Douarin et al., *Nucleic Acids Research,* 23:876, 1995; Vidal et al., *Proc. Natl. Acad. Sci. USA,* 93:10315-10320, 1996; and White, *Proc. Natl. Acad. Sci. USA,* 93:10001-10003, 1996). Generally, two-hybrid methods involve reconstitution of two separable domains of a transcription factor. One fusion protein contains a peptide disclosed herein fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the peptide disclosed herein to the test polypeptide reconstitutes the transcription factor. Reconstitution of the transcription factor can be detected by detecting expression of a gene (i.e., a reporter gene) that is operably linked to a DNA sequence that is bound by the DNA binding domain of the transcription factor. Kits for practicing various two-hybrid methods are commercially available (e.g., from Clontech; Palo Alto, Calif.).

In another aspect, the invention includes methods for screening test compounds to identify a compound that inhibits protein-protein interaction between Hsp90 and Survivin, XIAP, cIAP1, or cIAP2. A method useful for high throughput screening of compounds capable of modulating protein-protein interactions is described in Lepourcelet et al., *Cancer Cell,* 5: 91-102 (2004), which is incorporated herein by reference in its entirety. Typically, a first protein is provided. The first protein is either (i) Survivin, XIAP, cIAP1, cIAP2, or a peptide disclosed herein, or (ii) the first protein is an Hsp90 peptide that binds to Survivin, XIAP, cIAP1, or cIAP2. A second protein is provided which is different from the first protein and which is labeled. The second protein is either (i) Survivin, XIAP, cIAP1, cIAP2, or a peptide disclosed herein, or (ii) an Hsp90 peptide that binds to Survivin, XIAP, cIAP1, or cIAP2. A test compound is provided. The first protein, second protein, and test compound are contacted with each other. The amount of label bound to the first protein is then determined. A change in protein-protein interaction (e.g., binding) between the first protein and the second protein as assessed by the amount of label bound is indicative of the usefulness of the compound in inhibiting protein-protein interactions between Hsp90 peptide, and Survivin, XIAP, cIAP1, cIAP2, or a peptide disclosed herein. In some embodiments, the change is assessed relative to the same reaction without addition of the test compound.

In certain embodiments, the first protein is attached to a solid support. Solid supports include, e.g., resins such as agarose, beads, and multiwell plates. In certain embodiments, the method includes a washing step after the contacting step, so as to separate bound and unbound label.

In certain embodiments, a plurality of test compounds is contacted with the first protein and the second protein. The different test compounds can be contacted with the other compounds in groups or separately. In certain embodiments, each of the test compounds is contacted with both the first protein and the second protein in separate wells. For example, the method can screen libraries of test compounds, discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first protein is Survivin, XIAP, cIAP1, cIAP2, or a peptide disclosed herein, and the second protein is an Hsp90 peptide. In other embodiments, the first protein is Hsp90, or biologically active fragment thereof, e.g., a fragment including amino acid residues 1-272 of SEQ ID NO:21 that binds to Survivin, and the second protein is a Survivin, XIAP, cIAP1, cIAP2, or a peptide disclosed herein. The solid support to which the first protein is attached can be, e.g., SEPHAROSE™ beads, scintillation proximity assay (SPA) beads (microspheres that incorporate a scintillant) or a multiwell plate. SPA beads can be used when the assay is performed without a washing step, e.g., in a scintillation proximity assay. SEPHAROSE™ beads can be used when the assay is performed with a washing step. The second protein can be labeled with any label that will allow its detection, e.g., a radiolabel, a fluorescent agent, biotin, a peptide tag, or an enzyme fragment. The second protein can also be radiolabeled, e.g., with $^{125}$I or $^{3}$H.

In certain embodiments, the enzymatic activity of an enzyme chemically conjugated to, or expressed as a fusion protein with, the first or second protein, is used to detect bound protein. A binding assay in which a standard immunological method is used to detect bound protein is also included.

In certain other embodiments, the interaction of a first protein and a second protein is detected by fluorescence resonance energy transfer (FRET) between a donor fluorophore covalently linked to a first protein (e.g., a fluorescent group chemically conjugated to a peptide disclosed herein, or a variant of green fluorescent protein (GFP) expressed as a GFP chimeric protein linked to a peptide disclosed herein) and an acceptor fluorophore covalently linked to a second protein, where there is suitable overlap of the donor emission spectrum and the acceptor excitation spectrum to give efficient nonradiative energy transfer when the fluorophores are brought into close proximity through the protein-protein interaction of the first and second protein. Alternatively, both the donor and acceptor fluorophore can be conjugated at each end of the same peptide, e.g., a Survivin peptide. The free peptide has high FRET efficiency due to intramolecular FRET between donor and acceptor sites causing quenching of fluorescence intensity. Upon binding to Hsp90, the intramolecular FRET of the peptide-dye conjugate decreases, and the donor signal increases. In another embodiment, fluorescence polarization (FP) is used to monitor the interaction between two proteins. For example, a fluorescently labeled peptide will rotate at a fast rate and exhibit low fluorescence polarization. When bound to a protein, the complex rotates more slowly, and fluorescence polarization increases.

In other embodiments, the protein-protein interaction is detected by reconstituting domains of an enzyme, e.g., beta-galactosidase (see Rossi et al, *Proc. Natl. Acad. Sci. USA*, 94:8405-8410 (1997)).

In still other embodiments, the protein-protein interaction is assessed by fluorescence ratio imaging (Bacskai et al, *Science*, 260:222-226 (1993)) of suitable chimeric constructs of a first and second protein, or by variants of the two-hybrid assay (Fearon et al, *Proc. Nat'l. Acad. Sci USA*, 89:7958-7962 (1992); Takacs et al, *Proc. Natl. Acad. Sci. USA*, 90:10375-10379 (1993); Vidal et al, *Proc. Nat'l. Acad. Sci. USA*, 93:10315-10320 (1996); Vidal et al, *Proc. Nat'l Acad. Sci USA*, 93:10321-10326 (1996)) employing suitable constructs of first and second protein tailored for a high throughput assay to detect compounds that inhibit the first protein/second protein interaction. These embodiments have the advantage that the cell permeability of compounds that act as modulators in the assay is assured.

For example, in one assay, but not the only assay, a Survivin, XIAP, cIAP1, cIAP2, a peptide thereof or a fragment thereof is adsorbed to ELISA plates. The adsorbed polypeptides are then exposed to test compounds, followed by exposure to a Hsp90 or a peptide thereof (optionally fused to a reporter peptide such as Glutathione S-transferase). ELISA plates are washed and bound protein is detected using anti-Hsp90 antibody (or an antibody that selectively binds the reporter peptide). The antibody can be detected either directly or indirectly using a secondary antibody. Compounds that interfere with protein-protein interactions yield reduced antibody signal in the ELISA plates.

II. Antibodies

The invention features purified or isolated antibodies that bind, e.g., specifically bind, to tumor apoptosis-inducing peptides of Survivin, XIAP, cIAP1, or cIAP2 (or peptide derivatives thereof). Such antibodies inhibit protein-protein interactions between Hsp90 and Survivin, XIAP, cIAP1, or cIAP2, respectively. An antibody "specifically binds" to a particular antigen (e.g., a Survivin, XIAP, cIAP1, or cIAP2 peptide disclosed herein) when it binds to an epitope of that antigen, but does not substantially bind to other molecules in a sample, e.g., a biological sample that includes a Survivin, XIAP, cIAP1, or cIAP2 peptide disclosed herein, that do not contain the epitope to which the antibody binds. Antibodies of the invention include monoclonal antibodies, polyclonal antibodies, humanized or chimeric antibodies, single chain antibodies, Fab fragments, F(ab')$_2$ fragments, and molecules produced using a Fab expression library.

An example of a type of antibody included in the present invention is an antibody raised against a peptide disclosed herein. Such an antibody can be produced by isolating or synthesizing a peptide disclosed herein (e.g., SEQ ID NO: 2, 3, 4, or 5 or a peptide listed in FIG. 22) optionally coupled to an adjuvant ovalbumin, and injecting the peptide into an animal to raise polyclonal antibodies.

As used herein, the term "antibody" refers to a protein that includes at least one, e.g., two, heavy (H) chain variable regions (abbreviated herein as VH), and at least one, e.g., two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al. (1991) *Sequences of Proteins of Immunological Interest, Fifth Edition*, U.S. Department of Health and Human Services, NIH Publication No. 91-3242, and Chothia et al. (1987) *J. Mol. Biol.*, 196:901-917). Each VH and VL is composed of three CDR's and four FRs, arranged from amino-terminus to carboxy-terminus in the following order: FR1, CDR1, FR2, CDR2, FR3, CDR3, FR4.

An anti-Survivin, anti-XIAP, anti-cIAP1, or anti-cIAP2 antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

A "antigen binding fragment" of an antibody refers to one or more fragments of a full-length antibody that retain the ability to specifically bind to an antigen polypeptide or a portion thereof. Examples of antigen binding fragments of an anti-Survivin, anti-XIAP, anti-cIAP1, or anti-cIAP2 antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature*, 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science*, 242:423-426; and Huston et al. (1988) *Proc. Natl. Acad. Sci. USA*, 85:5879-5883). Such single chain antibodies are also encompassed within the terms: anti-Survivin antibody, anti-XIAP antibody, anti-cIAP1 antibody, or anti-cIAP2 antibody. These antibody fragments can be obtained using conventional techniques known to those with skill in the art.

To produce antibodies, Survivin, XIAP, cIAP1, cIAP2, or fragments or peptides thereof, that bind Hsp90, e.g., those produced by recombinant or peptide synthetic techniques (see, e.g., *Solid Phase Peptide Synthesis*, supra; Ausubel et al., supra), can be used. In general, the polypeptides can be coupled to a carrier protein, such as keyhole limpet hemocyanin (KLH), as described in Ausubel et al., supra, mixed with an adjuvant, and injected into a host mammal. A "carrier" is a substance that confers stability on, and/or aids or enhances the transport or immunogenicity of, an associated molecule.

Typically, to produce antibodies, various host animals are injected with antigen polypeptides. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Such procedures result in the production of polyclonal antibodies, i.e., heterogeneous populations of antibody molecules derived from the sera of the immunized animals. Antibodies can be purified from blood obtained from the host animal, for example, by affinity chromatography methods in which the Hsp90 binding polypeptide antigen is immobilized on a resin.

The present invention also includes monoclonal antibodies against a Survivin peptide, XIAP peptide, cIAP1 peptide, or cIAP2 peptide disclosed herein. Monoclonal antibodies (mAbs), which are homogeneous populations of antibodies to a particular antigen, can be prepared using peptides disclosed herein (e.g., SEQ ID NO: 2, 3, 4 or 5 or a peptide of FIG. 25) and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., *In Monoclonal Antibodies and T Cell Hybridomas*, Elsevier, N.Y., 1981; Ausubel et al., supra).

Typically, monoclonal antibodies are produced using any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77-96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies can be tested for binding, e.g., specific binding to Survivin, XIAP, cIAP1, or cIAP2 in an immunoassay, such as a Western blot or immunoprecipitation analysis using standard techniques, e.g., as described in Ausubel et al., supra. Antibodies that specifically bind to a Survivin, XIAP, cIAP1, or cIAP2 and inhibit protein-protein interactions between Hsp90 and Survivin, XIAP, cIAP1, or cIAP2, are useful in the invention. For example, such antibodies can be used to induce apoptosis in a tumor cell.

Alternatively or in addition, an antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology*, 9:1370-1372; Hay et al. (1992) *Hum. Antibod Hybridomas*, 3:81-85; Huse et al. (1989) *Science*, 246:1275-1281; Griffths et al. (1993) *EMBO J.*, 12:725-734; Hawkins et al. (1992) *J. Mol. Biol.*, 226:889-896; Clackson et al. (1991) *Nature*, 352:624-628; Gram et al. (1992) *Proc. Nat. Acad. Sci. USA*, 89:3576-3580; Garrad et al. (1991) *Bio/Technology*, 9:1373-1377; Hoogenboom et al. (1991) *Nuc. Acid Res.*, 19:4133-4137; and Barbas et al. (1991) *Proc. Nat. Acad. Sci. USA*, 88:7978-7982.

Antibodies can be fully human antibodies (e.g., an antibody made in a mouse which has been genetically engineered to produce an antibody from a human immunoglobulin sequence), or non-human antibodies, e.g., rodent (mouse or rat), goat, primate (e.g., monkey), camel, donkey, porcine, or fowl antibodies.

The antibodies can have a variable region, or a portion thereof, e.g., the CDRs, that is generated in a non-human organism, e.g., a rat or mouse. The antibody can also be, for example, chimeric, CDR-grafted, or humanized antibodies. The antibody can also be generated in a non-human organism, e.g., a rat or mouse, and then modified, e.g., in the variable framework or constant region, to decrease antigenicity in a human.

Techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778 and 4,704,692) can be adapted to produce single chain antibodies against a peptide disclosed herein. Single chain antibodies are formed by linking the heavy and light chain fragments of the Fv region via an amino acid bridge, resulting in a single chain polypeptide.

In one embodiment, recombinant vectors encoding antibodies described herein, e.g., single-chain antibodies, may be introduced into cells via gene therapy technologies, wherein the encoded antibody is expressed intracellularly, binds to an intracellular target, and thereby inhibits its function. Methods for engineering such intracellular antibodies, also known as "intrabodies" are known. This technology has been successfully applied in the art (for review, see Richardson and Marasco, 1995, *Trends Biotechnol.*, 13:306-310).

Antibody fragments that recognize and bind to specific epitopes can be generated by known techniques. For example, such fragments can include, but are not limited to, $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Also included in the invention are anti-idiotype antibodies designed to mimic the activity of tumor apoptosis-inducing peptides of Survivin, XIAP, cIAP1, or cIAP2 (or peptide derivatives thereof). These antibodies can be produced by selecting for antibodies that bind to the antigen-binding region of antibodies that bind to tumor apoptosis-inducing peptides of Survivin, XIAP, cIAP1, or cIAP2 (or peptide derivatives thereof). These anti-idiotype antibodies can be useful in methods of inducing apoptosis described herein.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry can modify moieties on a candidate compound or agent (i.e., a lead compound) and measure the effects of the modification on the efficacy of the compound or agent to thereby produce derivatives with increased potency. For an example, see Nagarajan et al. (1988) *J. Antibiot.*, 41: 1430-8. Furthermore, if the biochemical target of the compound (or agent) is known or determined, the structure of the target and the compound can inform the design and optimization of derivatives. Molecular modeling software is commercially available (e.g., from Molecular Simulations, Inc.) for this purpose.

IV. Pharmaceutical Compositions

The compounds and agents, peptides, and antibodies (all of which can be referred to herein as "active compounds" or "test compounds") that inhibit protein-protein interactions between Hsp90 and Survivin, XIAP, cIAP1, or cIAP2, can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent which delays absorption, e.g., aluminum monostearate or gelatin, in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, or other compound can include a single treatment or, preferably, can include a series of treatments.

For a peptide described herein, an effective dosage ranges from about 0.001 to 30 mg/kg body weight, e.g., about 0.01 to 25 mg/kg body weight, e.g., about 0.1 to 20 mg/kg body weight. For antibodies, a useful dosage is 0.1 mg/kg of body weight (generally 0.1 mg/kg to 20 mg/kg). Typically, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules encoding a polypeptide described herein can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Methods of Treatment

One of the most significant features of Survivin is its differential expression in cancer versus normal tissues. Reminiscent of "onco-fetal" antigens, Survivin is strongly expressed in embryonic and fetal organs, but undetectable in most terminally differentiated normal tissues. Adult normal tissues reported to express Survivin include thymus, CD34$^+$ bone marrow-derived stem cells at low levels, and the basal colonic epithelium, but not basal keratinocytes. In contrast, dramatic overexpression of Survivin was demonstrated in tumors of lung, breast, colon, stomach, esophagus, pancreas, liver, uterus, ovary, and brain. Survivin is also overexpressed in tumor tissue associated with Hodgkin's disease, large cell non-Hodgkin's lymphomas, leukemias, myelodysplastic syndrome with refractory anemia, neuroblastoma, pheochromocytoma, soft tissue sarcomas, melanoma, and non-melanoma skin cancers. In genome-wide searches, Survivin was identified as the top fourth "transcriptome" expressed in cancers of the colon, lung, brain, breast and melanoma, but was undetectable or found at very low levels in the normal tissues of the same organs. See, Velculescu, et al., *Nat. Genet.*, 23, 387-388 (1999).

Candidate compounds that inhibit protein-protein interactions between Hsp90 and Survivin, e.g., the peptides, peptide derivatives, and small molecules disclosed herein, can be used in methods of treating uncontrolled cellular proliferation, such as cancer. The peptides and peptide derivatives can be administered to a patient diagnosed with cancer, e.g., any of the types of cancers referred to herein. For example, the peptides, peptide derivatives, and small molecules disclosed herein can be used to treat a subject suffering from a lung, breast, colon, stomach, esophagus, pancreas, liver, uterus, ovary, or brain tumor. In other examples the peptides and peptide derivatives disclosed herein can be used to treat a subject suffering from Hodgkin's disease, large cell non-Hodgkin's lymphoma, leukemia, myelodysplastic syndrome with refractory anemia, neuroblastoma, pheochromocytoma, soft tissue sarcoma, melanoma, or non-melanoma skin cancer.

EXAMPLES

Example 1

Survivin Interacts with Hsp90

Several experiments were performed demonstrating the protein-protein interaction of Survivin and Hsp90. Human cervical carcinoma HeLa cells and B lymphoma Raji cells were obtained from American Type Culture Collection (ATCC) (Manassas, Va.), and maintained in culture according to the supplier's specifications. For Western blots, 12% sodium dodecyl sulfate (SDS) gels were transferred to nylon membranes and incubated with 1-5 µg of primary antibodies. Rabbit polyclonal antibody to Survivin was obtained from NOVUS Biologicals (Littleton, Colo.); monoclonal antibody (mAb) to Hsp90 was obtained from BD-Transduction Laboratories (cat. No. H38220; Lexington, Ky.); monoclonal antibody to tubulin was obtained from Sigma. Primary antibodies were visualized using horseradish peroxidase (HRP)-conjugated secondary antibodies (Amersham, Piscataway, N.J.) and a chemiluminescence kit (Amersham).

FIG. 1A shows that Survivin interacts with Hsp90 and tubulin. $1.5 \times 10^8$ HeLa cells were collected, washed once in ice cold Tris™-Buffered Saline (TBS) and lysed for 1 hour at 4° C. in 2 volumes of lysis buffer (TBS pH 7.4, 1% Triton™ X-100, 1 mM phenyl-methylsulfonyl fluoride (PMSF), plus other protease inhibitors). Cell lysate was clarified by centrifugation at 15,000 g for 30 minutes at 4° C., and applied to 0.5 ml of cyanogen bromide (CNBr) activated Sepharose™ 4B (Amersham Pharmacia) coupled to 5 mg of polyclonal antibody to Survivin. An empty resin was used as control. After extensive washing of the columns in lysis buffer, elution buffer (0.1 M glycine, pH 2.5) was added, and fractions of 0.5 ml were collected and neutralized with 1 M Tris™ pH 8.0. Samples were dialyzed against TBS, separated onto a 12% SDS gel and analyzed by Coomassie staining and Western blotting. Western blots identified the 90 kDa and 55 kDa proteins that co-eluted with Survivin as Hsp90 and tubulin, respectively, as shown in FIG. 1A.

Figure 1B:
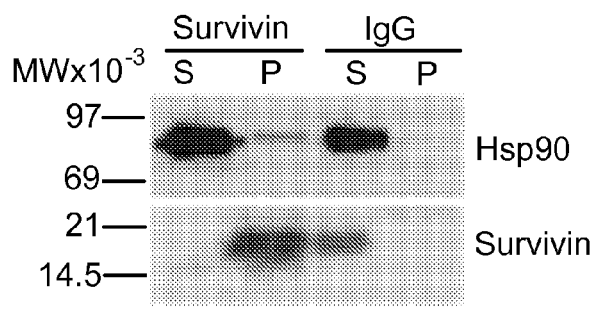
FIG. 1B is an image of an immunoblot of proteins that co-immunoprecipitated with Survivin or control non-binding IgG antibodies. S and P indicate supernatant and immunoprecipitated pellet, respectively.

FIG. 1B shows the co-immunoprecipitation of Survivin and Hsp90. Asynchronously growing B lymphoma Raji cells ($5 \times 10^5$) were lysed and cleared by centrifugation as described above. Supernatants and resuspended pellets were immunoprecipitated with Survivin (Survivin) or control, non-binding IgG (IgG) antibodies (2.5-5 µg/ml) for 16 hours at 4° C. Immune complexes were precipitated by addition of 50 µl of a 50:50 protein A or protein G slurry. Precipitated immune complexes from pellet (P) or supernatant (S) were analyzed with antibodies to Hsp90 or Survivin by Western blotting as shown in FIG. 1B.

Figure 1C:
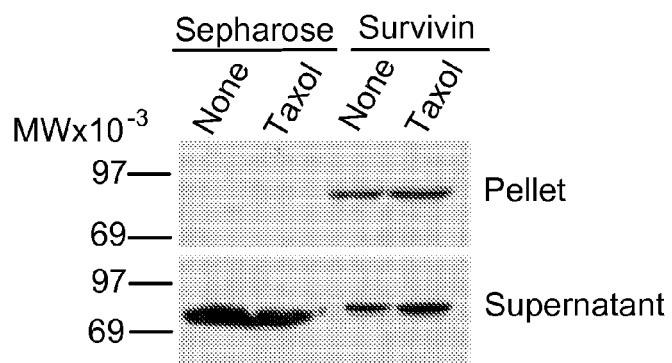
FIG. 1C is an image of an immunoblot showing the results of in vivo pull-down experiments. The immunoblot show that Hsp90 was precipitated from cell extracts by Sepharose™ coupled to Survivin ("Survivin"), but not by Sepharose™ alone ("Sepharose"). Cells were treated with Pellets or supernatants (25% of reaction), as indicated, were analyzed using anti-Hsp90.

FIG. 1C shows the result of an in vivo pull-down of Survivin and Hsp90. Asynchronous HeLa cell cultures or HeLa cells synchronized at the mitotic transition by treatment with paclitaxel (Taxol™) (2 µM, Sigma) were harvested. Cellular extracts were incubated with Sepharose™ ("Sepharose") or Survivin-Sepharose™ ("Survivin"), and pellets or supernatants (25% of reaction) were analyzed for co-associated Hsp90 by Western blotting. Samples from asynchronous cultures are labeled "None" and samples from Taxol™ treated cells are labeled accordingly.

These results demonstrate protein-protein interactions between Survivin and Hsp90.

Example 2

Proper Folding of Survivin is Required for Binding to Hsp90

ELISA experiments were performed by immobilizing recombinant Survivin (r-Survivin) (10 mg/ml) or recombinant Hsp90 (r-Hsp90) (10 µg/ml) on plastic microtiter wells (Immulon™-2, Dynatech Laboratories, Chantilly, Va.) using bicarbonate buffer, pH 9.5 (100 µl/well) for 18 hours at 4° C. Bound protein was blocked with 3% gelatin for 1 hour at 37° C., rinsed with washing buffer (TBS pH 7.4, 0.1% Tween™, 0.1% BSA) and incubated for 1 hour at 37° C. with different concentrations of a test protein to determine if the test protein bound the immobilized protein.

GST-Hsp90 (amino acids 1-732), recombinant GST-Survivin, and GST-Survivin (C84A) were expressed in *E. coli* and bound to glutathione beads (Sigma). Hsp90α was cloned by PCR in pGex-4T3 (Amersham Pharmacia Biotech.). Purified r-Survivin devoid of the GST frame was obtained by digestion of the corresponding GST fusion proteins with thrombin (Sigma, 20 U/ml in 50 mM Tris™ pH 7.4, 150 mM NaCl, 5 mM MgCl$_2$, 2.5 mM CaCl$_2$, 1 mM DTT). Twenty micrograms of GST or GST fusion proteins bound to glutathione beads (20 µl) were washed twice in binding buffer (10 mM Tris™ pH 7.5, 10 mM EDTA, 100 mM NaCl, 0.1% Triton™, 1 mM DTT and protease inhibitors), incubated for 2.5 hours at room temperature (RT) in 100 µl of binding buffer with increasing amounts (5 µg, 10 µg, 20 µg, 40 µg) of r-Survivin and then washed 5 times. The bound and one fourth of the unbound proteins were separated onto a 12% SDS gel and stained using GelCode® Blue Stain Reagent (Pierce).

Figure 2A:
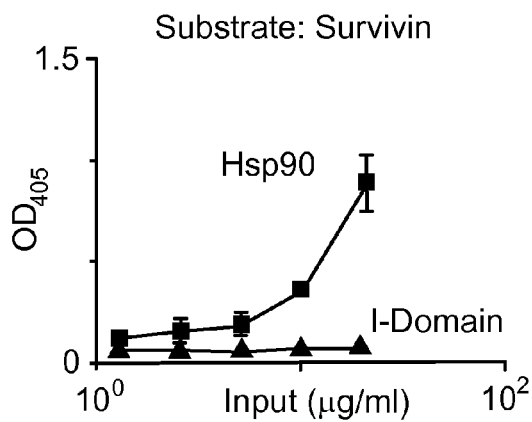
FIG. 2A and FIG. 2B are graphs quantifying the results of ELISA experiments that showed Hsp90 bound to immobilized Survivin substrate (FIG. 2A) and wild type Survivin bound to immobilized Hsp90 substrate (FIG. 2B). In contrast, a Survivin point mutant C84A did not bind to Hsp90 (FIG. 2B).

In one experiment, wells containing immobilized and blocked r-Survivin were incubated with r-Hsp90 or recombinant CD11b integrin domain (I-domain), washed ten times, and incubated with anti-Hsp90 mAb (1 µg/ml) or control non-Immune IgG (1 µg/ml) for 1 hour at 37° C. After ten additional washes, binding of the primary antibodies was assayed by addition of biotin-conjugated, rabbit anti-mouse IgG for 1 hour at 37° C., followed by streptavidin-alkaline phosphatase and determination of absorbance at OD$_{405}$ using p-nitrophenyl phosphate (Zymed Laboratories, South San Francisco, Calif.) as substrate. FIG. 2A shows the quantified results of these experiments: rHsp90 bound to immobilized r-Survivin in a dose dependent manner; whereas control I domain failed to bind r-Survivin.

Figure 2B:
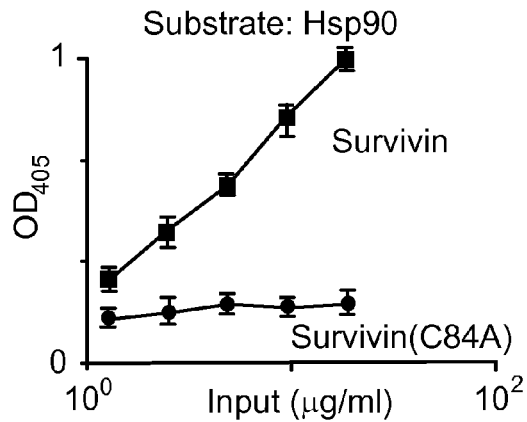

In another experiment, immobilized r-Hsp90 Survivin was mixed with increasing concentrations of r-Survivin or recombinantly expressed Survivin Cys$^{84}$→Ala mutant (Survivin (C84A)). Survivin (C84A) eliminates the Zinc coordination sphere in the BIR and generates an unfolded molecule. Bound proteins were detected by ELISA using polyclonal anti-Survivin and quantified by absorbance at $OD_{405}$, as described above. Results shown in FIG. 2B indicate that Survivin and Hsp90 exhibit reciprocal binding, but the Survivin (C84A) unfolded mutant failed to bind to Hsp90.

These results demonstrate Hsp90 bound to Survivin in a dose-dependent manner, and that Hsp90 binding to Survivin is not merely a non-specific chaperone response to a Survivin domain that mimics an unfolded protein. Furthermore, the data demonstrate that Survivin requires proper folding to interact with Hsp90. Therefore, the Hsp90-Survivin complex is not involved in promoting degradation of Survivin but, conversely, in preserving stability of Survivin.

Example 3

Survivin Binds to the N-Terminus of Hsp90

Nucleotide sequences encoding full length Hsp90α (SEQ ID NO:21; amino acids 1-732) or three fragments: N-Hsp90 (amino acids 1-272 of SEQ ID NO:21), M-Hsp90, (amino acids 273-617 of SEQ ID NO:21), and C-Hsp90 (amino acids 629-732 of SEQ ID NO:21) were cloned by PCR in pGex-4T3 (Pharmacia Biotech.) and pFLAG-CMV 6c (Sigma) using the BamHI cloning sites. GST fusions of full length Hsp90, or individual Hsp90 fragments were expressed in *E. coli* and bound to glutathione beads (Sigma). Purified recombinant Survivin devoid of the GST frame was obtained as described in Example 2.

Figure 3A:
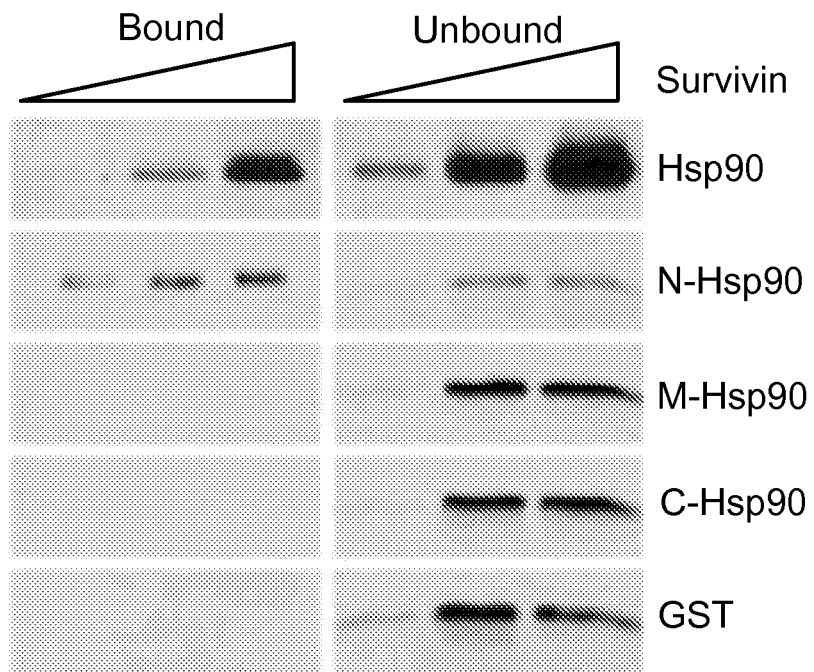
FIG. 3A is an image of an immunoblot showing the results of in vitro pull-down experiments. The immunoblot shows that the N-terminus ATPase-containing domain of Hsp90 bound to Survivin coupled to Sepharose™, but the sequences downstream of the N-terminal domain of Hsp90 did not bind to Survivin coupled to Sepharose™.

FIG. 3A shows the results of Survivin/Hsp90 in vitro pull-down experiments. Increasing concentrations of r-Survivin (30, 100 and 300 ng/50 µl reaction) were incubated with Sepharose™-GST-Hsp90 (10 µg/50 µl reaction) or GST fused to N-Hsp90, M-Hsp90, or C-Hsp90 domains. Reactions were centrifuged to pellet the Sepharose™-GST fusions. Protein binding was determined by analyzing pellets (Bound) or Supernatant (Unbound) by Western blotting. See FIG. 3A, showing that Survivin bound only to full length Hsp90 or to the N-Hsp90 fragment (amino acids 1-272) that contains the ATP-binding domain of Hsp90.

Figure 3B:
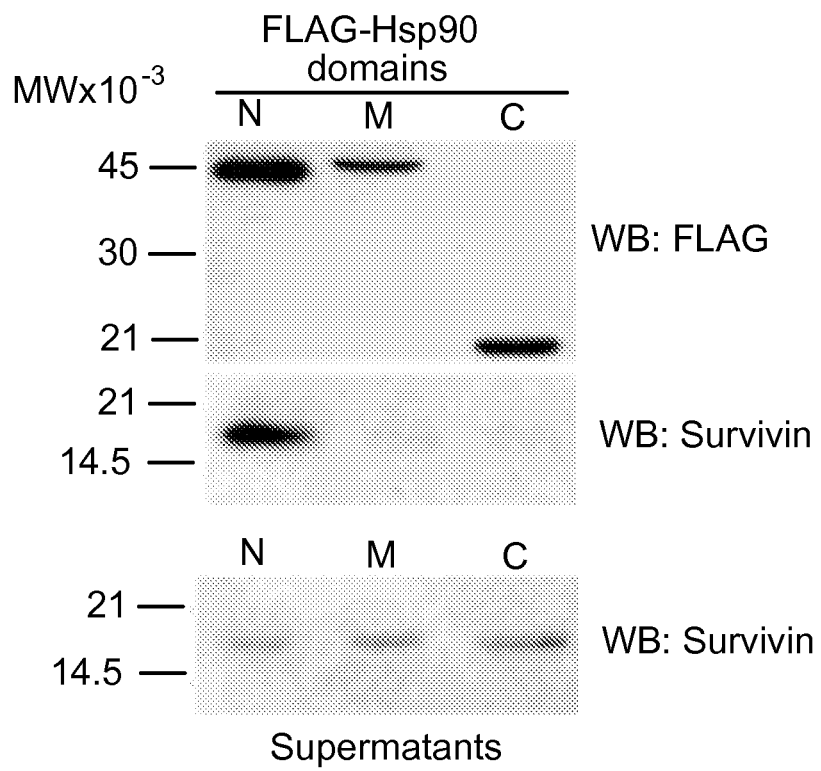
FIG. 3B is an image of an immunoblot of proteins that co-immunoprecipitated with FLAG conjugated domains of Hsp90, in vivo. The image shows that Survivin co-immunoprecipitated only with the N-terminal domain of Hsp90, and did not bind to portions downstream of the N-terminal domain of Hsp90.

FIG. 3B shows that Survivin co-immunoprecipitates with the N-terminal domain of Hsp90, in vivo. HeLa cells were transfected with the indicated FLAG-Hsp90 N, M, or C domains, proteins were immunoprecipitated with a mAb to FLAG (Sigma, cat. No. F3165, St. Louis, Mo.), and immune complexes were analyzed for co-associated Survivin using a polyclonal antibody to Survivin or a mAb to FLAG, by Western blotting. FIG. 3B shows that only the N-Hsp90 fragment was able to immunoprecipitate Survivin.

These results demonstrate that Survivin binds to the ATPase domain containing N-terminus of Hsp90.

Example 4

Hsp90 Interacts with Other Members of the IAP Family

The cDNAs for XIAP and XIAP Baculovirus IAP Repeats (BIR) domains (BIR1, Met 1 to Ser 123; BIR2, Arg 124 to Pro 260; and BIR3, Ser 261 to Gln 336) were obtained from retro-transcription (SuperScript™ First Strand Synthesis System for RT-PCR, Invitrogen) of RNA extracted from HeLa cells (TRI Reagent™, Molecular Research Center Inc.), amplified by PCR, and cloned in pcDNA3 vector (Invitrogen). pcDNA3-XIAP and pcDNA3-XIAP BIR domains were translated in vitro using the TNT™ Quick Coupled Transcription/Translation System (Promega) in the presence of $^{35}$S labeled methionine (Amersham), and 2, 5, and 8 µl of the reaction were incubated with 10 µg GST or GST fusion proteins as described above.

Figure 4A:
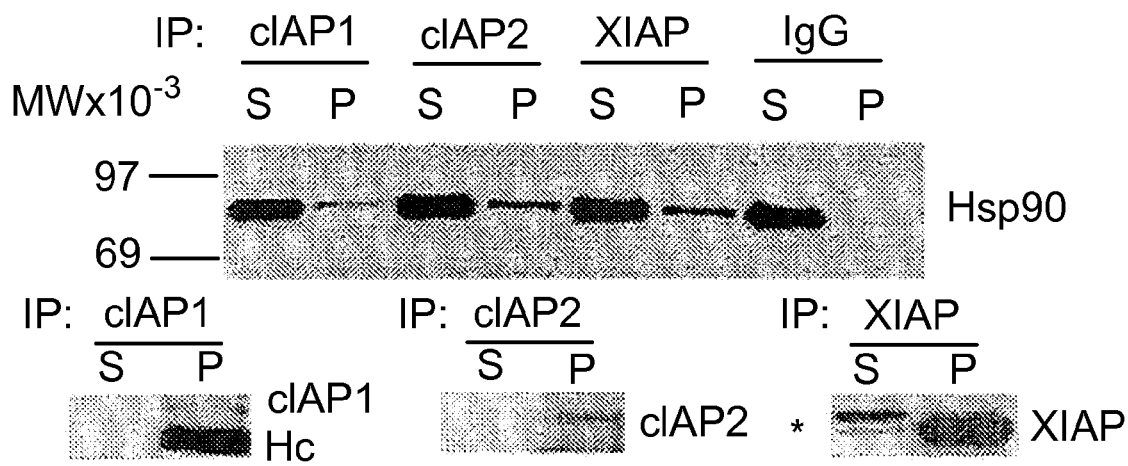
FIG. 4A is an image of immunoblots showing that cIAP1, cIAP2, and XIAP co-immunoprecipitate with Hsp90.

FIG. 4A shows that cIAP1, cIAP2, and XIAP associate with Hsp90. Raji cell extracts were immunoprecipitated (as described above) with antibodies to cIAP1, cIAP2, XIAP or a control non-binding IgG (IgG). Antibodies to XIAP, cIAP1, and cIAP2 were obtained, respectively, from BD-Transduction Laboratories (cat. No. 610763), BD-PharMingen (cat. No. 556533, San Diego, Calif.) and Santa Cruz Biotechnology (cat. No. sc-7944; Santa Cruz). Immune complexes (P) and unbound material (S) were analyzed by Western blotting with anti-Hsp90 (upper panel). FIG. 4A shows that cIAP1, cIAP2, and XIAP immune complexes (P) precipitated Hsp90, but control IgG did not. Comparable immunoprecipitation of the various IAPs was also demonstrated by Western blotting.

Figure 4B:
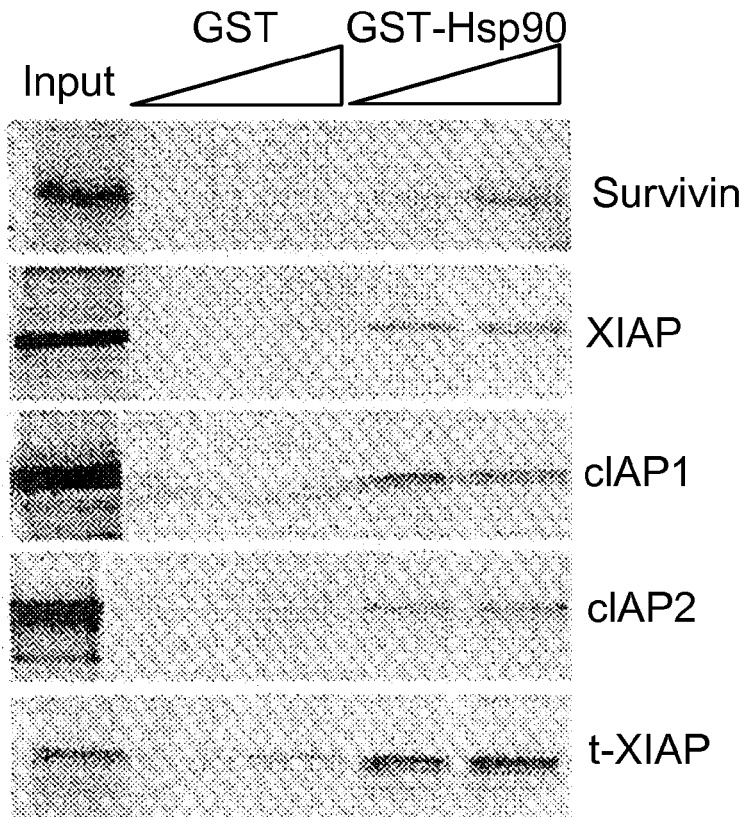
FIG. 4B is an image of immunoblots showing the results of in vitro pull-down experiments. The immunoblots show that cIAP1, cIAP2, XIAP, and a truncated XIAP containing only the three baculovirus repeat (BIR) domains (t-XIAP) bound to a GST-Hsp90 fusion protein.

FIG. 4B shows the in vitro interaction of Hsp90 with various IAP proteins. The various IAP proteins, including Survivin, XIAP, cIAP1, cIAP2, and a truncated form of XIAP (t-XIAP) containing only the three BIR domains and spanning residues 1-292, were transcribed and translated in vitro in the presence of $^{35}$S-methionine, mixed with Sepharose™-GST or Sepharose™-GST-Hsp90 in pull-down experiments, and bound proteins were visualized by autoradiography.

These results demonstrate the existence of protein-protein interactions between Hsp90 and (a) cIAP1, (b) cIAP2, and (c) XIAP.

Example 5

Hsp90 Controls the Stability of Survivin and Other IAP Proteins

Cells were maintained and Western blots were performed as described in Example 1.

Figure 5A:
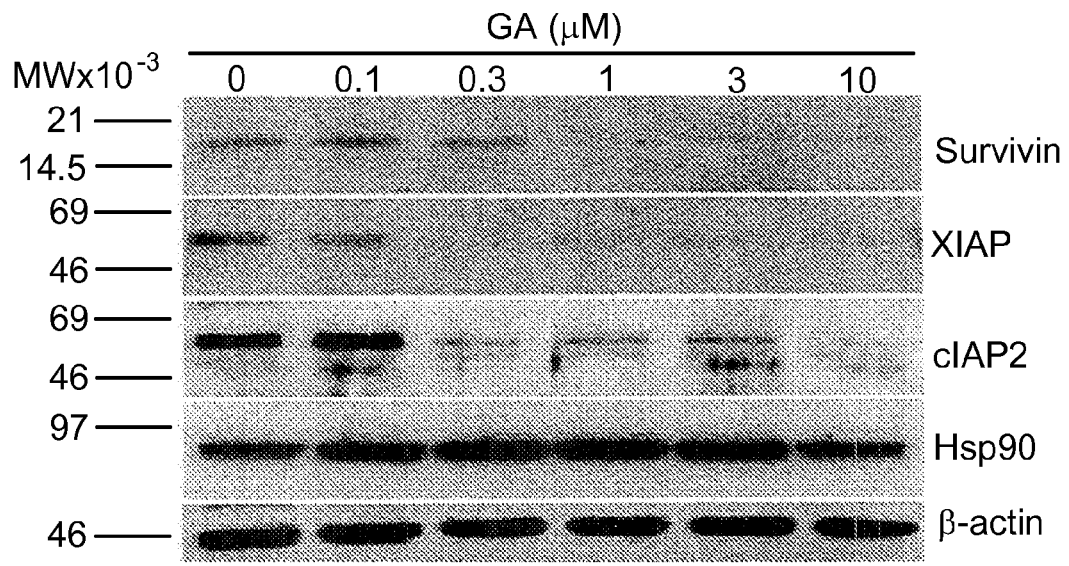
FIG. 5A is an image of an immunoblot showing that IAP proteins degraded in HeLa cell extracts treated with geldanamycin (GA) for 24 hours at the indicated concentrations.

FIG. 5A shows the degradation of IAP proteins induced by geldanamyicn (GA), an inhibitor of the ATPase cycle of Hsp90. HeLa cells treated with the indicated concentrations of geldanamycin (GA) for 24 hours were analyzed for changes in IAP levels by Western blotting. Treatment with 1 µM GA decreased the steady-state levels of Survivin, XIAP, and cIAP2 relative to the untreated control. Levels of Hsp90 and β-actin were unaffected by GA treatment.

Figure 5B:
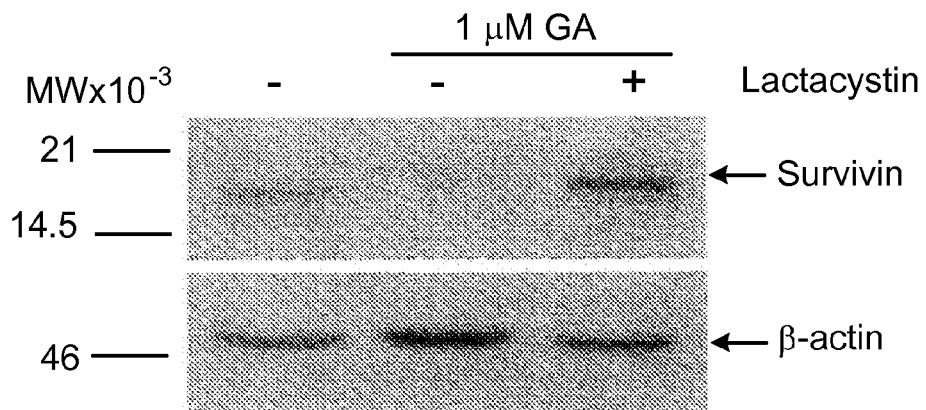
FIG. 5B is an image of an immunoblot showing that Survivin was protected from GA-mediated degradation by the presence of proteasome inhibitor lactacystin.

FIG. 5B shows the effect of proteasome inhibition on Survivin stability in the presence of GA. Extracts from HeLa cells treated with 1 µM GA for 30 hours in the presence or absence of 5 µM of the proteasome inhibitor lactacystin were analyzed for changes in Survivin or β-actin levels by Western blotting. Antibodies to actin were obtained from Sigma. Survivin levels following lactacystin and GA treatment were at or above the levels of untreated cells, indicating Survivin is subject to proteolysis during GA treatment. Levels of β-actin were unaffected by treatment in this experiment.

Figure 5C:
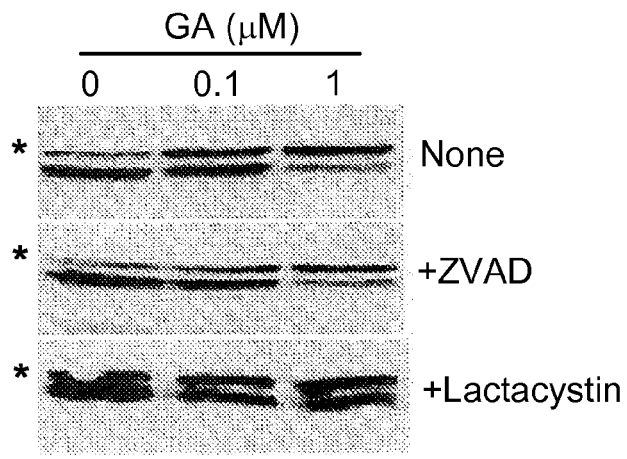
FIG. 5C is an image of immunoblot showing that XIAP was protected from GA-mediated degradation by the proteasome inhibitor lactacystin and that XIAP was not protected form GA-mediated degradation by caspase inhibitor Z-Val-Ala-Asp (OMe)-$CH_2F$ (ZVAD-fmk).

FIG. 5C shows the degradation of XIAP in the presence of GA is mediated by the proteasome but not by activated caspases. HeLa cell extracts were collected after exposure to the indicated concentrations of GA in the absence (None) or in the presence of the proteasome inhibitor, lactacystin or the broad spectrum caspase inhibitor, ZVAD-fmk. Loss of XIAP expression in the presence of Hsp90 inhibition by GA is reversed by lactacystin but not ZVAD-fmk, as indicated by Western blotting for XIAP depicted in FIG. 5C (* indicates non-specific band).

These results indicate that Hsp90 function is required for the stable expression of Survivin, cIAP1, cIAP2, and XIAP. It is therefore possible that the apoptosis-inducing effect of the peptides/antibodies/compounds disclosed herein is mediated, at least in part, by their ability to prevent the interaction of Survivin, cIAP1, cIAP2, and/or XIAP with Hsp90, and thereby reduce the stability and expression of these anti-apoptotic proteins.

Example 6

Figure 6:
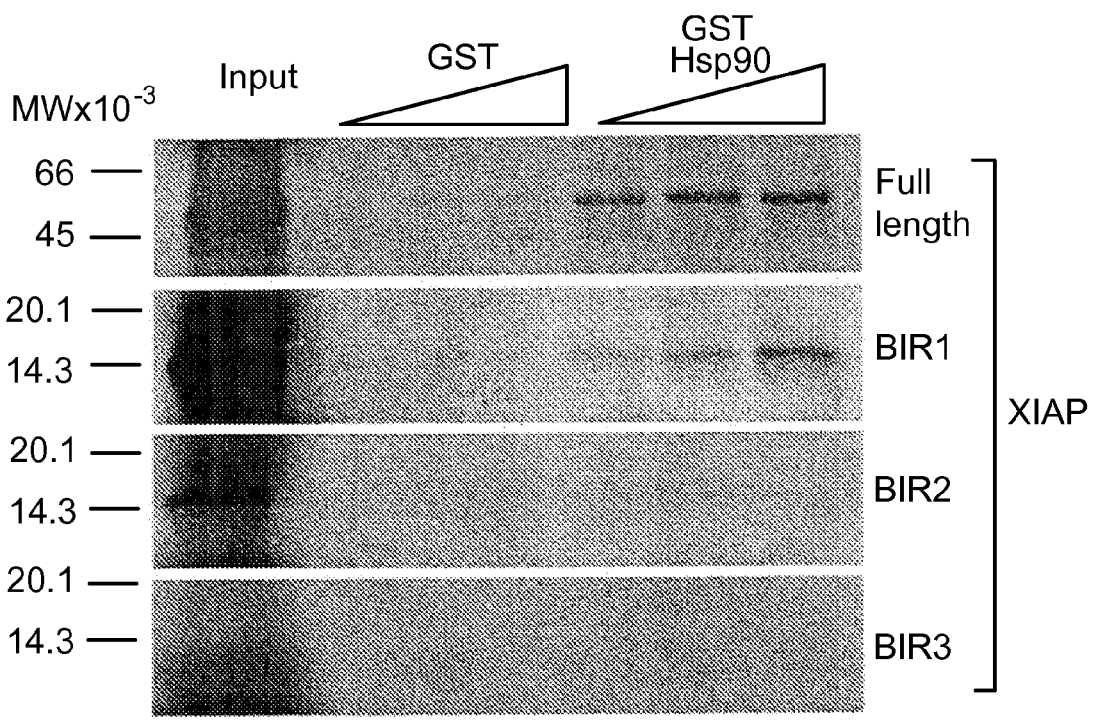
FIG. 6 is an image of immunoblots showing that the first BIR domain of XIAP bound to GST-Hsp90.

Identification of the Hsp90 Binding Site on XIAP pcDNA3-XIAP and pcDNA3-XIAP BIR domains were translated in vitro as described in Example 4. FIG. 6 shows the in vitro interaction between Hsp90 and the isolated BIR fragments of XIAP reveals a selective association with the amino-terminus BIR (BIR1). GST-Hsp90 or GST was mixed with $^{35}$S in vitro translated XIAP or its individual Baculovirus IAP Repeats: BIR1, BIR2, and BIR3. Reactions were centrifuged and proteins that associated with the pellet were detected by autoradiography. FIG. 6 shows that only full length XIAP and the isolated BIR1 fragment associated with GST-Hsp90.

These results identify BIR1 as containing the Hsp90 binding domain of XIAP. The sequence of amino acids Met 1 to Ser 123 of XIAP, including BIR1, is:

```
                                         (SEQ ID NO: 27)
MTFNSFEGSKTCVPADINKEEEFVEEFNRLKTFANFPSGSPVSASTLAR

AGFLYTGEGDTVRCFSCHAAVDRWQYGDSAVGRHRKVSPNCRFINGFYL

ENSATQSTNSGIQNGQYKVENYLGS
```

Example 7

Identification of the Hsp90 Binding Site on Survivin (K79-K90)

Figure 7:
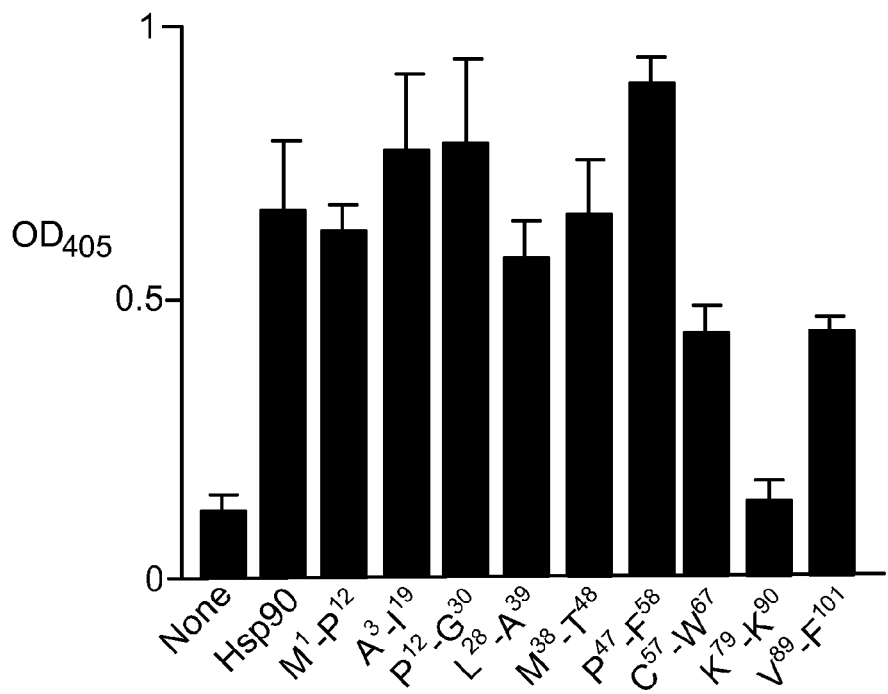
FIG. 7 is a bar graph showing the inhibitory effects of the indicated Survivin fragment peptides on Hsp90-Survivin protein-protein interactions, as measured in ELISA experiments.

FIG. 7 shows the identification of a synthetic peptide from the Survivin sequence that inhibits the interaction between Survivin and Hsp90. ELISA experiments were performed essentially as in Example 2 with the following variations. 20 µg/ml of each recombinant Survivin peptide (expressed in *E. coli*) was preincubated with Hsp90 at 2.5 mg/ml for 16 hours at 4° C. After binding and blocking of full length Survivin to wells in a microtiter plate, the preincubated mixtures of Hsp90 and Survivin peptides were added to the wells and incubated for 1 hour at 37° C. Wells were washed, incubated with primary antibody, washed again, and bound antibody was quantified as described above. Each experiment was repeated three times and the standard deviation is shown. The twelve amino acid Survivin peptide including Lysine 79-Lysine 90 (K79-K90; SEQ ID NO:3) was an especially effective inhibitor of Hsp90-Survivin binding interactions.

These results are consistent with the assignment of an Hsp90 binding site to the K79-K90 domain of Survivin and provide a working example of a method of screening for compounds that inhibit Hsp90-Survivin interactions.

Example 8

Characterization of an Antibody Antagonist of the Survivin-Hsp90 Interaction

Figure 8A:
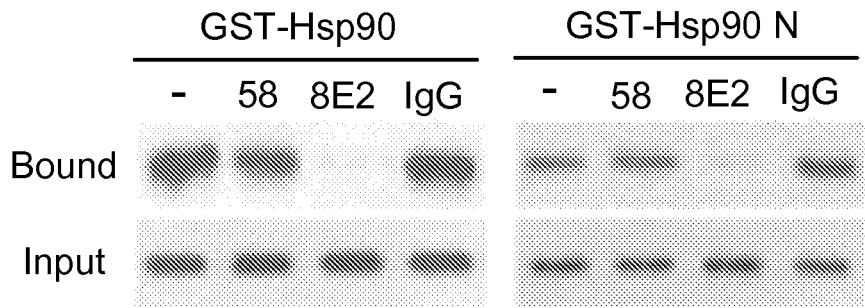
FIG. 8A is an image of immunoblots for Survivin showing that mAb 8E2 inhibited Survivin protein-protein interactions with GST-Hsp90, while mAb 58 did not have such an inhibitory effect.

Murine anti-Survivin monoclonal antibodies (mAbs) 8E2 and 58 were obtained from NOVUS Biologicals (Littleton, Colo.). FIG. 8A shows that mAb 8E2, but not mAb 58, inhibits Survivin-Hsp90 protein-protein interactions in competition assays. R-Survivin (300 ng) was preincubated with 3 mg of a mouse monoclonal antibody to Survivin, mAb 58 or 8E2, in 50 ml of binding buffer for 1 hour at 22° C. 5 mg of GST-Hsp90 or GST-N-Hsp90 was then added to the buffer, GST was centrifuged and protein bound to Hsp90 was detected by Western blotting for Survivin. Monoclonal antibody 8E2 decreased the amount of survivin precipitated by either GST fusion protein.

Figure 8B:
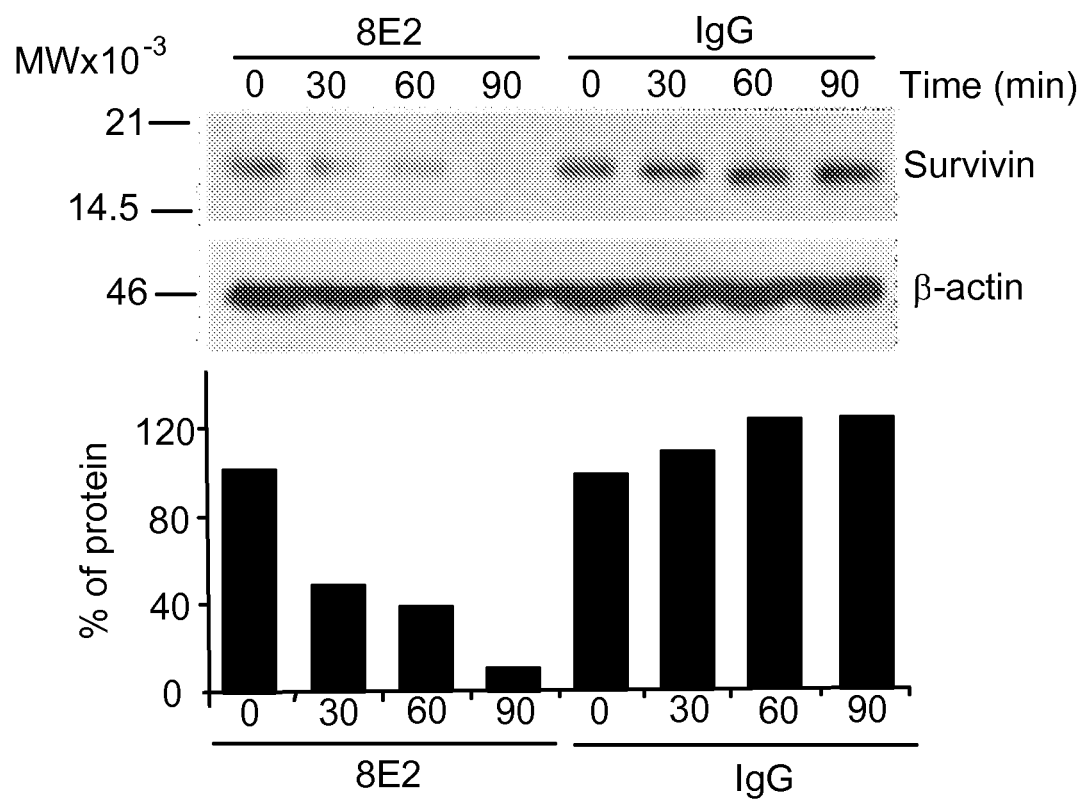
FIG. 8B is an immunoblot showing that intracellular loading of mAb 8E2 induced the down-regulation of Survivin expression. Quantification of the immunoblot is shown below.

FIG. 8B shows that the in vivo displacement of the Survivin-Hsp90 interaction by intracellular loading of mAb 8E2 downregulates Survivin expression. For these experiments, HeLa cells ($2 \times 10^5$) were loaded with 5 µg of mAbs 8E2 or 58 to Survivin, or mouse IgG in OptiMEM™ (Invitrogen, Carlsbad, Calif.), in the presence of BioPORTER™ Protein Transfection Reagent (Gene Therapy Systems, San Diego, Calif.). After 4 hours, cells were supplemented with 100 µg/ml cycloheximide, and analyzed over 90 minutes (times 0, 30, 60, and 90 minutes) for Survivin expression by Western blotting (FIG. 8B, upper panel). The efficiency of antibody loading (90%) was determined using FITC-conjugated IgG (5 µg) and fluorescence microscopy. The protein amount was normalized against β-actin levels and quantified (FIG. 8B, lower panel). Thus, FIG. 8B shows that mAb 8E2 mediated disruption of Hsp 90-Survivin interaction inhibits Survivin expression/stability.

These results indicate that mAb 8E2 inhibits Survivin-Hsp90 protein-protein interactions, and thereby reduces Survivin expression.

Example 9

Figure 9A:
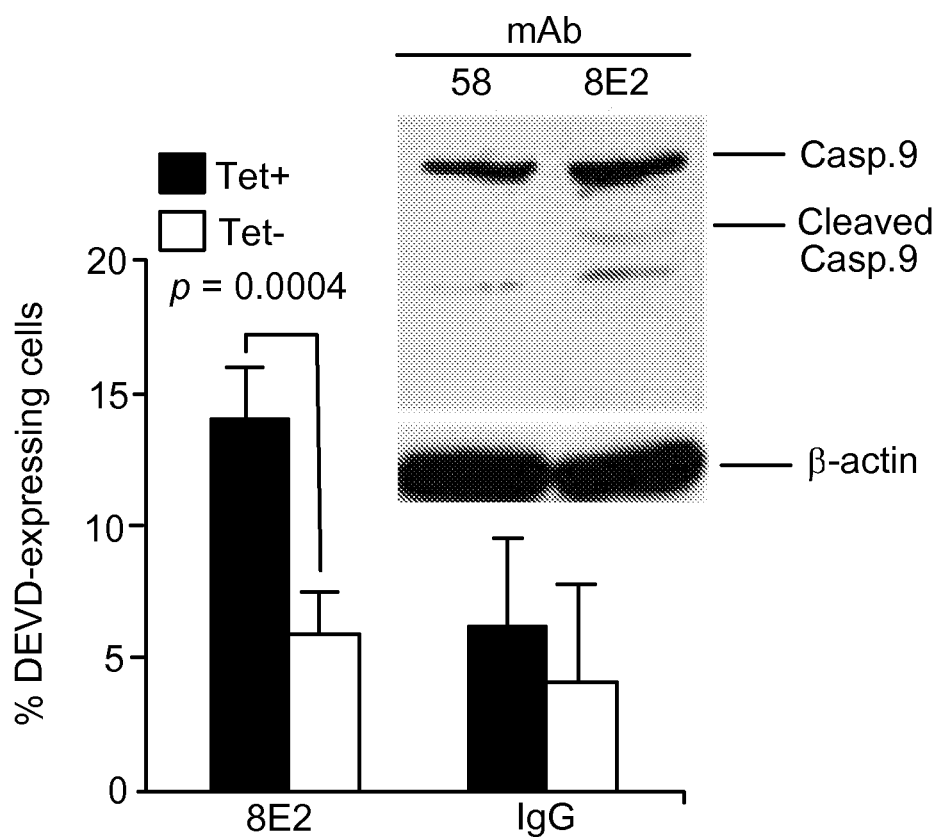
FIG. 9A is a graph with an image of an immunoblot inset. The graph quantifies the caspase activity by accumulation of a caspase substrate, as measured by flow cytometry of cells loaded with mAb 8E2 or control IgG. The cells express Survivin in the absence of tetracycline (Tet−) but not in the presence of (Tet+). The data demonstrate that over-expression of Survivin using the tetracycline-inducible system (Tet-Off system) can overcome induction of apoptosis induced by intracellular loading of the antibody 8E2. The inset image of an immunoblot shows that mAb 8E2 induced caspase 9 cleavage, an indication of induction of apoptosis.
Figure 9E:
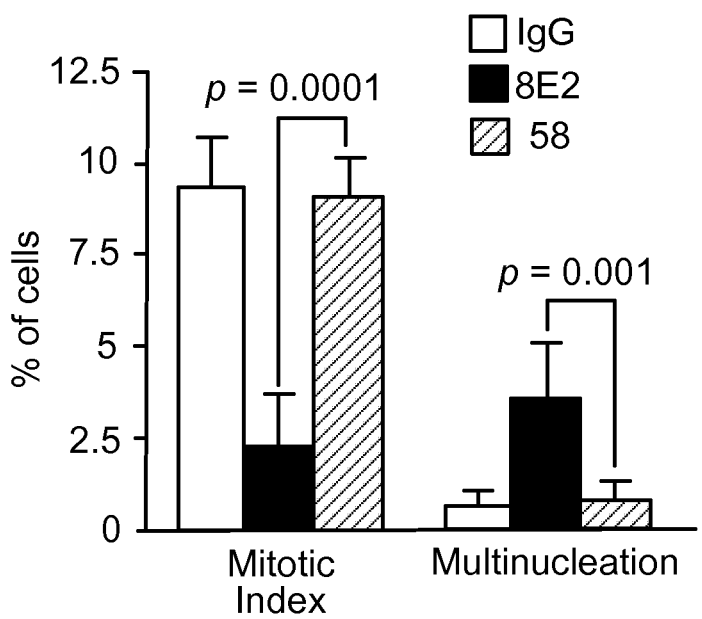
FIG. 9E is a graph quantifying the mitotic defects in cells loaded intracellularly with mAbs 8E2, mAb 58, or IgG.

Antibody Disruption of the Survivin-Hsp90 Interaction Results in Induction of Apoptosis and Mitotic Defects, In Vivo FIG. 9A shows that mAb 8E2 induces caspase-9 cleavage, a marker of apoptosis. For these experiments, YUSAC-2 melanoma cells stably transfected with a conditional expression system for wild type Survivin (Tet-Off system) were used. Conditional expression of Survivin was induced by removal of tetracycline from the culture medium as described in Grossman et al. (2001) *Proc. Nat'l Acad. Sci. USA*, 98:635. YUSAC-2 cells loaded intracellularly with mAb 8E2 or IgG using the BioPORTER™ protein transfection system (as described in Example 8) were analyzed for caspase-3/7 activity by caspase substrate incorporation and flow cytometry in the absence (Tet–) or presence (Tet+) of tetracycline. This assay stains for two parameters: caspase activity for hydrolysis of the fluorescent caspase substrate (X-axis) and loss of plasma membrane integrity by propidium iodide staining in non-permeabilized cells. See Kim et al., (2003) *Lancet*, 362: 205. Data are mean±S.D. of three independent experiments. The inset shows proteolytic processing of caspase-9 in HeLa cells transduced with mAbs 8E2 or 58 to Survivin. Positions of proform or cleaved caspase-9 visualized by Western blot are indicated. These data indicate that mAb 8E2 induced caspase 9 cleavage.

FIG. 9B shows that loading of mAb 8E2 into HeLa cells caused mitotic defects that were visualized by fluorescence microscopy. HeLa cells loaded with mAbs 8E2 or 58 to Survivin or IgG (negative control) were stained with an antibody to β-tubulin and analyzed by fluorescence microscopy. Arrows in FIG. 9B indicate multinucleated cells in mAb 8E2-transduced cultures, consistent with the induction of apoptosis-mediated cell death in these cells.

FIG. 9C summarizes the mitotic defects in cells loaded intracellularly with mAbs 8E2, mAb 58, or IgG. Mitotic index measures the percentage of cells undergoing mitosis, and was calculated by counting mitotic HeLa cells at 400× magnification in at least 5 fields containing an average of 100 cells/each. Data are the mean±standard error of the mean (SEM) of four independent determinations. HeLa cells loaded with mAb 8E2 displayed statistically significant differences in both mitotic index and multinucleation, indicative of apoptosis induction.

These results indicate that antibodies can be used to disrupt Survivin-Hsp90 protein-protein interactions and thereby induce apoptosis in cancer cells.

Example 10

Interaction of the Survivin Peptide Sequence 79-90 and Related Sequences with Hsp90

Figure 10A:
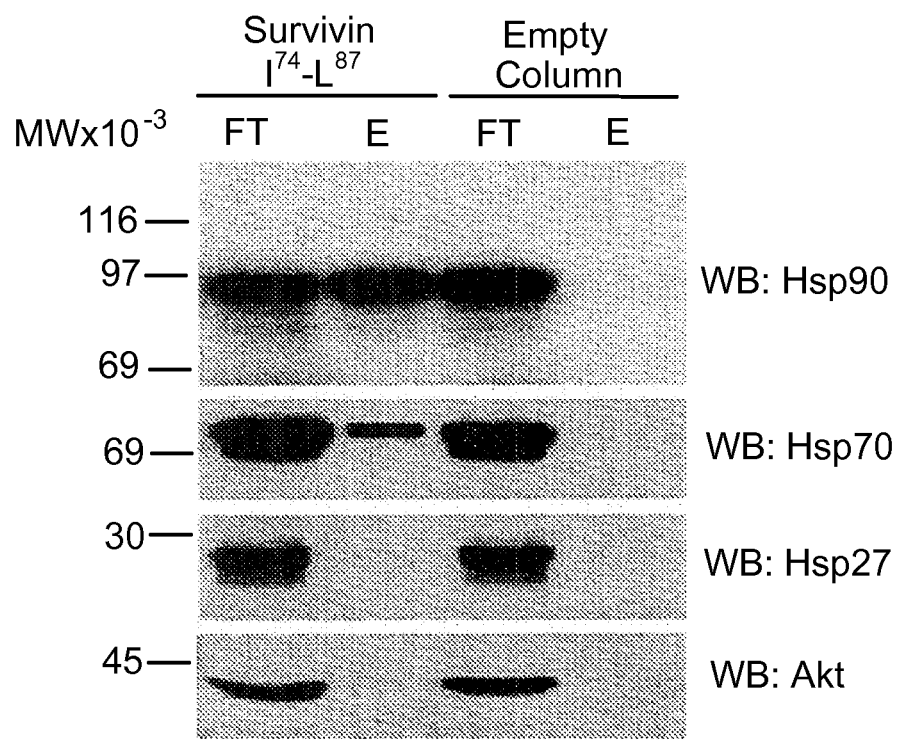
FIG. 10A is an immunoblot showing the results of affinity chromatography experiments. The immunoblots indicate that Hsp90 and Hsp70 and associated protein Akt bound to the indicated Survivin peptide (Ile74-Leu87) affinity column, but Hsp 27 did not bind to the Survivin peptide column.

FIG. 10A shows the isolation of a Hsp90/Hsp70 complex by affinity chromatography on a Survivin peptide column. A Survivin $Ile^{74}$-$Leu^{87}$ peptide (SEQ ID NO:4) containing a binding site for Hsp90 was immobilized onto a Sulfolink™ Coupling Gel (Pierce, Rockport, Ill.), and used to fractionate Raji cell extracts. Proteins were identified in the flow trough (FT) or eluate (E) by Western blotting with the indicated antibodies. Hsp90 and Hsp70 clearly bound the Survivin peptide including residues $Ile^{74}$-$Leu^{87}$. The anti-Hsp70 antibodies were obtained from Abcam, Cambridge, Mass. (cat. No. ab6535).

Figure 10B:
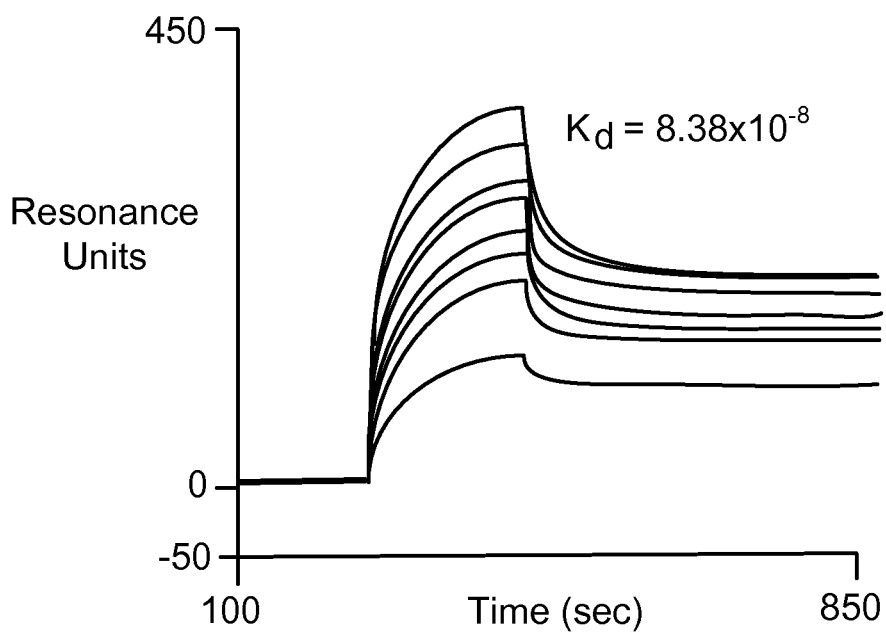
FIG. 10B is a graph showing the association of a Survivin peptide (Ile74-Leu87) containing the Hsp90 binding site with Hsp90 as measured by plasmon resonance.

FIG. 10B shows the physical association of the Survivin peptide sequence containing the Hsp90 binding site with Hsp90, as measured by plasmon resonance. Wild type Survivin peptide 77 to 91 (SEQ ID NO:22) or the corresponding C84A mutant 77-91 peptide (HKKHSSGAAFLSVKK; SEQ ID NO:23) was synthesized with an N-terminal biotin and immobilized on streptavidin coated chips (SA5) purchased from Biacore Inc. (Piscataway, N.J.). Increasing concentrations (100 nM-10 μM) of purified r-Hsp90 suspended in 10 mM HEPES, 150 mM NaCl, 3 mM EDTA, 0.005% polysorbate-20, 1 mM DTT, were then injected in 60 ml over the immobilized peptides. A constant flow rate of 20 ml/min was maintained, and the dissociation phase was followed for 300 seconds. Surfaces were regenerated using 10 ml of 1 M NaCl/50 mM NaOH after each dissociation phase. A new injection cycle was initiated only after 10 min post-regeneration to ensure complete removal of NaCl and NaOH. The collected data were analyzed using the Biaeval 3.0 software package from Biacore Inc.

Sensorgrams (FIG. 10B) indicate binding of the Survivin peptides to Hsp90, measured by an increase in surface plasmon resonance during analyte flow over the chip surface, with the nonspecific signal from the biotin-only surface subtracted. Whereas the on-rates for the wild type (SEQ ID NO:22) or C84A (SEQ ID NO:23) peptide were similar, the off-rates for the wild type peptide were 10 fold slower, resulting in a higher binding affinity (KD±SEM=$8.38×10^{-8}$±$3.5×10^{-9}$ M).

Figure 10C:
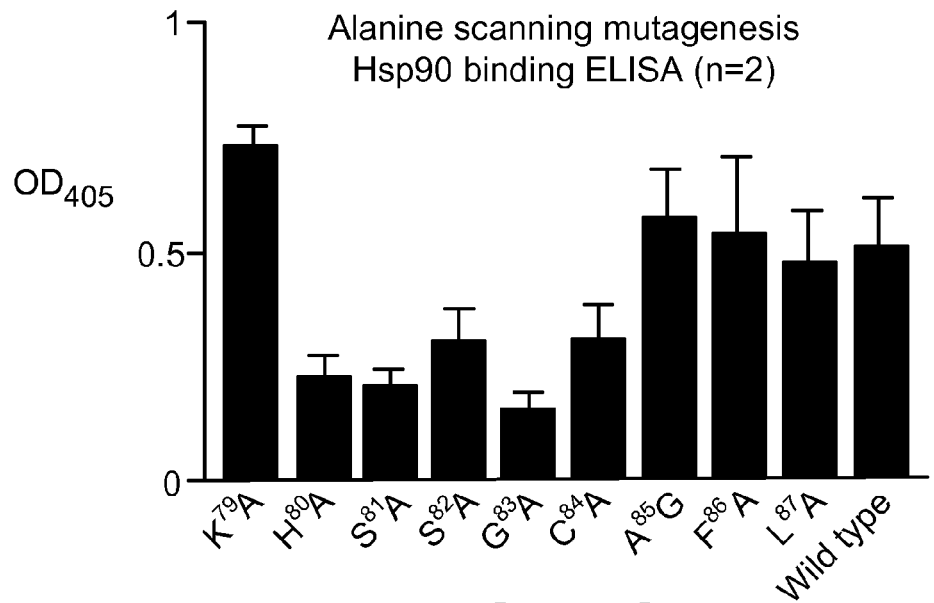
FIG. 10C is a graph showing the effects of alanine scanning mutagenesis on the ability of a Survivin peptide (K79-L87) to bind to Hsp90 as quantitated by ELISA experiments. Each indicated Survivin peptide mutant was immobilized on a microtiter plate and tested for the ability to bind to Hsp90.

FIG. 10C shows a functional analysis of mutagenized Survivin peptides for identification of the amino acids necessary for the Survivin-Hsp90 interaction (His 80-Cys 84; SEQ ID NO:2). Indicated synthetic peptides from the Survivin core sequence Lys 79-Leu 87 (SEQ ID NO:24) were synthesized carrying single alanine substitutions at each indicated position (alanine scanning mutagenesis). Individual peptides were immobilized at indicated increasing concentrations on plastic microtiter plates, incubated with recombinant Hsp90, and binding to the various substrates was determined with an antibody to Hsp90 by ELISA and quantified by absorbance at $OD_{405}$. Data are the mean±S.D. of two independent experiments, and demonstrate that the amino-terminal amino acids of the core Survivin sequence His 80, Ser 81, Ser 82, Gly 83 and Cys 84 are important for Hsp90 binding. In contrast, no differences were observed between the wild type peptide sequence and alanine substitutions of the residues flanking this sequence, Lys 79, Ala 85, Phe 86, and Leu 87.

These results indicate that the peptides disclosed herein bind to Hsp90, and identify amino acid residues necessary for the interaction.

Example 11

Development of Cell Permeable Peptides Based on the Survivin Binding Site for Hsp90 Located at K79-L87

For multiparametric analysis of caspase-dependent cell death and loss of plasma membrane integrity, HeLa, MCF-7, or genetically engineered HCT 116 cells (obtained from ATCC) were loaded with increasing concentrations of cell permeable control scrambled peptide or the Survivin peptide, harvested after culturing for 24 hours at 37° C., and analyzed for cell viability (propidium iodide, red channel) and active caspase-3 activity (CaspaTag™ from Intergen, Purchase, N.Y., green channel) by flow cytometry.

Figure 11A:
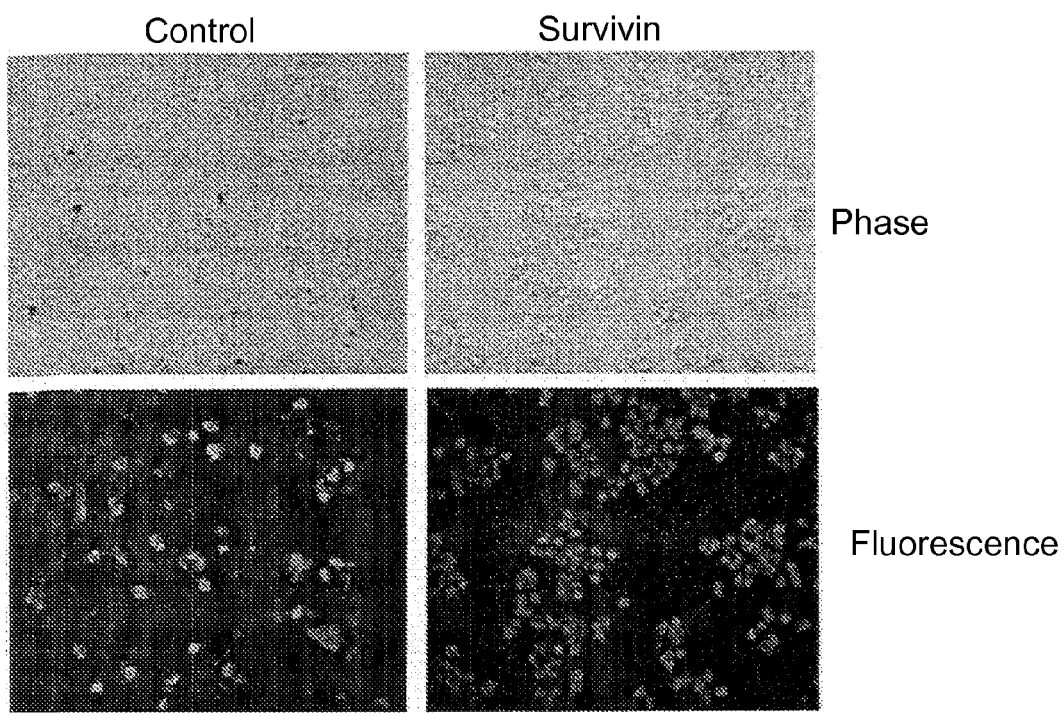
FIG. 11A is micrograph showing phase contrast and fluorescence microscopy images of cells incubated with cell-permeable versions of a Survivin peptide (Survivin) and scrambled control peptide (Control). In each pair of bars, the left bar represents Survivin and the right bar represents Control.

Cell permeable peptide was synthesized by fusing the third α-helix of the Antennapedia carrier sequence to the amino-terminus of the Survivin peptide sequence K79-L87, containing the Hsp90 binding site (Survivin cell permeable peptide) to create the P31 survivin peptide (SEQ ID NO:19; See FIG. 21). A control peptide carrying an Antennapedia permeabilizing peptide (RQKIWFQNRRMKWKK; SEQ ID NO:29) fused to a Survivin K79-L87 sequence in scrambled order (Control) was also synthesized (RQIKIWFQNRRMK-WKKKSKLACFSHG; SEQ ID NO:25). Both Control and Survivin peptides were synthesized with an amino-terminal biotin moiety and were analyzed by HPLC for purity and homogeneity. Peptides were incubated at 150 μM final concentration with subconfluent HeLa cells for 6 hours at 37° C. Cells were harvested, stained with streptavidin-PE, and analyzed by phase contrast (Phase) or fluorescent microscopy. FIG. 11A shows efficient internalization of both Survivin peptide (SEQ ID NO:19) and the scrambled control peptide (SEQ ID NO:25).

Figure 11B:
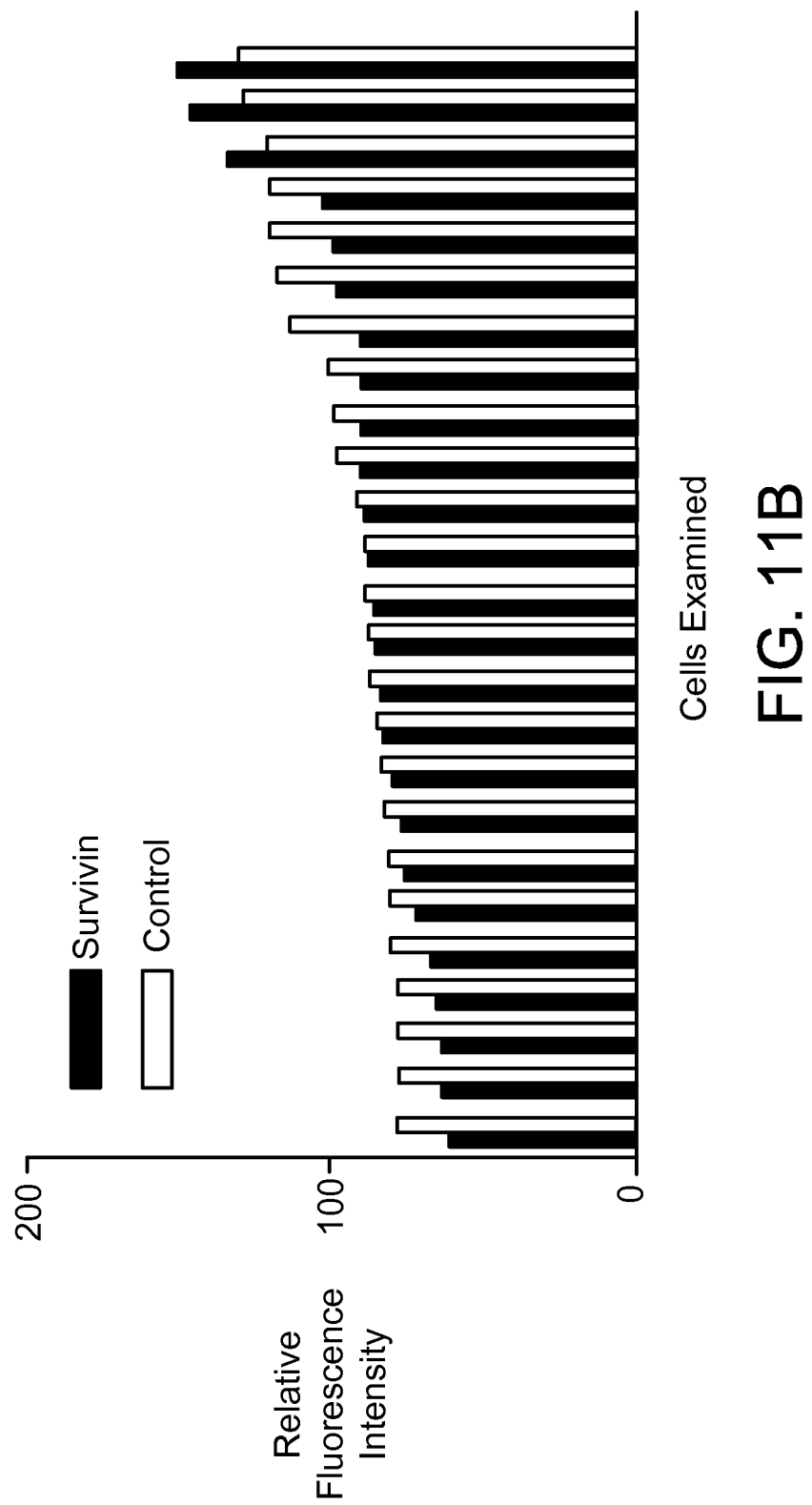
FIG. 11B is a graph quantifying the results of experiments depicted in FIG. 11A, confirming that Control and Survivin peptides were efficiently internalized into cells.

FIG. 11B quantifies the observations of FIG. 11A by analyzing the fluorescence of individual cells. Experimental conditions are as described for FIG. 11A, except that intracellular penetration of control or Survivin peptides was analyzed in 25 individual cells by fluorescence microscopy. Thirteen optical sections (333±50 nm) were acquired using wide field fluorescence microscopy (Olympus, JAPAN) and a 63× objective from 6 random fields. For individual cell measurements, fluorescence values of areas outside the cell contours were obtained and subtracted as background from the total value (typically 5-10% of total cellular fluorescence). Fluorescence intensity (integrated optical density, IOD) for every optical section in every full cell profile or within an entire population was calculated using Metamorph™ software (Molecular Devices Corporation, Sunnyvale, Calif.) or IP Lab software (version 3.5.4, Scanalytics, Fairfax, Va.). The results demonstrate that both Control and Survivin cell permeable peptide variants accumulate inside the target cells with indistinguishable penetration efficiency.

These results demonstrate the synthesis of novel cell permeable Survivin peptide derivatives.

Example 12

Survivin Cell-Permeable Peptide Duplicates Hsp90 Binding Site Induces Apoptosis in Tumor Cells For determination of apoptosis by hypodiploid DNA content, various tumor cell lines were incubated with increasing concentrations of the cell permeable control scrambled (SEQ ID NO:25) or Survivin peptide (SEQ ID NO:19), harvested after 24 hours (floaters plus attached cells) fixed in 70% ethanol, and stained with 10 μg/ml propidium iodide plus 100 μg/ml RNAse A and 0.05% Triton™ X-100 in PBS, pH 7.4. Cultures were analyzed for DNA content by flow cytometry. For colorimetric quantification of cell viability, an MTT assay was used. Various tumor cell lines were incubated with increasing concentrations of the cell permeable retro-inverso control scrambled P4 or the Survivin-specific P3 peptide, incubated for 24 hours at 37° C. washed twice with Bruffs Media, and 4,5-dimethylthiazol-2-yl)-2,5-diphenyltetrazolium bromide (MTT) (Sigma, St. Louis, Mo.) was added at 5 mg/ml. Decrease in cell viability was analyzed for loss of colorimetric absorption at $OD_{405}$.

Figure 12A:
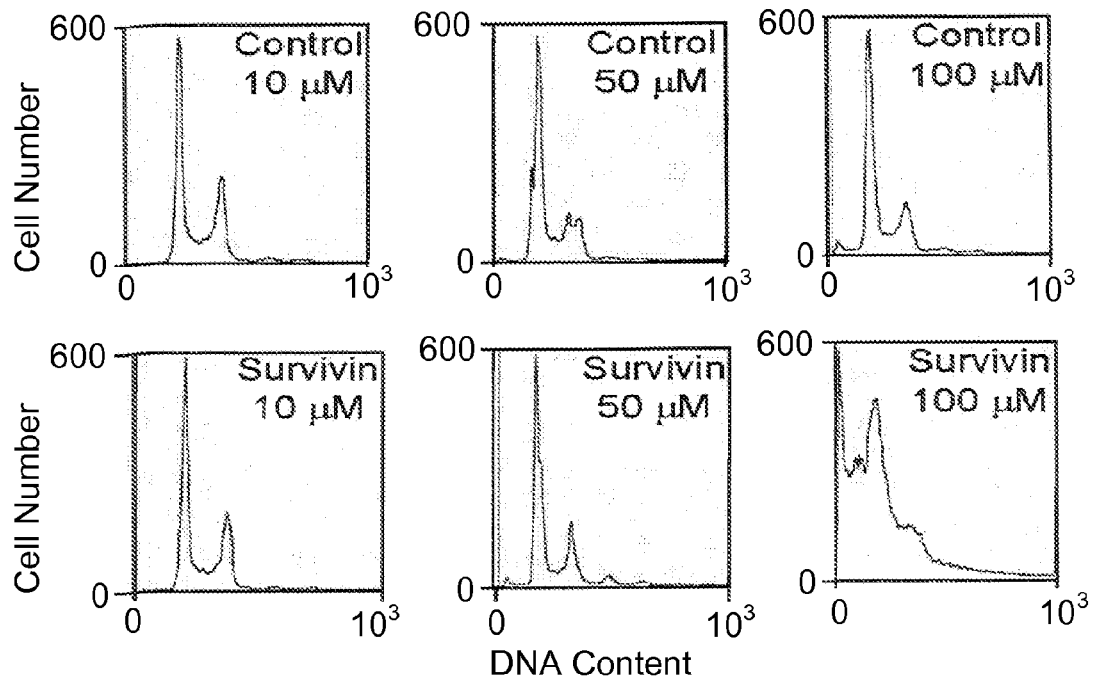
FIG. 12A is a graph documenting the results of flow cytometry experiments on cells exposed to indicated concentration of cell permeable versions of a Survivin peptide or scrambled control peptide. The results indicate that Survivin cell-permeable peptide induced apoptosis.

FIG. 12A shows that the Survivin cell permeable peptide (SEQ ID NO:19) induces apoptosis in HeLa cells, as measured by hypodiploid DNA content. HeLa cells were incubated with the indicated increasing concentrations of the cell permeable Control (scrambled) or Survivin peptide, harvested after 24 hours at 37° C., and analyzed by hypodiploid DNA content by propidium iodide staining and flow cytometry. Exposure of HeLa cells to the Survivin cell permeable peptide resulted in massive loss of cell viability as reflected by an increase in hypodiploid DNA content.

Figure 12B:
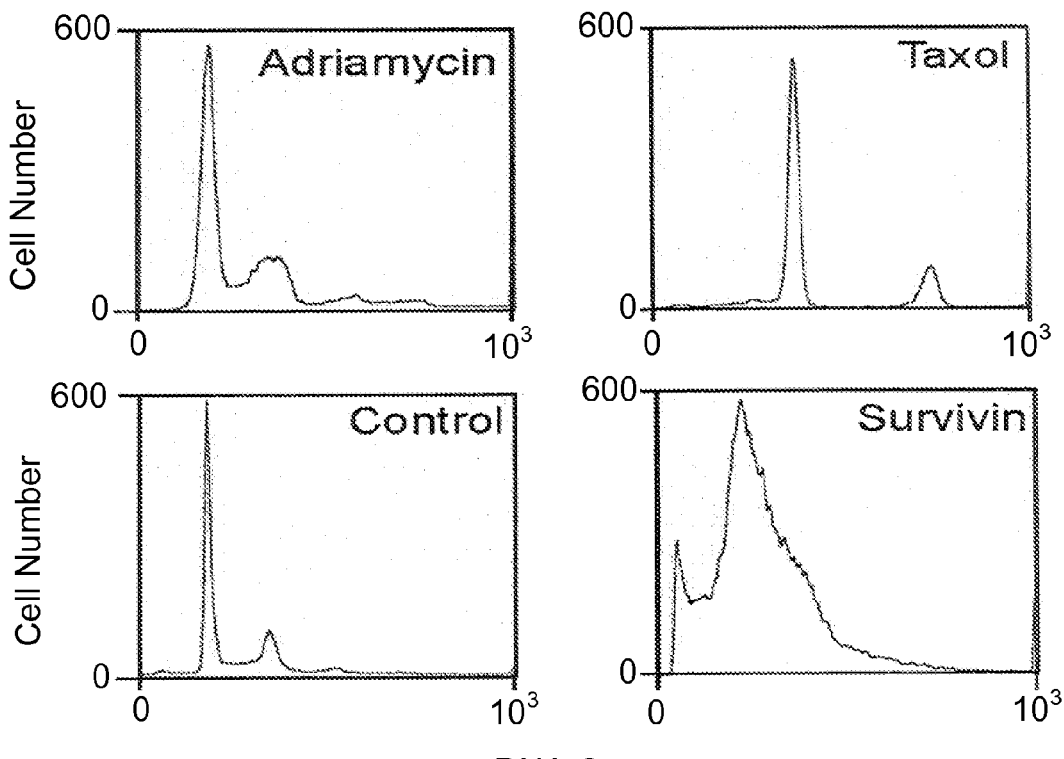
FIG. 12B is a graph comparing the abilities of Survivin cell permeable peptide and indicated chemotherapeutics to induce apoptosis as measured by flow cytometry. Results indicated that Survivin cell permeable peptide was more effective at inducing apoptosis than the chemotherapeutics.

FIG. 12B shows the comparison of the Survivin cell permeable peptide (SEQ ID NO:19) with established chemotherapeutic drugs. HeLa cells were incubated with chemotherapeutic drugs Taxol™ (10 μM) or adriamycin (300 nM), or cell permeable control peptide or the Survivin peptide, harvested after 24 hours, and analyzed for induction of apoptosis by hypodiploid DNA content by flow cytometry. Treatment with the indicated concentrations of the two chemotherapeutic drugs does not result in significant loss of cell viability. In contrast, intracellular penetration of the Survivin cell permeable peptide, but not control peptide, results in the appearance of a large cell population with hypodiploid DNA content (apoptotic).

These results indicate that a cell-permeable peptide derivative disclosed herein induced apoptosis in cancer cells.

Example 13

Figure 13:
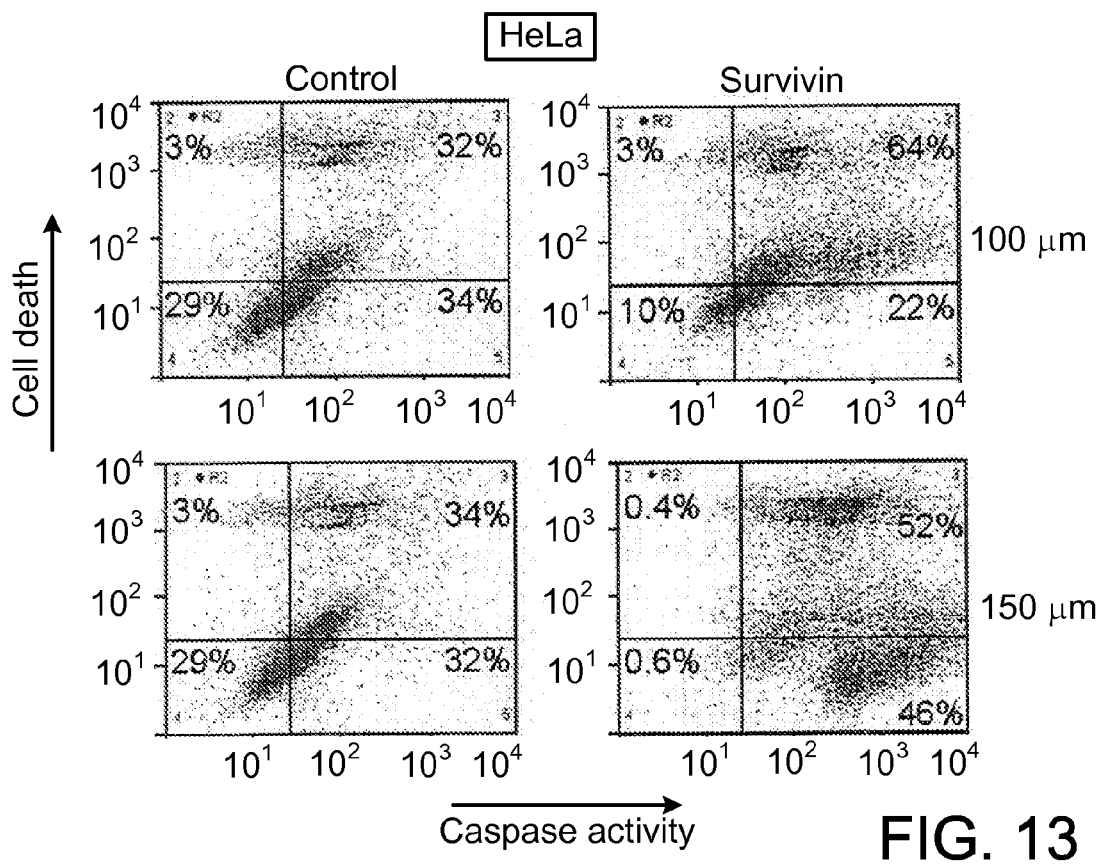
FIG. 13 depicts multiparametric flow cytometry results quantifying caspase activity (indicative of apoptosis) in the X-axis and loss of plasma membrane integrity (indicative of cell death) in the Y axis. The results show that Survivin cell permeable peptide induces cell death more efficiently than scrambled control peptide in HeLa cells.

The Cell Permeable Survivin Peptide Sequence Induces Caspase-Dependent Apoptosis in Cervical Carcinoma HeLa Cells FIG. 13 shows the induction of caspase activity in HeLa cells (with non-functional p53) incubated with the indicated increasing concentrations of Control (SEQ ID NO:25) or Survivin (SEQ ID NO:19) cell permeable peptides. Cells were harvested after 24 hours of incubation with peptide and simultaneously analyzed for caspase activity by DEVDase activity (X-axis, green fluorescence) and cell membrane integrity by propidium iodide staining (Y-axis, red fluorescence). Cells in the upper right quadrant correspond to the population with elevated caspase activity and loss of cell membrane integrity (apoptotic).

These results indicate by additional means that a peptide derivative disclosed herein induced apoptosis in cancer cells.

Example 14

Figure 14:
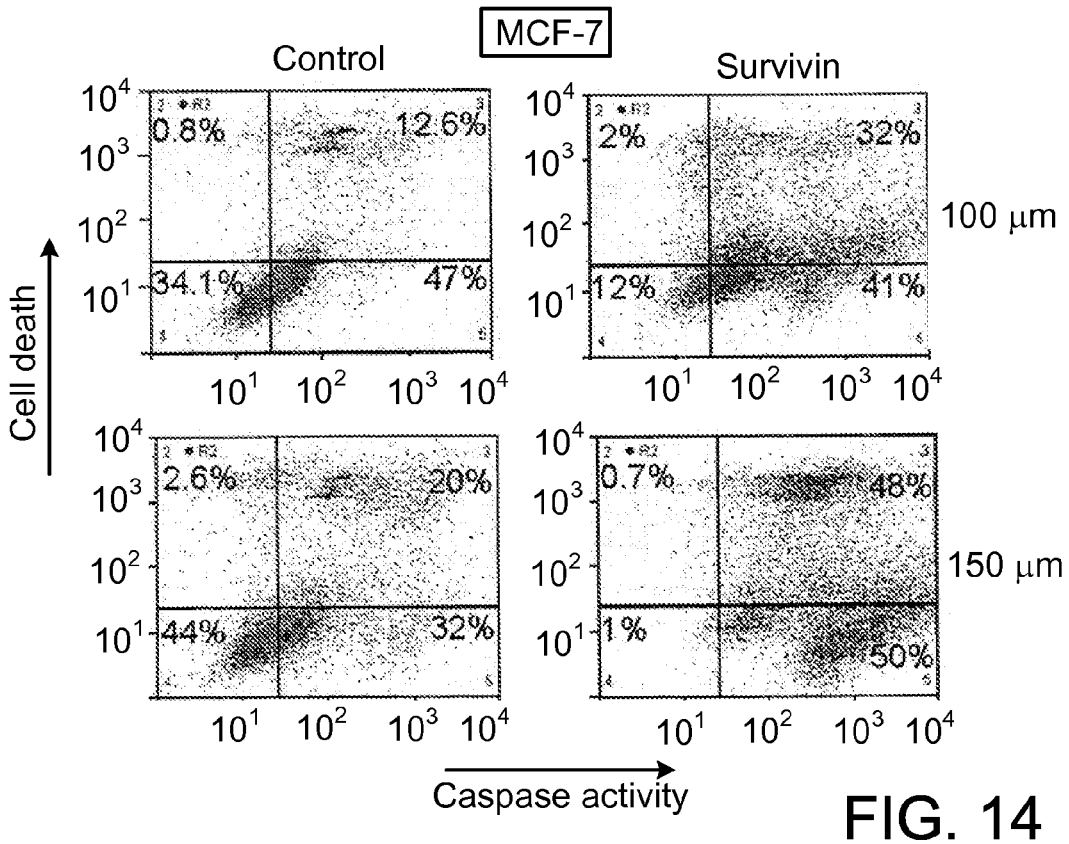
FIG. 14 depicts multiparametric flow cytometry results quantifying caspase activity (indicative of apoptosis) in the X-axis and loss of plasma membrane integrity (indicative of cell death) in the Y axis. The results show that Survivin cell permeable peptide induces cell death more efficiently than scrambled control peptide in MCF-7 cells.

Cell-Permeable Survivin Peptide Induces Caspase-Dependent Apoptosis in Breast Carcinoma MCF-7 Cells Experiments were performed as in Example 13, except that breast carcinoma MCF-7 cells (wild type p53) were analyzed by multiparametric flow cytometry of induction of caspase activity and loss of cell membrane integrity after intracellular loading with cell permeable Control (SEQ ID NO:25) or Survivin (SEQ ID NO:19) cell permeable peptide. The results shown in FIG. 14 demonstrate that the Survivin cell permeable peptide induces apoptosis in different tumor cell types (HeLa and MCF-7) with comparable efficiency and similar mechanism (caspase-dependent).

These results indicate by additional means that a peptide derivative disclosed herein induced apoptosis in more than one type of cancer cell.

Example 15

Apoptosis of Tumor Cells Induced by Cell Permeable Survivin Peptides is Independent of p53

Figure 15:
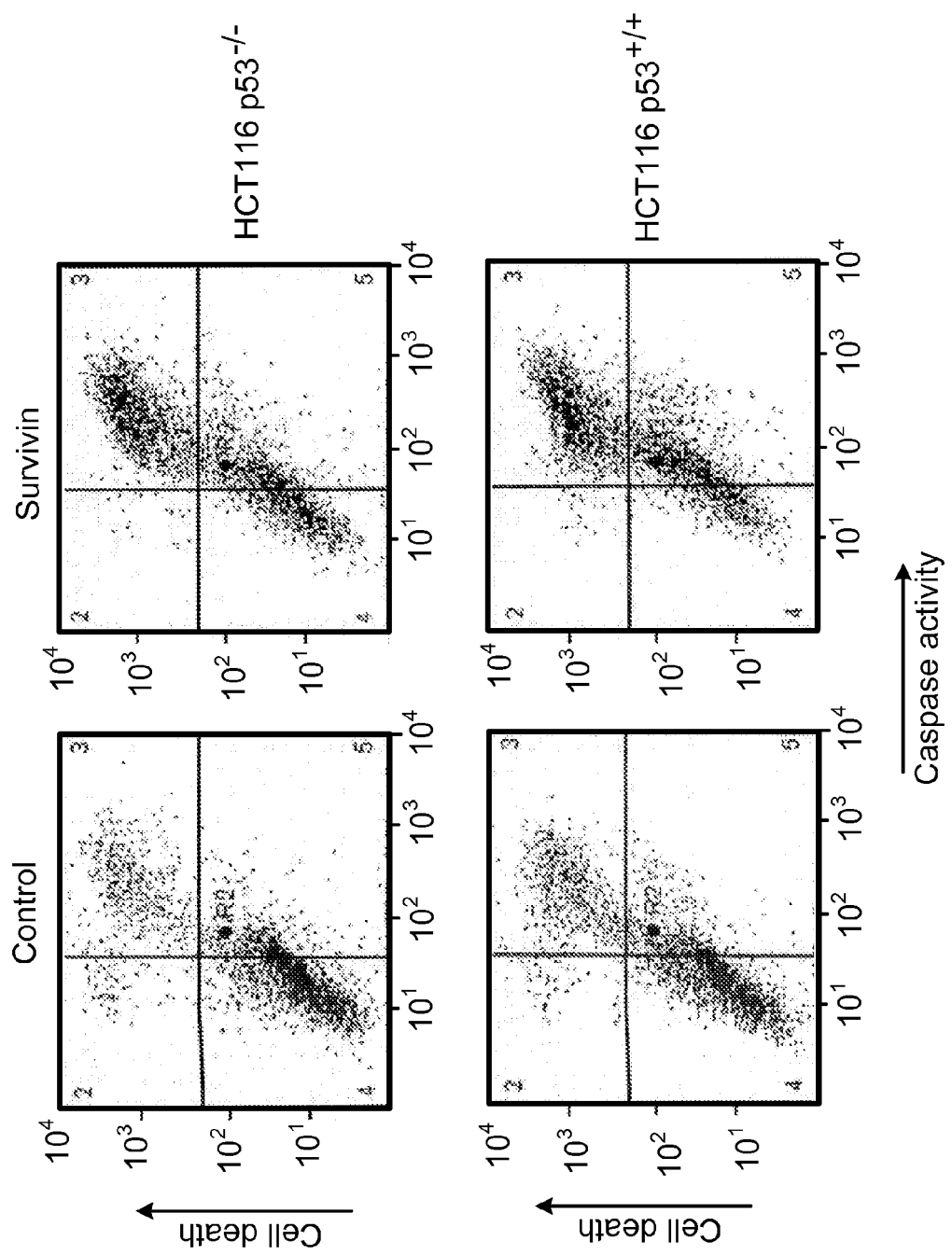
FIG. 15 depicts multiparametric flow cytometry results quantifying caspase activity (indicative of apoptosis) in the X-axis and loss of plasma membrane integrity (indicative of cell death) in the Y-axis. The results show that Survivin cell permeable peptide induces cell death more efficiently than scrambled control peptide in both HCT116 cells with wild type p53 alleles and in HCT116 cells with inactivated p53 alleles.

In these experiments, HCT116 colorectal cancer cells carrying wild type p53 ($p53^{+/+}$) or homozygously inactivated p53 ($p53^{-/-}$) (Bunz et al., Science, 282:1497-1501 (1998))) were incubated with 150 mM of cell permeable Control (SEQ ID NO:25) or Survivin (SEQ ID NO:19) cell permeable peptide, harvested after 24 hours and analyzed by multiparametric flow cytometry of induction of caspase activity and loss of cell membrane integrity. Results shown in FIG. 15 demonstrate that accumulation of cells with high caspase activity and loss of plasma membrane integrity by the cell permeable Survivin peptide is indistinguishable between $p53^{+/+}$ and $p53^{-/-}$ HCT116 cells. This demonstrates that p53 is not involved in mediating the apoptotic response induced by the Survivin cell permeable peptide in tumor cell types.

These results indicate by other means that a peptide derivative disclosed herein induced apoptosis in more than one type of cancer cell, and that apoptosis was not dependent on p53.

Example 16

Intracellular Penetration of the Cell Permeable Survivin Peptide Results in Inhibition of Hsp90 Function with Degradation of Hsp90 Client Proteins and Activation of Caspase Activity To determine whether intracellular loading of the Survivin cell permeable peptide reproduced the effect of mAb 8E2 that disrupts the Survivin-Hsp90 interaction in destabilizing Survivin levels in vivo (FIG. 8), HeLa cells were loaded with the indicated increasing concentrations of cell permeable control (SEQ ID NO:25) or Survivin (SEQ ID NO:19) cell permeable peptide, harvested after 24 hours, and analyzed for stability of Hsp90 client proteins, Survivin and Akt. Polyclonal antibody to Akt was obtained from Cell Signaling Technology (Cat. No. 9272).

Figure 16:
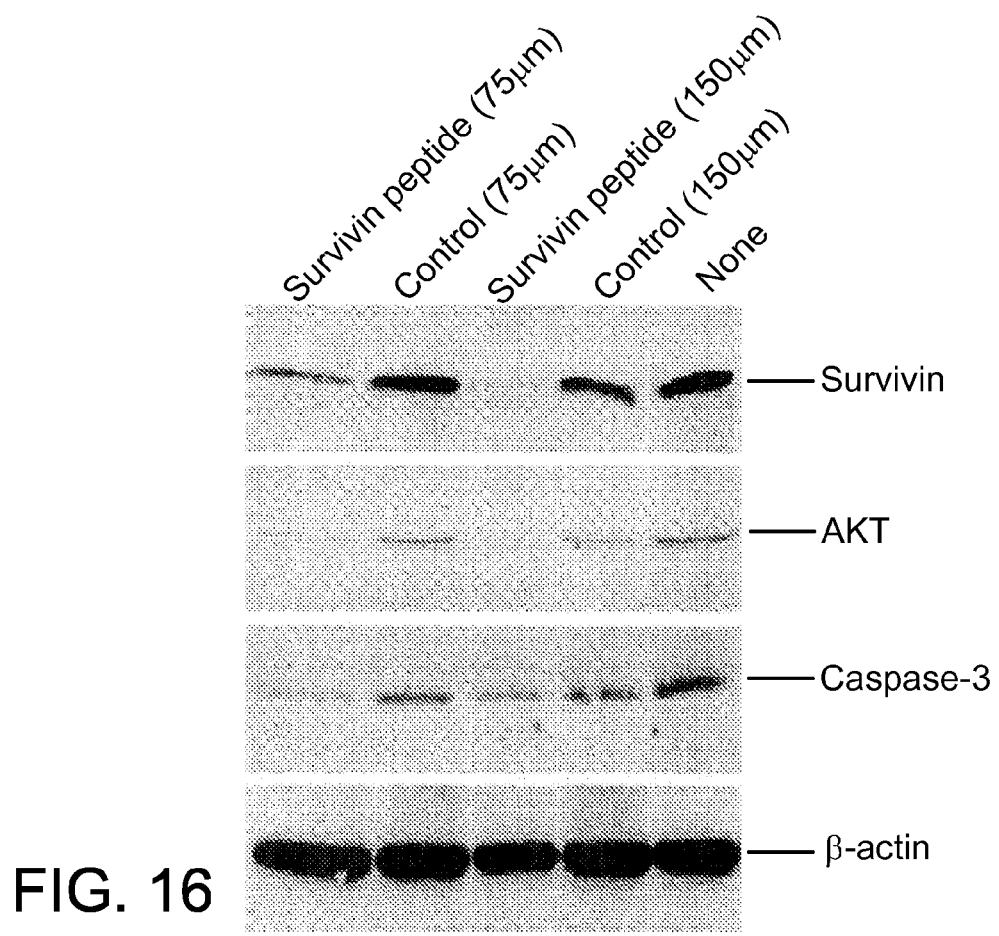
FIG. 16 is an image of an immunoblot of cell extracts from cells loaded with increasing concentrations of Survivin cell permeable peptide or scrambled cell permeable control peptide. The immunoblots show that Survivin cell permeable peptide decreased the expression (stability) of Survivin and AKT.

The Western blot data in FIG. 16 demonstrate that Survivin cell permeable peptide results in low levels of Survivin and Akt, whereas the control scrambled peptide is ineffective. In addition, Survivin cell permeable peptide results in loss of expression of caspase-3 proform of 32 kD, indicative of proteolytic caspase activation and consistent with caspase-dependent cell death. No changes in caspase-3 proform expression were observed with the cell permeable control scrambled peptide. β-actin was used to normalize for loading.

These results indicate that a peptide derivative disclosed herein inhibited Survivin-Hsp90 protein-protein interactions, thereby reducing expression of Survivin and bringing about caspase-dependent apoptosis in cancer cells.

Example 17

Generation and Characterization of Peptidomimetic Variants of the Active Survivin Peptide Sequence K79-L87

Figure 17:
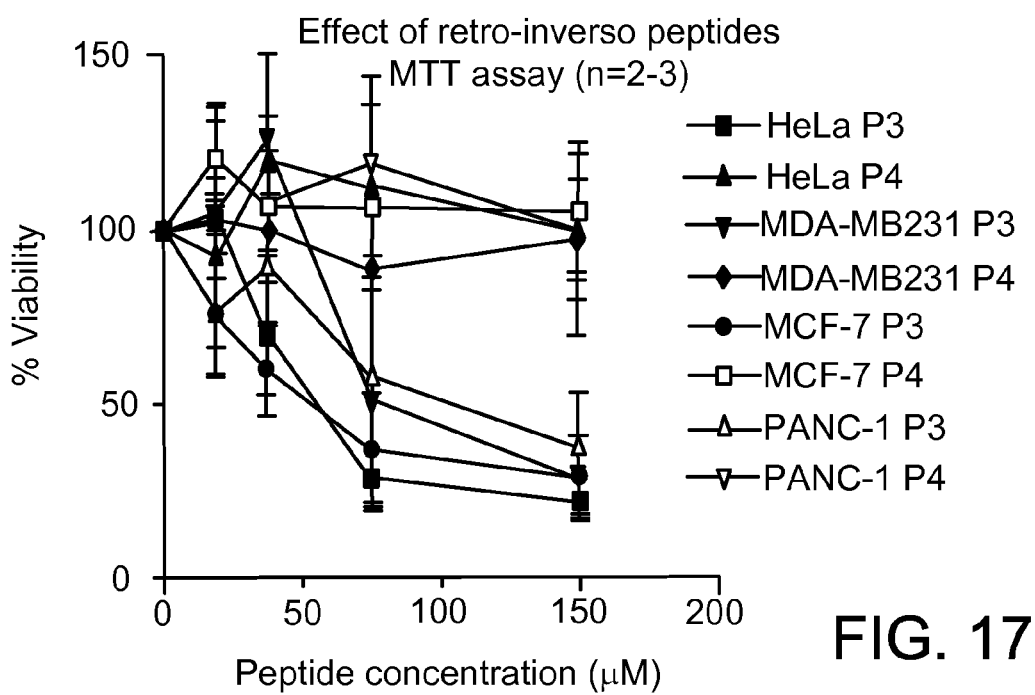
FIG. 17 is graph comparing the effect of increasing concentrations of a retro-inverso Survivin cell permeable peptide (P3) and control peptide (P4) on the cell viability of the indicated tumor cell lines (HeLa, MDA-MB231, MCF-7, and PANC-1).

To increase the stability in vivo of the cell permeable Survivin K79-L87 sequence, we synthesized peptidomimetic variants in which the cell penetrating Antennapedia sequence and the Survivin active sequence K79-L87 were synthesized using D-amino acid (retro sequence) and in the reverse order (inverso sequence). Both the control scrambled and Survivin peptide sequences were synthesized as retro-inverso variants and designated P3 (Survivin; KKWKMRRNQFWVKVQR-LFACGSSHK-CONH$_2$) and P4 (control scrambled; KKWK-MRRNQFWVIWQRGHSFCALKS-CONH$_2$) peptides (See FIG. 21). To test the ability of the retro-inverso cell permeable sequences to induce apoptosis in cancer cells, a panel of tumor cell lines were analyzed by the cell viability MTT assay after incubation with the indicated increasing concentrations of the P3 (Survivin) or P4 (control) retro-inverso cell permeable peptides. The data in FIG. 17 show that the P3 sequence induced dose-dependent loss of cell viability in all the tumor cell lines tested (HeLa: cervical carcinoma; MDA-MB231 (Calvo et al., Br. J. Cancer, 48:683-8 (1983)): breast carcinoma; MCF-7: breast carcinoma; PANC-1 (obtained from ATCC): pancreatic carcinoma. P3 activity was independent of p53 status. In contrast, there was no decrease in cell viability in any of the cell types tested at the same increasing concentrations of the cell permeable retro-inverso control P4 peptide.

These results indicate that a retro-inverso peptide derivative disclosed herein caused apoptosis in several different types of cancer cells.

Example 18

Peptidomimetic Variant of Survivin K79-L87 Sequence (P3) has Specific Anti-Tumor Activity Against Broad Range of Tumor Cell Types without Affecting the Viability of Normal Cell Types To study the specificity of the retro-inverso P3 and P4 sequences described in Example 17, we incubated a variety of tumor cell lines with the cell permeable retro-inverso P3 and P4 peptides (150 μM), and stained the cultures after 24 hours by trypan blue (Sigma) exclusion. Cells that fail to exclude the blue dye were cells that lost cell viability and plasma membrane integrity.

Figure 18:
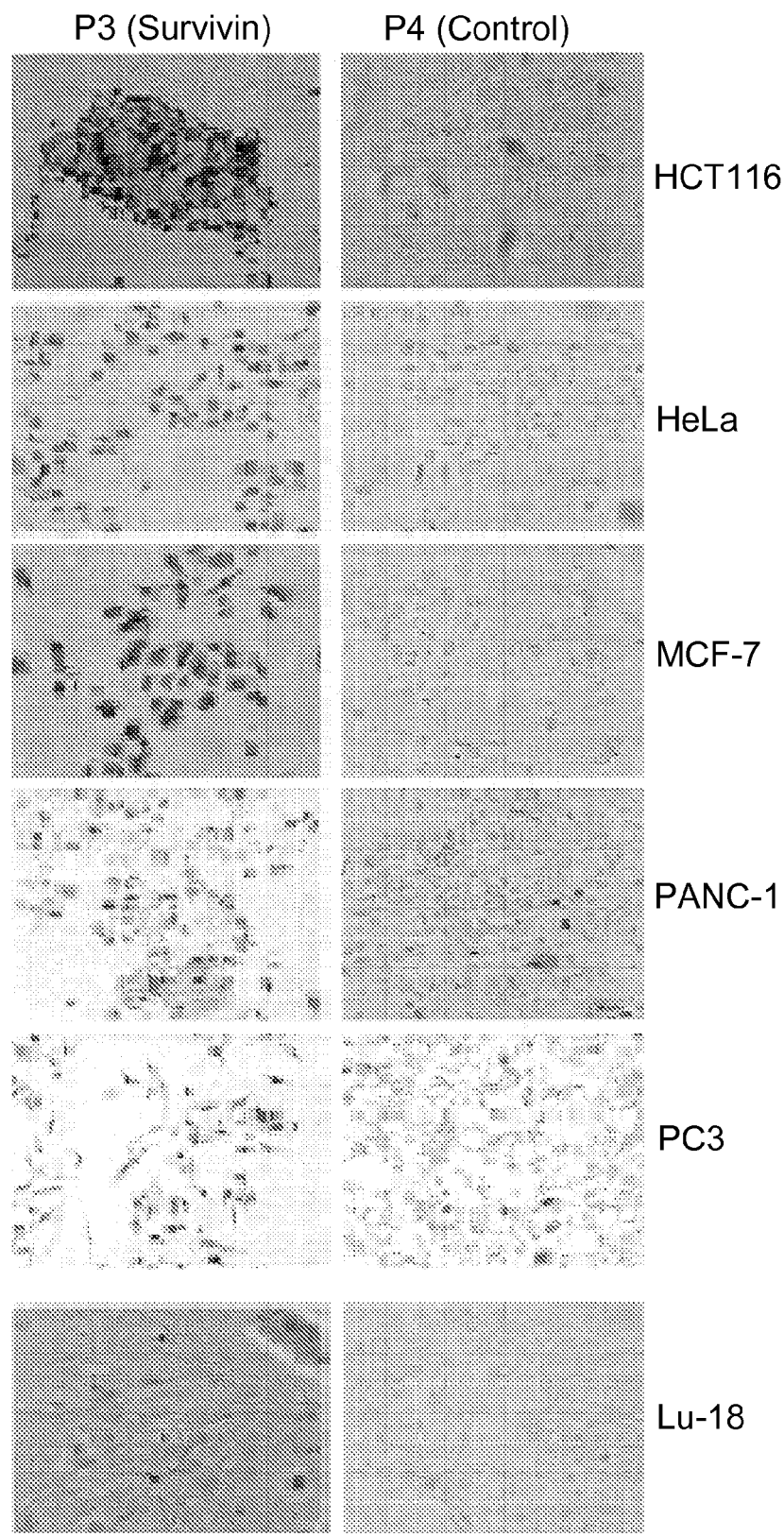
FIG. 18 is a series of microscopy images of indicated tumor cell lines treated with the retro-inverso Survivin cell permeable (P3) peptide or control (P4) peptide.

The results shown in FIG. 18 demonstrate that penetration of the P3 retro-inverso Survivin peptide results in rapid loss of viability in the vast majority of all tumor cells examined, HCT116 colorectal cancer, HeLa cervical carcinoma, MCF-7 breast carcinoma, PANC-1 pancreatic carcinoma, PC3 prostate cancer. On the other hand, comparable incubation reactions with the retro-inverso control peptide P4 did not reduce tumor cell viability. Furthermore, neither the Survivin P3 nor the control P4 peptide resulted in decreased viability of normal lung fibroblast LU18 cells, suggesting that the pro-apoptotic function of P4 is tumor-cell specific.

These results indicate that the broad anti-apoptotic activity of a retro-inverso peptide derivative disclosed herein was specific to cancer cells, and did not affect non-cancerous cells. The results support the notion that peptide derivatives disclosed herein can be used in therapeutic methods to treat subjects suffering from cancer.

Example 19

The P3 Peptide Inhibits In Vitro Tumorigenicity Measured by Anchorage-Independent Cell Growth and Survival For soft agar colony formation, $2 \times 10^4$ adapted breast carcinoma MCF-7 cells were suspended in 1.5 ml of DMEM supplemented with 10% FBS and 0.35% bactoagar (Becton Dickinson, Sparks, Md.) in 36 mm tissue culture plates containing 1.5 ml of 0.75% agarose in growth medium at the bottom layer. The plates were incubated at 37° C. in a 5% $CO_2$ incubator for 2-5 weeks. The colonies were stained with 0.005% crystal violet (Sigma) and counted using a dissecting microscope under high power field.

Figure 19:
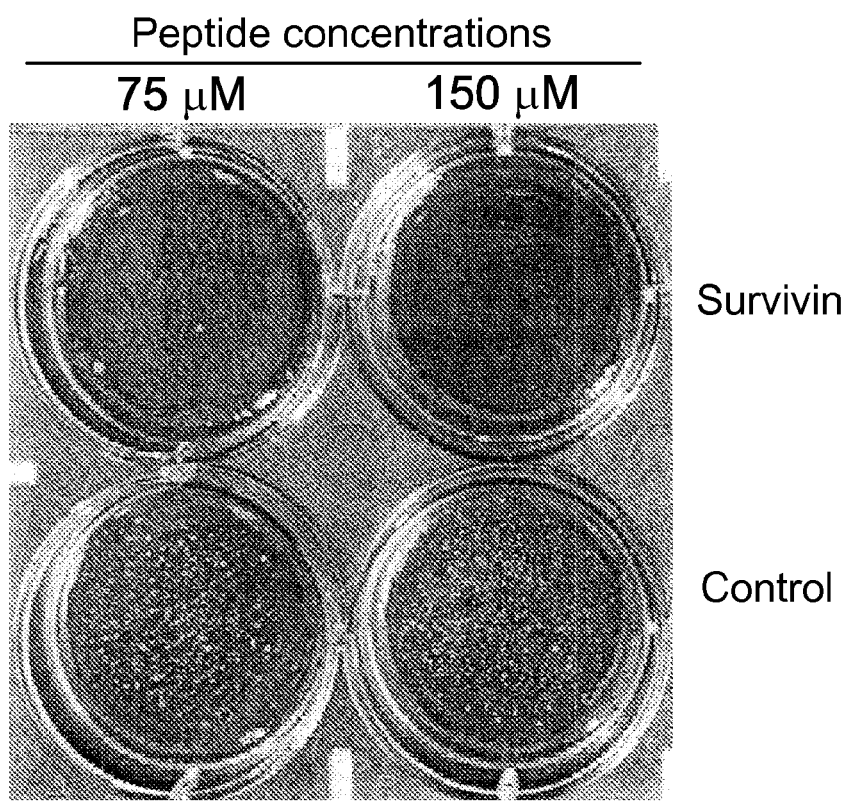
FIG. 19 is an image of a soft agar tissue culture plates on which ~20,000 breast carcinoma MCF-7 cells were suspended in media containing the indicated concentrations of P31 Survivin peptide or a control scrambled peptide.

FIG. 19 shows that presence of 75 or 150 μm of Survivin P31 peptide (SEQ ID NO:19) in growth media completely inhibited the anchorage-independent cell growth and survival of carcinoma cells (relative to equal amounts of Control scrambled peptide (SEQ ID NO:25)). The two upper plates shown in FIG. 19 had no visible cell colonies.

These results indicate that Survivin peptides containing the Survivin Hsp90-binding motif are highly effective inhibitors of tumor cell proliferation in vitro.

Example 20

Anti-Tumor Activity of the Retro-Inverso P3 Survivin Peptide, In Vivo

Figure 20:
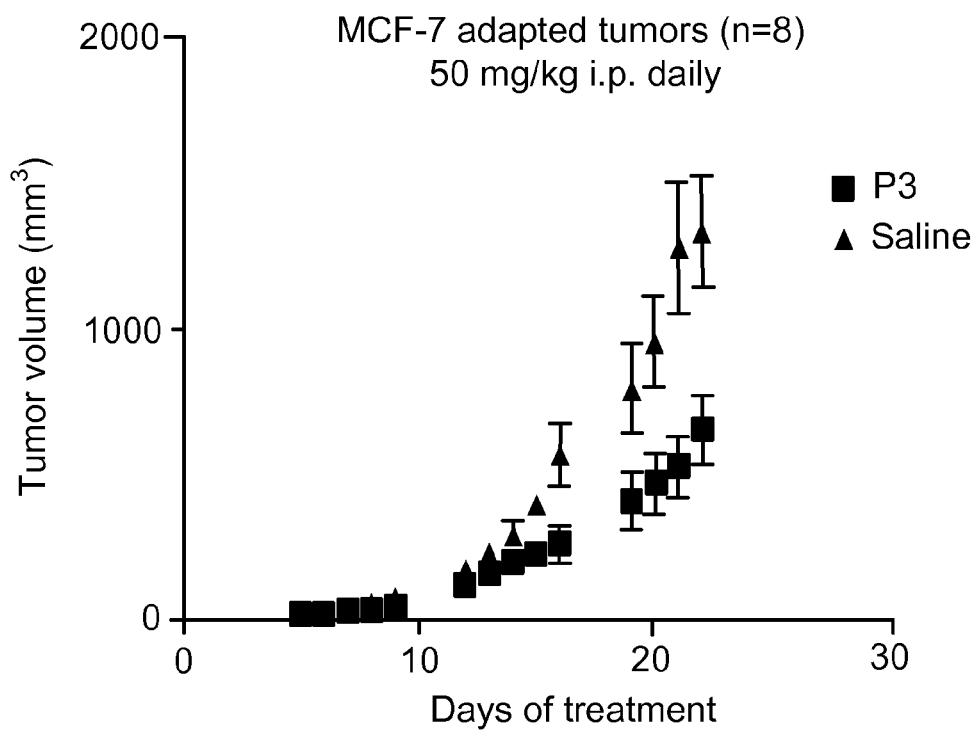
FIG. 20 is a graph recording the results of in vivo tumor formation experiments showing that Survivin cell permeable (P3) peptide was more effective than saline control in inhibiting tumor growth as measured by tumor volume (y-axis).

A breast carcinoma xenograft model was established by injecting MCF-7 cells in the flank of immunocompromised animals. Eight-week old female CB17 SCID/beige mice (Taconic Farms, Germantown, N.Y.) were injected subcutaneously into the flanks with $2.5 \times 10^6$ exponentially growing tumor adapted MCF-7 cells in 200 μl of sterile PBS, pH 7.4. Tumor growth was measured with a caliper in the two dimensions and tumor volume was calculated assuming a spheroid configuration with the formula Width×Length/2. Tumors were confined to local masses and did not affect animal survival over a 4-month observation period. When tumors reached ~50 mm$^3$ in size, animals were randomized (7 or 8 per group) and administered saline (once daily, 200 μl) or the retro-inverso P3 Survivin-derived peptidomimetic (50 mg/kg/i.p./day). Animals were sacrificed after 3 weeks of treatment. Tumor volume of animals treated with saline or the P3 peptide was measured daily with a caliper and animals were sacrificed after 21 days of treatment. The data in FIG. 20 show that P3 peptide slowed the rate of increase of tumor volume more effectively than saline over the treatment period.

In a second model, breast carcinoma MCF-7 cells previously adapted, in vivo were injected into SCID/beige mice. The injected cells generated rapidly exponentially growing tumors independent of estrogen supplementation and unaffected by saline administration (FIG. 28). Administration of the retro-inverso P3 Survivin-derived peptidomimetic (50 mg/kg/i.p./day) inhibited the growth of these more aggressive tumors throughout a 23-day (FIG. 28), or 11-day treatment period.

MCF-7 tumors recovered at the end of treatment were analyzed by immunohistochemistry for expression of Hsp90 client proteins (Ambrosini et al., *Nat. Med.*, 3:9177-21 (1997); Basso et al., *Oncogene*, 21:1159-66 (2002)). Tumors from the saline group exhibited extensive labeling for survivin and Akt in the tumor cell population. Conversely, Survivin peptide treatment nearly completely abolished Akt levels in tumor cells and severely attenuated expression of survivin.

These results indicate that Survivin peptides and peptide derivatives containing the Survivin Hsp90-binding motif are effective inhibitors of tumor cell proliferation in vivo.

Example 21

Survivin Peptide Induced Apoptosis is Tumor Cell Specific

Figure 22A:
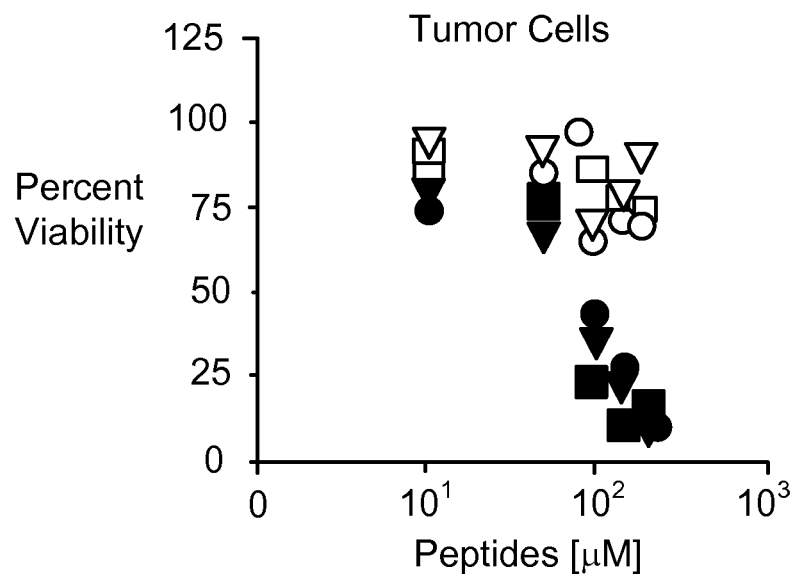
FIG. 22A and FIG. 22B are graphs showing the effect of Survivin peptide (P31; closed symbols) and control peptide (P33; open symbols) on apoptosis of tumor cell lines (FIG. 22A) and normal cell lines (FIG. 22B).
Figure 22B:
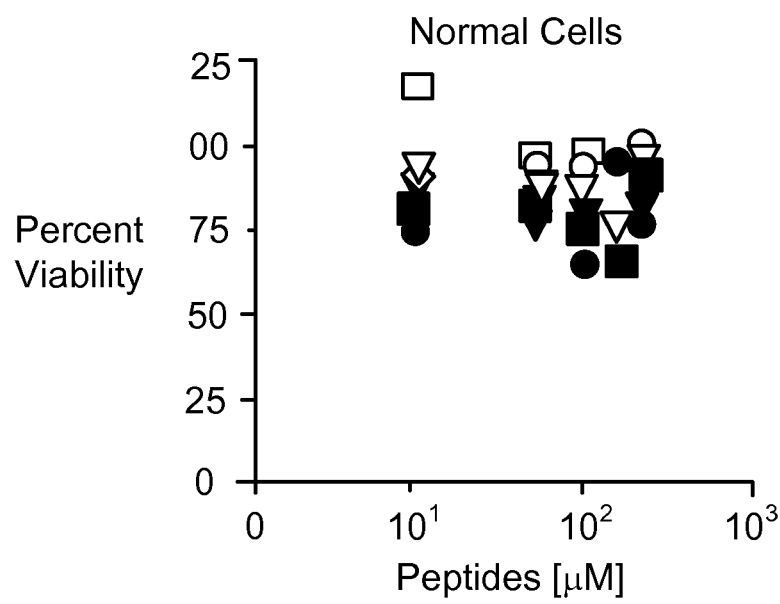

FIGS. 22A and 22B compares the effect of P31 (SEQ ID NO:19) or P33 (SEQ ID NO:25) on apoptosis of tumor cell lines (FIG. 22A) and normal cell lines (FIG. 22B). The following tumor cell lines DU145 (prostate cancer, circles), PC3 (prostate cancer, triangles), or HeLa (cervical carcinoma, squares) were treated with the indicated increasing concentrations of P31 peptide (solid symbols) or control P33 peptide (open symbols), harvested after 24 hours, and analyzed for cell viability using an MTT colorimetric assay. For normal cell types (right panel), HFF (human foreskin fibroblasts, squares), HGF (human fibroblasts, triangles) or WS-1 (human epithelial cells, circles) were treated with P31 (solid symbols) or control scrambled peptide P33, harvested after 24 hours and analyzed for overall cell viability by MTT colorimetric assay. All cell lines were from ATCC. The results shown in FIGS. 22A and 22B confirm that P31 peptide effectively induced cell death in all three cancer cell lines, but did not induce cell death in any of the three normal cell types. Control P33 peptide did not induce cell death in cancer or normal cell types.

Example 22

P31-Mediated Apoptosis is Dose Dependent

Figure 23:
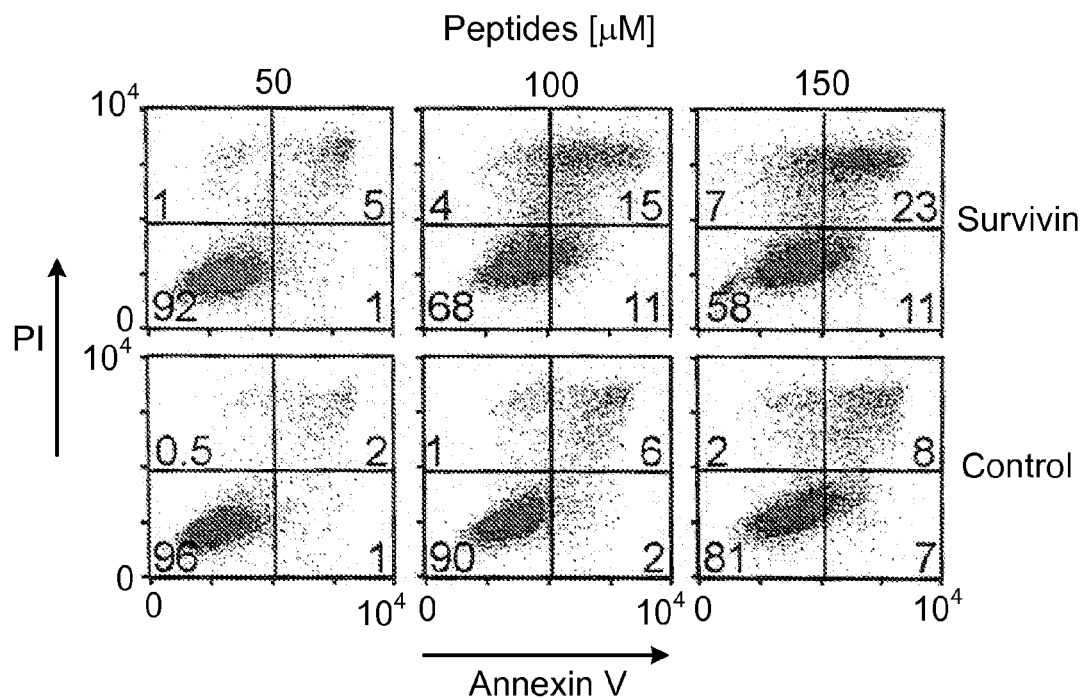
FIG. 23 depicts multiparametric flow cytometry results quantifying Annexin V labeling (X-axis, a marker of apoptosis) and propidium iodide staining (Y-axis, a marker of cell death). The results show that Survivin peptide induces apoptosis in a dose-dependent fashion whereas the control peptide is ineffective.

FIG. 23 shows the dose-response of induction of apoptosis by P31 peptide (SEQ ID NO:19) in HeLa cells using multiparametric flow cytometry of Annexin V labeling and propidium iodide staining. HeLa cell cultures were treated with the indicated increasing concentrations of P31 (Survivin) or P33 (Control; SEQ ID NO:25) peptides, harvested after an eight hour incubation at 37° C., and analyzed for multiparametric flow cytometry of Annexin V labeling (X-axis, a marker of apoptosis) and propidium iodide staining (Y-axis, a marker of cell death). The results show that the P31 peptide induced apoptosis in a dose-dependent manner, whereas the P33 control peptide was ineffective.

Example 23

P31 Peptide Binds Specifically to the Amino Terminus of Hsp90

Figure 24A:
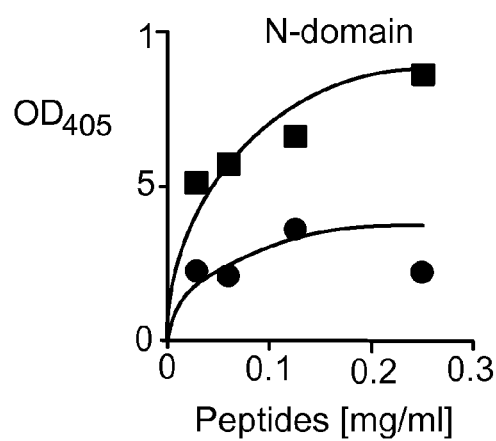
FIGS. 24A and 24B are graphs showing binding of Survivin peptide (compared with control peptide) to the N-terminal (FIG. 24A) and C-terminal (FIG. 24B) domains of Hsp90, as quantitated by ELISA experiments.
Figure 24B:
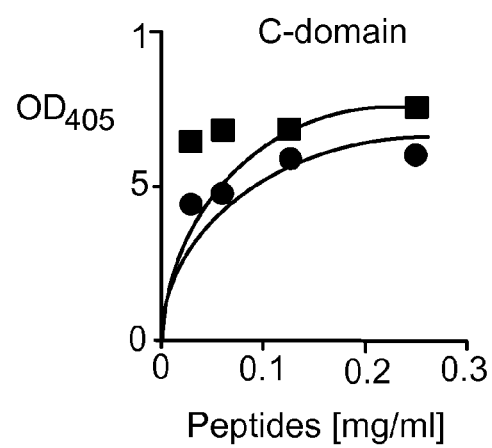

FIGS. 24A and 24B identify the location of P31 peptide's binding site as the N-terminus domain of Hsp90. The generation of recombinant Hsp90 fragments of the N-terminus or C-terminus is described in Example 3. ELISA experiments were performed as described in Example 2, except the indicated increasing concentrations of the P31 peptide (squares; SEQ ID NO:19) or control P33 peptide (circles; SEQ ID NO:25) were immobilized on plastic microtiter plates and incubated with the indicated Hsp90 N-terminal and C-terminal fragments. After washing, binding of the individual Hsp90 fragments to the immobilized peptides was detected with an antibody to Hsp90. Antibody to the C-terminal and N-terminal fragments of Hsp90 were obtained from BD/Transduction Laboratories and Santa Cruz Biotechnology, Inc. (Santa Cruz, Calif.), respectively. The results shown in FIGS. 24A and 24B show that P31 peptide bound specifically to the N-terminus of Hsp90, as indicated by the increase in $OD_{405}$ compared to the P33 peptide.

Example 24

Molecular Modeling of the Survivin Peptide

The structure of the Survivin retro-inverso peptide LFACGSSHK (all D amino acids) was modeled using long time scale Molecular Dynamics (MD) simulations in explicit water solvent. The peptidomimetic exhibited a dominant configuration with a turn involving G83-S84 and overall β-hairpin geometry (FIG. 25A). In MD simulations, the peptidomimetic docked into the ATP-binding site of Hsp90 (FIG. 25B). The geometry of the complex is highly correlated with that of the complex between Hsp90 and GA, with the turn region closely tracing the ansa ring backbone of GA (Stebbins et al., *Cell*, 89:239-50 (1997)). The Survivin peptidomimetic makes 18 predicted hydrogen bonds with Hsp90, involving the side chains of H86, S85, S84, the carbonyl group of G83, and the side chains of K87 and C82.

Example 25

Treatment of PC3 Prostate Cancer Cells with the Survivin K79-L87 Peptide Results in Loss of Hsp90 Client Proteins Survivin affects the stability and function of Hsp90 client proteins in tumor cells. PC3 cells were untreated or exposed to 75 and 150 μM concentrations of the survivin peptide (SEQ ID NO:19) (or control scrambled peptide; SEQ ID NO:25) for 8 hours and processed for immunoblotting against the Hsp90 client proteins survivin, AKT, and CDK-6. Cell permeable survivin peptide, but not scrambled peptide, caused disappearance of multiple Hsp90 client proteins in PC3 cells, including survivin, Akt, CDK-4, and CDK-6, by Western blotting (FIG. 26A). Conversely, the levels of Hsp90, Hsp70, and PCNA were not affected (FIG. 26A).

Survivin peptide treated PC3 cells were also tested for telomerase activity, which requires Hsp90 (Holt et al., *Genes Dev.*, 13:817-26 (1999)). Cells were treated as in above, immunoprecipitated with an antibody to Hsp90, and telomerase activity was determined by TRAP assay (Kim and Wu, *Nucleic Acids Res.*, 25:2595-7 (1997)) of the immunoprecipitates. Telomerase activity is indicated by a ladder of telomere products. As shown in FIG. 26B, treatment with the survivin peptide prior to immunoprecipitation abrogated telomerase activity in the assay.

These results indicate that the survivin peptide affects the stability and function of Hsp90 client proteins in tumor cells.

Example 26

Inhibition of Tumor Growth, In Vivo

Prostate cancer PC3 cells ($2.5 \times 10^6$) were injected in the flank of immunocompromised SCID/beige mice, and allowed to form palpable tumors (35-50 mm$^3$). Animals were randomized in two groups (6 animals/group) receiving saline or the cell permeable retro-inverso survivin K79-L87 peptide P3 (50 mg/kg/daily/i.p.). Tumor growth was measured with a caliper for a 12-d treatment interval. The survivin peptidomimetic greatly reduced the rate of tumor growth in this system (FIG. 25A).

To determine whether the survivin peptidomimetic accumulates intracellularly in vivo, animals carrying flank PC3 tumors were injected intraperitoneally with saline, or the cell-permeable retro-inverso K79-L87 survivin peptide P3. One hour after administration, the animals were sacrificed, and the tumors were carefully excised and analyzed for peptide accumulation within the tumor mass by fluorescence microscopy. The tumor cells showed intracellular fluorescence, indicating that the cells took up and accumulated the survivin peptidomimetic (FIG. 25B).

Example 27

Survivin Activity in AML Cell Lines

The expression and function of the survivin-Hsp90 pathway in acute myelogenous leukemia (AML) cell lines was analyzed. Survivin was abundantly expressed in four AML cell lines, U937, K-562, THP-1 and HL-60, by Western blotting (FIG. 29A). Treatment with cell-permeable survivin P31 peptide (SEQ ID NO:19) resulted in dose-dependent and complete cell killing of HL-60 cells, as measured by trypan blue exclusion, whereas the scrambled P33 peptide (SEQ ID NO:25) was ineffective (FIG. 29B). Similar results were obtained with the other AML cell lines.

The activity of a shorter Survivin peptide was also tested in an AML cell line. A shorter cell permeable Survivin peptide was synthesized by fusing the third α-helix of the Antennapedia carrier sequence to the amino-terminus of the Survivin peptide sequence K79-G83 (SEQ ID NO:20). This shorter peptide was considerably more active than the P31 peptide at reducing cell viability, as measured using MTT, in the AML cell lines (FIG. 29C, D). The scrambled control peptide (RQIKIWFQNRRMKWKKSGKHS; SEQ ID NO:28) was ineffective (FIG. 29C, D). For these experiments a higher number of cells was used ($4 \times 10^5$) to produce a 50% killing efficiency by full length survivin peptide.

Figure 30:
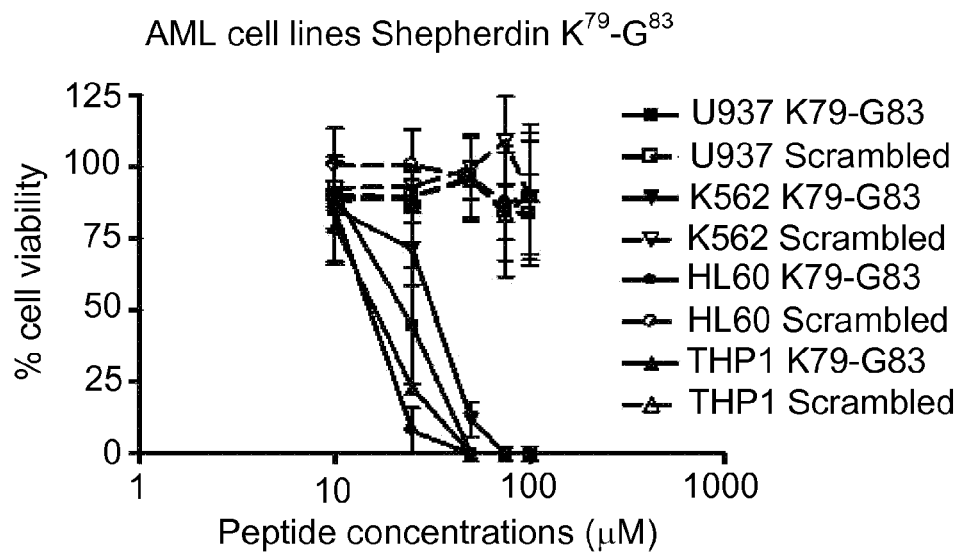
FIG. 30 is a graph depicting killing activity of survivin K79-G83 in AML cells. The indicated human AML cell lines (U937, K562, HL60, and THP1) were incubated with scrambled (SEQ ID NO:28) or Survivin (SEQ ID NO:20) peptides and evaluated for cell viability by MTT.

The effect of the K79-G83 Survivin peptide was characterized in more detail for anti-tumor activity in AML. The K79-L87 (SEQ ID NO:19) and K79-G83 peptides (SEQ ID NO:20) were incubated with AML cells, and cell viability was measured using MTT. Both K79-L87 and K79-G83 Survivin peptides efficiently killed all AML cell lines tested, whereas control scrambled sequences (SEQ ID NO:25 and SEQ ID NO:28) had no effect (FIG. 30).

Figure 31:
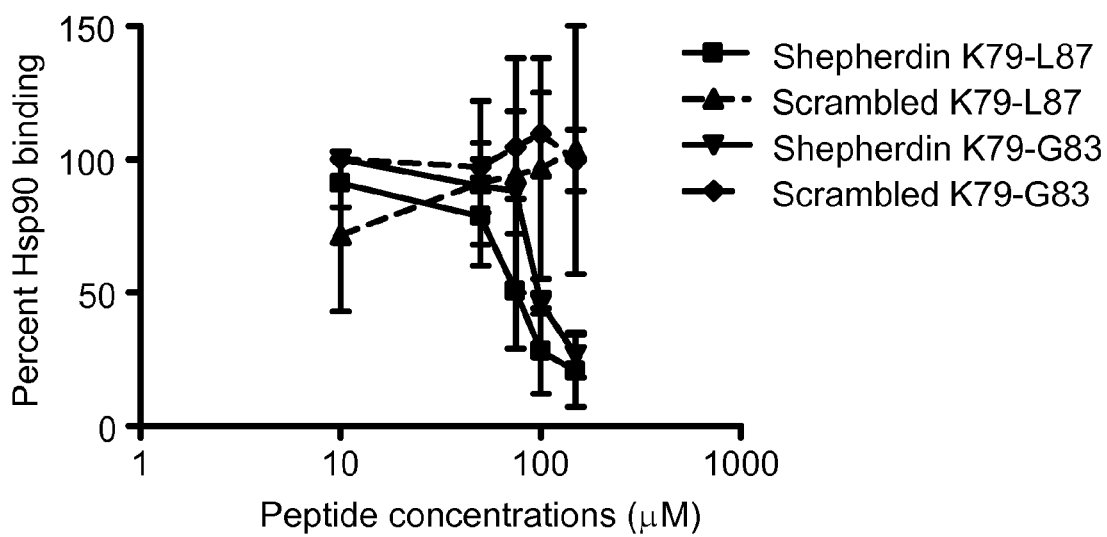
FIG. 31 is a graph depicting Hsp90 binding by Survivin peptides, measured by ELISA. Data are the mean±S.D. of two independent experiments.

Consistent with the functional results of anti-tumor activity, both Survivin sequences K79-L87 and K79-G83 comparably bound recombinant Hsp90 in vitro and inhibited the binding of recombinant survivin to Hsp90 in a dose-dependent manner (FIG. 31).

Example 28

Figure 32:
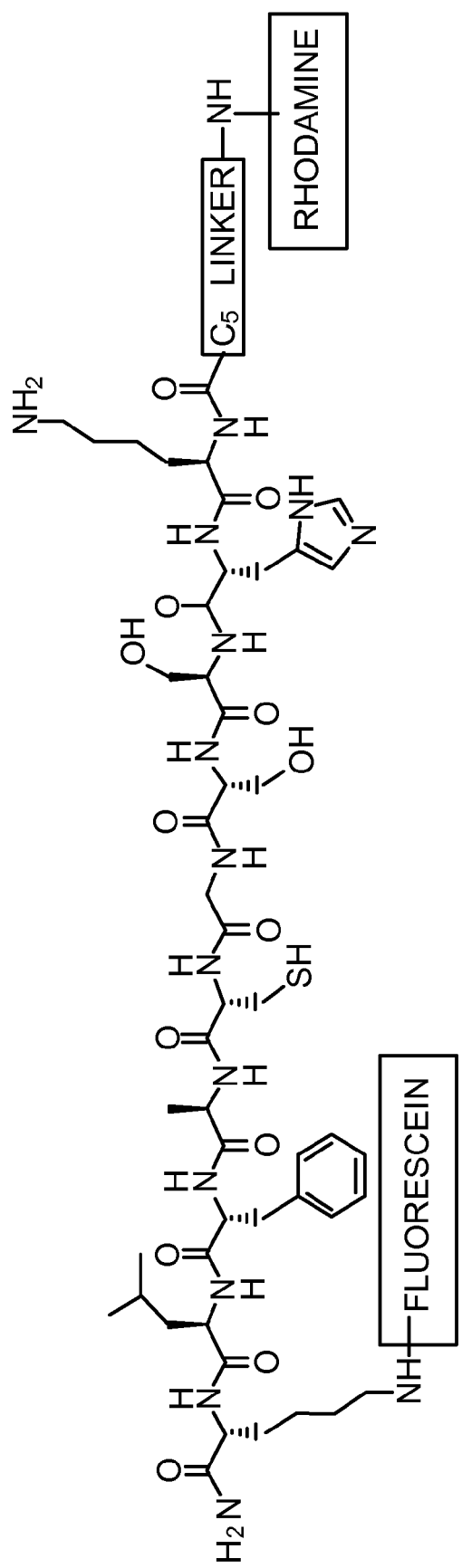
FIG. 32 is a depiction of the molecular structure of a Survivin peptide conjugated to fluorescein and rhodamine for use in FRET and/or FP methods. For FP methods, the Survivin peptide can be conjugated to only one of the fluorophores.

High Throughput Screening to Identify Small Molecule Antagonists of the Survivin Peptide-Hsp90 Interaction High Throughput Screening (HTS) is used to identify small molecule antagonists of the Survivin peptide-Hsp90 interaction. Two experimental strategies are used for the screening, fluorescence resonance energy transfer (FRET) and fluorescence polarization (FP). A Survivin peptide is prepared labeled with dye molecules according to methods known in the art. The structure of the peptide-dye conjugate is outlined in FIG. 32. In this molecule, sites at either end of the Survivin peptide are labeled with Fluorescein (Fl; donor) or Rhodamine (Rh; receptor).

The free peptide has high FRET efficiency due to intramolecular FRET between donor and acceptor sites causing quenching of fluorescence intensity. Upon binding to Hsp90, the intramolecular FRET of the peptide-dye conjugate decreases, and the donor signal increases. From the changes in relative donor fluorescence (Fl), a binding dissociation constant ($K_D$) is obtained by non-linear regression fitting.

The overall HTS strategy using FRET is as follows. An inhibitor from a chemical library that competitively binds to Hsp90 will release the Survivin peptide-dye conjugate to its natural folding conformation. This results in increased FRET efficiency with decreased donor fluorescence intensity and increased acceptor signal at increasing inhibitor concentrations. The inhibitor binding dissociation constant $K_i$ is obtained by fitting a plot with relative fluorescence intensity of Fl as a function of inhibitor concentration.

For screening, the signal to noise ratio is optimized to obtain maximal FRET signals within the Survivin peptide-dye conjugate using 50 µM of final concentration of the compound for identification of primary hits. Control experiments are performed to detect any solvent effects on FRET efficiencies.

In another example, FP is used to monitor the Survivin peptide-Hsp90 interaction. A fluorescein-labeled Survivin peptide rotates at fast rates and exhibits low fluorescence polarization. Conversely, binding to Hsp90 results in slower rotation rates with increased fluorescence polarization. Anisotropy (r) is used to quantify the fluorescence polarization and is defined as the ratio of the difference between parallel fluorescence intensity and perpendicular intensity and total fluorescence. A $K_D$ value for the interaction is obtained by fitting the plot of r as a function of concentration of protein.

The chemical library used in the HTS experiments is obtained from Chem. Bridge Corporation (San Diego, Calif.), with 330,000 small molecule compounds selected by computational diversity and drug-like property analysis. By using various filters including solubility profiles, Log P, ionic charge, rotatable bond data, polar surface area calculations, and number of heteroatoms, a diverse set of 30,000 molecules is selected. These molecules are distributed in 96-well plates dissolved in DMSO at 5 mM concentration. All plates are bar-coded for convenient identification of small molecules.

The goal of the primary screen is to identify compounds that competitively inhibit the Survivin-Hsp90 interaction.

Using the dual FRET/FP approach described above, the entire library is quickly and conveniently screened with isolation of 1-3% of primary hit compounds, corresponding to 300-900 molecules from the library. These primary hit compounds are tested in a secondary screen to identify lead molecules with Survivin peptide-like properties. To enhance the specificity of the secondary screening, N-domain Hsp90 mutants that exhibit reduced binding to Survivin peptide (N51A, S52A or S113A substituted variants of SEQ ID NO:21) (Plescia et al., Cancer Cell, 7:457-68 (2005)) are tested in parallel with wild type Hsp90.

As tertiary screening, the selected compounds are synthesized individually on a 20 mg scale, and their $IC_{50}$ values for inhibition of Hsp90 are determined. Two independent experimental readouts are used in parallel in the tertiary screening: (i) inhibition of Hsp90 ATPase activity (enzymatic repression assay), and (ii) inhibition of survivin-Hsp90 interaction (protein-protein interaction assay). In the first set of experiments, increasing concentrations of the individual compounds are tested in a 96-well plate format for modulation of relative fluorescence emission of MDCC-labeled phosphate binding protein (PBP, 1 μM) in the presence of 4 μg of recombinant Hsp90. GA (60 μM) is used as a control for these experiments. In the second set of experiments, increasing concentrations of selected compounds are mixed with reticulocyte extracts (100 μl), incubated with recombinant survivin (0.5 μg), and further immunoprecipitated with control IgG or an antibody to Hsp90. Differential binding of survivin to Hsp90 in the presence of the various compounds is determined by Western blotting, and quantified by densitometry. Preincubation of reticulocyte extracts with Survivin peptide or scrambled peptide is used as control.

Example 29

Validation of Small Molecule Antagonists of the Survivin Peptide-Hsp90 Interaction The identified Hsp90-inhibiting compounds are stratified into structural classes based on structural similarity and into strong and weak inhibitors of Hsp90 function based on the relative $IC_{50}$ values (a rough gauge of binding affinity). The compounds are individually synthesized on a 50 mg scale. The "strongest" inhibitors from each structural class are prepared first, and further characterized for their binding affinities to Hsp90 by fluorescence anisotropy. For these experiments, Hsp90 binding compounds are labeled with fluorescein and their binding affinities to wild type or mutant N-domain Hsp90 are determined. Various linkers (6-12 carbon) are used between the dye and the compound so that the activity of the compound is not influenced. Alternatively, Hsp90 is labeled with dye molecules, and unlabeled Hsp90 binding compounds are used for these experiments.

Next, the validated compounds are tested in cell-based studies for effects on cell viability and apoptosis. For these experiments, increasing concentrations of the various compounds are incubated with tumor cell lines, including AML cells ($1 \times 10^7$/ml) or normal human fibroblasts for increasing time intervals (0.5-36 hours) at 37° C. Cells are differentially analyzed for plasma membrane integrity by Trypan blue exclusion, cell viability by MTT, lysosomal permeability by aminotrifluoromethylcoumarin (AFC) fluorescence analysis, and apoptosis by determination of mitochondrial dysfunction and multiparametric flow cytometry of DEVDase activity/ Annexin V and PI labeling.

The specificity of the compounds for Hsp90 binding and inhibition of chaperone function is further investigated. First, increasing concentrations of the compounds are analyzed for competitive inhibition of Hsp90 binding to γ-phosphate-linked ATP-Sepharose by affinity chromatography, and independently tested for differential binding to Hsp90 versus Hsp70 by fluorescence polarization. Secondly, tumor cells, including AML cells, are incubated with increasing concentrations of the selected compounds, harvested at 0.5-36 hours of incubation, and analyzed for loss of Hsp90 client proteins, e.g., survivin, Akt, CDK-4, CDK-6, c-Raf-1, and c-Src, by Western blotting, and telomerase activity by TRAP assay on Hsp90 immunoprecipitates. Normal or tumor cell lines incubated with 17-(Allylamino)-17-demethoxygeldanamycin (17-AAG) (5-10 μM), or cell permeable Survivin peptide or scrambled peptide are used as controls for these validation experiments.

Example 30

In Vivo Testing of Small Molecule Antagonists of the Survivin Peptide-Hsp90 Interaction Small molecule Survivin peptide mimics with activity on tumor cell lines are tested for efficacy in vivo in a human AML xenograft model. HL-60 cells ($5 \times 10^6$) are suspended in sterile PBS, pH 7.4, in a total volume of 100 μl, and injected into the tail vein of eight-to-ten week old CB-17 SCID/beige mice (20-25 g). Animals are inspected daily for general signs of disease (paralysis, lethargy, ruffled fur), which becomes clinically evident 10-14 days after engraftment and causes 100% lethality in 3-5 weeks if left untreated. To facilitate bone marrow engraftment, animals receive a preconditioning sublethal irradiation dose (350 R) from a linear accelerator. HL-60 cell accumulation in the spleen and bone marrow are determined by immunocytochemistry with an antibody to human HLA at weekly intervals after reconstitution. At time of engraftment, animals receive a small molecule Survivin peptide mimic using a short term (15 days) or a long term (50 days) regimen with doses (0.01-50 mg/kg) administered intraperitoneally. Control animals are injected with saline. Efficacy is determined by increased survival rates of treated versus control animals.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating breast cancer, the method comprising:
   selecting a subject diagnosed as having breast cancer associated with overexpression of Survivin; and
   administering to the selected subject a therapeutically effective amount of a pharmaceutical composition comprising a compound:
   (i) consisting of a D-amino acid peptide selected from the group consisting of: (D-Leu)-(D-Phe)-(D-Ala)-(D-Cys)-(D-Gly)-(D-Ser)-(D-Ser)-(D-His)-(D-Lys); (D-Cys)-(D-Gly)-(D-Ser)-(D-Ser)-(D-His); and (D-Gly)-(D-Ser)-(D-Ser)-(D-His)-(D-Lys); or
   (ii) comprising the formula X-A or A-X, wherein A consists of a D-amino acid sequence selected from the group consisting of: (D-Leu)-(D-Phe)-(D-Ala)-(D-Cys)-(D-Gly)-(D-Ser)-(D-Ser)-(D-His)-(D-Lys); (D-Cys)-(D-Gly)-(D-Ser)-(D-Ser)-(D-His); and (D-Gly)-(D-Ser)-(D-Ser)-(D-His)-(D-Lys); and X consists of an internalization peptide sequence of a protein selected from the group consisting of: Tat, Antennapedia, VP22, Pep-1, and transportan, or a retro-inverso version of said internalization peptide sequence.

2. The method of claim 1, wherein the compound comprises the formula X-A or A-X, wherein:
   A consists of a D-amino acid sequence selected from the group consisting of: (D-Leu)-(D-Phe)-(D-Ala)-(D-Cys)-(D-Gly)-(D-Ser)-(D-Ser)-(D-His)-(D-Lys); (D-Cys)-(D-Gly)-(D-Ser)-(D-Ser)-(D-His); and (D-Gly)-(D-Ser)-(D-Ser)-(D-His)-(D-Lys); and
   X consists of an internalization peptide sequence of a protein selected from the group consisting of: Tat, Antennapedia, VP22, Pep-1, and transportan, or a retro-inverso version of said internalization peptide sequence.

3. The method of claim 2, wherein the compound comprises a D-amino acid sequence selected from:
   (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Cys)-(D-Gly)-(D-Ser)-(D-Ser)-(D-His);
   (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Leu)-(D-Phe)-(D-Ala)-(D-Cys)-(D-Gly)-(D-Ser)-(D-Ser)-(D-His)-(D-Lys); and
   (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Gly)-(D-Ser)-(D-Ser)-(D-His)-(D-Lys).

4. The method of claim 3, wherein the compound comprises the D-amino acid sequence (D-Lys)-(D-Lys)-(D-Trp)-(D-Lys)-(D-Met)-(D-Arg)-(D Arg)-(D-Asn)-(D-Gln)-(D-Phe)-(D-Trp)-(D-Val)-(D-Lys)-(D-Val)-(D-Gln)-(D-Arg)-(D-Leu)-(D-Phe)-(D-Ala)-(D-Cys)-(D-Gly)-(D-Ser)-(D-Ser)-(D-His)-(D-Lys).

5. The method of claim 4, wherein the compound consists of the D-amino acid peptide (D-Lys)-(D-Lys)-(D-Trp)-(D-Lys)-(D-Met)-(D-Arg)-(D-Arg)-(D-Asn)-(D-Gln)-(D Phe)-(D-Trp)-(D-Val)-(D-Lys)-(D-Val)-(D-Gln)-(D-Arg)-(D-Leu)-(D-Phe)-(D-Ala)-(D Cys)-(D-Gly)-(D-Ser)-(D-Ser)-(D-His)-(D-Lys).

6. The method of claim 3, wherein the compound comprises the D-amino acid sequence (D-Lys)-(D-Lys)-(D-Trp)-(D-Lys)-(D-Met)-(D-Arg)-(D Arg)-(D-Asn)-(D-Gln)-(D-Phe)-(D-Trp)-(D-Val)-(D-Lys)-(D-Val)-(D-Gln)-(D-Arg)-(D Cys)-(D-Gly)-(D-Ser)-(D-Ser)-(D-His) or the D-amino acid sequence (D-Lys)-(D-Lys)-(D-Trp)-(D-Lys)-(D-Met)-(D-Arg)-(D Arg)-(D-Asn)-(D-Gln)-(D-Phe)-(D-Trp)-(D-Val)-(D-Lys)-(D-Val)-(D-Gln)-(D-Arg)-(D Gly)-(D-Ser)-(D-Ser)-(D-His)-(D-Lys).

7. The method of claim 6, wherein the compound consists of the D-amino acid peptide (D-Lys)-(D-Lys)-(D-Trp)-(D-Lys)-(D-Met)-(D-Arg)-(D-Arg)-(D-Asn)-(D-Gln)-(D Phe)-(D-Trp)-(D-Val)-(D-Lys)-(D-Val)-(D-Gln)-(D-Arg)-(D-Cys)-(D-Gly)-(D-Ser)-(D-Ser)-(D-His) or the D-amino acid peptide (D-Lys)-(D-Lys)-(D-Trp)-(D-Lys)-(D-Met)-(D-Arg)-(D-Arg)-(D-Asn)-(D-Gln)-(D Phe)-(D-Trp)-(D-Val)-(D-Lys)-(D-Val)-(D-Gln)-(D-Arg)-(D-Gly)-(D-Ser)-(D-Ser)-(D-His)-(D-Lys).

8. The method of claim 1, wherein the pharmaceutical composition is administered by intravenous or subcutaneous administration.

9. A method of inducing apoptosis in a breast tumor cell in a subject, the method comprising administering to a subject in need thereof an effective amount of a pharmaceutical composition comprising an isolated compound:
   (i) consisting of a D-amino acid peptide selected from the group consisting of: (D-Leu)-(D-Phe)-(D-Ala)-(D-Cys)-(D-Gly)-(D-Ser)-(D-Ser)-(D-His)-(D-Lys); (D-Cys)-(D-Gly)-(D-Ser)-(D-Ser)-(D-His); and (D-Gly)-(D-Ser)-(D-Ser)-(D-His)-(D-Lys); or
   (ii) comprising the formula X-A or A-X, wherein A consists of a D-amino acid sequence selected from the group consisting of: (D-Leu)-(D-Phe)-(D-Ala)-(D-Cys)-(D-Gly)-(D-Ser)-(D-Ser)-(D-His)-(D-Lys); (D-Cys)-(D-Gly)-(D-Ser)-(D-Ser)-(D-His); and (D-Gly)-(D-Ser)-(D-Ser)-(D-His)-(D-Lys); and X consists of an internalization peptide sequence of a protein selected from the group consisting of: Tat, Antennapedia, VP22, Pep-1, and transportan, or a retro-inverso version of said internalization peptide sequence.

10. The method of claim 9, wherein the compound comprises the formula X-A or A-X, wherein:
    A consists of a D-amino acid sequence selected from the group consisting of: (D-Leu)-(D-Phe)-(D-Ala)-(D-

Cys)-(D-Gly)-(D-Ser)-(D-Ser)-(D-His)-(D-Lys);
(D-Cys)-(D-Gly)-(D-Ser)-(D-Ser)-(D-His); and
(D-Gly)-(D-Ser)-(D-Ser)-(D-His)-(D-Lys); and X consists of an internalization peptide sequence of a protein selected from the group consisting of: Tat, Antennapedia, VP22, Pep-1, and transportan, or a retro-inverso version of said internalization peptide sequence.

11. The method of claim 10, wherein the compound comprises a D-amino acid sequence selected from:

(D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Cys)-(D-Gly)-(D-Ser)-(D-Ser)-(D-His);

(D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Leu)-(D-Phe)-(D-Ala)-(D-Cys)-(D-Gly)-(D-Ser)-(D-Ser)-(D-His)-(D-Lys); and (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Gly)-(D-Ser)-(D-Ser)-(D-His)-(D-Lys).

12. The method of claim 11, wherein the compound comprises the D-amino acid sequence (D-Lys)-(D-Lys)-(D-Trp)-(D-Lys)-(D-Met)-(D-Arg)-(D Arg)-(D-Asn)-(D-Gln)-(D-Phe)-(D-Trp)-(D-Val)-(D-Lys)-(D-Val)-(D-Gln)-(D-Arg)-(D-Leu)-(D-Phe)-(D-Ala)-(D-Cys)-(D-Gly)-(D-Ser)-(D-Ser)-(D-His)-(D-Lys).

13. The method of claim 12, wherein the compound consists of the D-amino acid peptide (D-Lys)-(D-Lys)-(D-Trp)-(D-Lys)-(D-Met)-(D-Arg)-(D-Arg)-(D-Asn)-(D-Gln)-(D Phe)-(D-Trp)-(D-Val)-(D-Lys)-(D-Val)-(D-Gln)-(D-Arg)-(D-Leu)-(D-Phe)-(D-Ala)-(D-Cys)-(D-Gly)-(D-Ser)-(D-Ser)-(D-His)-(D-Lys).

14. The method of claim 11, wherein the compound comprises the D-amino acid sequence (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D Cys)-(D-Gly)-(D-Ser)-(D-Ser)-(D-His) or the D-amino acid sequence (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Gly)-(D-Ser)-(D-Ser)-(D-His)-(D-Lys).

15. The method of claim 14, wherein the compound consists of the D-amino acid peptide (D-Lys)-(D-Lys)-(D-Trp)-(D-Lys)-(D-Met)-(D-Arg)-(D-Arg)-(D-Asn)-(D-Gln)-(D Phe)-(D-Trp)-(D-Val)-(D-Lys)-(D-Val)-(D-Gln)-(D-Arg)-(D-Cys)-(D-Gly)-(D-Ser)-(D-Ser)-(D-His) or the D-amino acid peptide (D-Lys)-(D-Lys)-(D-Trp)-(D-Lys)-(D-Met)-(D-Arg)-(D-Arg)-(D-Asn)-(D-Gln)-(D-Phe)-(D-Trp)-(D-Val)-(D-Lys)-(D-Val)-(D-Gln)-(D-Arg)-(D-Gly)-(D-Ser)-(D-Ser)-(D-His)-(D-Lys).

16. The method of claim 9, wherein the pharmaceutical composition is administered by intravenous or subcutaneous administration.

* * * * *

UNITED STATES PATENT AND TRADEMARK OFFICE
CERTIFICATE OF CORRECTION

PATENT NO. : 9,035,024 B2  
APPLICATION NO. : 13/861959  
DATED : May 19, 2015  
INVENTOR(S) : Altieri et al.

Page 1 of 1

It is certified that error appears in the above-identified patent and that said Letters Patent is hereby corrected as shown below:

Title page, column 2, line 27, item (56) Other Publications, delete "*survivin*in" and insert -- survivin in --.

In the Claims

Column 59, line 67, Claim 4, delete "D   Arg" and insert -- D-Arg --.

Column 60, line 19, Claim 5, delete "D   Phe" and insert -- D-Phe --.

Column 60, line 21, Claim 5, delete "D   Cys" and insert -- D-Cys --.

Column 60, line 26, Claim 6, delete "D   Arg" and insert -- D-Arg --.

Column 60, line 28, Claim 6, delete "D   Cys" and insert -- D-Cys --.

Column 60, line 30, Claim 6, delete "D   Arg" and insert -- D-Arg --.

Column 60, line 31, Claim 6, delete "D   Gly" and insert -- D-Gly --.

Column 60, line 35, Claim 7, delete "D   Phe" and insert -- D-Phe --.

Column 60, line 39, Claim 7, delete "D   Phe" and insert -- D-Phe --.

Column 61, line 25, Claim 12, delete "D   Arg" and insert -- D-Arg --.

Column 62, lines 3-4, Claim 13, delete "D   Phe" and insert -- D-Phe --.

Column 62, line 11, Claim 14, delete "D   Cys" and insert -- D-Cys --.

Column 62, lines 18-19, Claim 15, delete "D   Phe" and insert -- D-Phe --.

Signed and Sealed this  
Third Day of November, 2015

Michelle K. Lee  
*Director of the United States Patent and Trademark Office*

SEQUENCE LISTING

<160> NUMBER OF SEQ ID NOS: 29

<210> SEQ ID NO 1
<211> LENGTH: 142
<212> TYPE: PRT
<213> ORGANISM: Homo sapiens

<400> SEQUENCE: 1

Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
             20                  25                  30

Cys Thr Pro Glu Arg Met Ala Glu Ala Gly Phe Ile His Cys Pro Thr
         35                  40                  45

Glu Asn Glu Pro Asp Leu Ala Gln Cys Phe Phe Cys Phe Lys Glu Leu
     50                  55                  60

Glu Gly Trp Glu Pro Asp Asp Asp Pro Ile Glu Glu His Lys Lys His
 65                  70                  75                  80

Ser Ser Gly Cys Ala Phe Leu Ser Val Lys Lys Gln Phe Glu Glu Leu
             85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
            115                 120                 125

Lys Lys Val Arg Arg Ala Ile Glu Gln Leu Ala Ala Met Asp
130                 135                 140

<210> SEQ ID NO 2
<211> LENGTH: 5
<212> TYPE: PRT
<213> ORGANISM: Homo sapiens

<400> SEQUENCE: 2

His Ser Ser Gly Cys
 1               5

<210> SEQ ID NO 3
<211> LENGTH: 12
<212> TYPE: PRT
<213> ORGANISM: Homo sapiens

<400> SEQUENCE: 3

Lys His Ser Ser Gly Cys Ala Phe Leu Ser Val Lys
 1               5                  10

<210> SEQ ID NO 4
<211> LENGTH: 14
<212> TYPE: PRT
<213> ORGANISM: Homo sapiens

<400> SEQUENCE: 4

Ile Asp Asp His Lys Lys His Ser Ser Gly Cys Ala Phe Leu
 1               5                  10

<210> SEQ ID NO 5
<211> LENGTH: 10
<212> TYPE: PRT
<213> ORGANISM: Homo sapiens

<400> SEQUENCE: 5

Lys Lys His Ser Ser Gly Cys Ala Phe Leu
 1               5                  10

<210> SEQ ID NO 6
<211> LENGTH: 6
<212> TYPE: PRT
<213> ORGANISM: Homo sapiens

```
<400> SEQUENCE: 6

Lys His Ser Ser Gly Cys
  1               5

<210> SEQ ID NO 7
<211> LENGTH: 6
<212> TYPE: PRT
<213> ORGANISM: Homo sapiens

<400> SEQUENCE: 7

His Ser Ser Gly Cys Ala
  1               5

<210> SEQ ID NO 8
<211> LENGTH: 7
<212> TYPE: PRT
<213> ORGANISM: Homo sapiens

<400> SEQUENCE: 8

Lys His Ser Ser Gly Cys Ala
  1               5

<210> SEQ ID NO 9
<211> LENGTH: 7
<212> TYPE: PRT
<213> ORGANISM: Homo sapiens

<400> SEQUENCE: 9

Lys Lys His Ser Ser Gly Cys
  1               5

<210> SEQ ID NO 10
<211> LENGTH: 7
<212> TYPE: PRT
<213> ORGANISM: Homo sapiens

<400> SEQUENCE: 10

His Ser Ser Gly Cys Ala Phe
  1               5

<210> SEQ ID NO 11
<211> LENGTH: 3
<212> TYPE: PRT
<213> ORGANISM: Homo sapiens

<400> SEQUENCE: 11

His Ser Ser
  1

<210> SEQ ID NO 12
<211> LENGTH: 3
<212> TYPE: PRT
<213> ORGANISM: Homo sapiens

<400> SEQUENCE: 12

Ser Ser Gly
  1

<210> SEQ ID NO 13
<211> LENGTH: 3
<212> TYPE: PRT
<213> ORGANISM: Homo sapiens

<400> SEQUENCE: 13
```

Ser Gly Cys
1

<210> SEQ ID NO 14
<211> LENGTH: 4
<212> TYPE: PRT
<213> ORGANISM: Homo sapiens

<400> SEQUENCE: 14

His Ser Ser Gly
1

<210> SEQ ID NO 15
<211> LENGTH: 4
<212> TYPE: PRT
<213> ORGANISM: Homo sapiens

<400> SEQUENCE: 15

Ser Ser Gly Cys
1

<210> SEQ ID NO 16
<211> LENGTH: 66
<212> TYPE: PRT
<213> ORGANISM: Homo sapiens

<400> SEQUENCE: 16

Arg Leu Lys Thr Phe Ala Asn Phe Pro Ser Gly Ser Pro Val Ser Ala
1               5                   10                  15

Ser Thr Leu Ala Arg Ala Gly Phe Leu Tyr Thr Gly Glu Gly Asp Thr
            20                  25                  30

Val Arg Cys Phe Ser Cys His Ala Ala Val Asp Arg Trp Gln Tyr Gly
        35                  40                  45

Asp Ser Ala Val Gly Arg His Arg Lys Val Ser Pro Asn Cys Arg Phe
    50                  55                  60

Ile Asn
65

<210> SEQ ID NO 17
<211> LENGTH: 66
<212> TYPE: PRT
<213> ORGANISM: Homo sapiens

<400> SEQUENCE: 17

Arg Met Ser Thr Tyr Ser Thr Phe Pro Ala Gly Val Pro Val Ser Glu
1               5                   10                  15

Arg Ser Leu Ala Arg Ala Gly Phe Tyr Tyr Thr Gly Val Asn Asp Lys
            20                  25                  30

Val Lys Cys Phe Cys Cys Gly Leu Met Leu Asp Asn Trp Lys Arg Gly
        35                  40                  45

Asp Ser Pro Thr Glu Lys His Lys Lys Leu Tyr Pro Ser Cys Arg Phe
    50                  55                  60

Val Gln
65

<210> SEQ ID NO 18
<211> LENGTH: 66
<212> TYPE: PRT
<213> ORGANISM: Homo sapiens

<400> SEQUENCE: 18

```
Arg Met Ser Thr Tyr Ser Thr Phe Pro Ala Gly Val Pro Val Ser Glu
 1               5                  10                  15

Arg Ser Leu Ala Arg Ala Gly Phe Tyr Tyr Thr Gly Val Asn Asp Lys
            20                  25                  30

Val Lys Cys Phe Cys Cys Gly Leu Met Leu Asp Asn Trp Lys Leu Gly
        35                  40                  45

Asp Ser Pro Ile Gln Lys His Lys Gln Leu Tyr Pro Ser Cys Ser Phe
    50                  55                  60

Ile Gln
65

<210> SEQ ID NO 19
<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 19

Arg Gln Ile Lys Ile Trp Phe Gln Asn Arg Arg Met Lys Trp Lys Lys
 1               5                  10                  15

Lys His Ser Ser Gly Cys Ala Phe Leu
            20                  25

<210> SEQ ID NO 20
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 20

Arg Gln Ile Lys Ile Trp Phe Gln Asn Arg Arg Met Lys Trp Lys Lys
 1               5                  10                  15

Lys His Ser Ser Gly
            20

<210> SEQ ID NO 21
<211> LENGTH: 732
<212> TYPE: PRT
<213> ORGANISM: Homo sapiens

<400> SEQUENCE: 21

Met Pro Glu Glu Thr Gln Thr Gln Asp Gln Pro Met Glu Glu Glu Glu
 1               5                  10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Thr Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125
```

```
Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
                180                 185                 190

Asp Gln Thr Glu Tyr Leu Glu Glu Arg Arg Ile Lys Glu Ile Val Lys
                195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Ser Glu Asp Lys Pro
                245                 250                 255

Glu Ile Glu Asp Val Gly Ser Asp Glu Glu Glu Lys Lys Asp Gly
                260                 265                 270

Asp Lys Lys Lys Lys Lys Ile Lys Glu Lys Tyr Ile Asp Gln Glu
                275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320

Glu Asp His Leu Ala Val Lys His Phe Ser Val Glu Gly Gln Leu Glu
                325                 330                 335

Phe Arg Ala Leu Leu Phe Val Pro Arg Arg Ala Pro Phe Asp Leu Phe
                340                 345                 350

Glu Asn Arg Lys Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
    370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
                420                 425                 430

Asn Tyr Lys Lys Phe Tyr Glu Gln Phe Ser Lys Asn Ile Lys Leu Gly
                435                 440                 445

Ile His Glu Asp Ser Gln Asn Arg Lys Lys Leu Ser Glu Leu Leu Arg
    450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510
```

```
Lys His Gly Leu Glu Val Ile Tyr Met Ile Glu Pro Ile Asp Glu Tyr
            515                 520                 525

Cys Val Gln Gln Leu Lys Glu Phe Glu Gly Lys Thr Leu Val Ser Val
        530                 535                 540

Thr Lys Glu Gly Leu Glu Leu Pro Glu Asp Glu Glu Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Val Val Ser Asn Arg Leu
            580                 585                 590

Val Thr Ser Pro Cys Cys Ile Val Thr Ser Thr Tyr Gly Trp Thr Ala
        595                 600                 605

Asn Met Glu Arg Ile Met Lys Ala Gln Ala Leu Arg Asp Asn Ser Thr
        610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
            660                 665                 670

Ser Ser Gly Phe Ser Leu Glu Asp Pro Gln Thr His Ala Asn Arg Ile
        675                 680                 685

Tyr Arg Met Ile Lys Leu Gly Leu Gly Ile Asp Glu Asp Pro Thr
        690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 22
<211> LENGTH: 15
<212> TYPE: PRT
<213> ORGANISM: Homo sapiens

<400> SEQUENCE: 22

His Lys Lys His Ser Ser Gly Cys Ala Phe Leu Ser Val Lys Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 23

His Lys Lys His Ser Ser Gly Ala Ala Phe Leu Ser Val Lys Lys
1               5                   10                  15

<210> SEQ ID NO 24
<211> LENGTH: 9
<212> TYPE: PRT
<213> ORGANISM: Homo sapiens

<400> SEQUENCE: 24

Lys His Ser Ser Gly Cys Ala Phe Leu
1               5

<210> SEQ ID NO 25
```

<211> LENGTH: 25
<212> TYPE: PRT
<213> ORGANISM: Artificial Sequence
<220> FEATURE:
<223> OTHER INFORMATION: Synthetically generated peptide

<400> SEQUENCE: 25

Arg Gln Ile Lys Ile Trp Phe Gln Asn Arg Arg Met Lys Trp Lys Lys
1               5                   10                  15

Ser Lys Leu Ala Cys Phe Ser His Gly
            20                  25

<210> SEQ ID NO 26
<211> LENGTH: 5
<212> TYPE: PRT
<213> ORGANISM: Homo sapiens

<400> SEQUENCE: 26

Lys His Ser Ser Gly
1               5

<210> SEQ ID NO 27
<211> LENGTH: 123
<212> TYPE: PRT
<213> ORGANISM: Homo sapiens

<400> SEQUENCE: 27

Met Thr Phe Asn Ser Phe Glu Gly Ser Lys Thr Cys Val Pro Ala Asp
1               5                   10                  15

Ile Asn Lys Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
            35                  40                  45

Arg Ala Gly Phe Leu Tyr Thr Gly Glu Gly Asp Thr Val Arg Cys Phe
        50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser
        115                 120

<210> SEQ ID NO 28
<211> LENGTH: 21
<212> TYPE: PRT
<213> ORGANISM: Artificial Sequence
<220> FEATURE:
<223> OTHER INFORMATION: Synthetically generated peptide

<400> SEQUENCE: 28

Arg Gln Ile Lys Ile Trp Phe Gln Asn Arg Arg Met Lys Trp Lys Lys
1               5                   10                  15

Ser Gly Lys His Ser
            20

```
<210> SEQ ID NO 29
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 29

Arg Gln Lys Ile Trp Phe Gln Asn Arg Arg Met Lys Trp Lys Lys
1               5                   10                  15
```